(12) United States Patent
Perán Quesada et al.

(10) Patent No.: US 11,376,313 B2
(45) Date of Patent: Jul. 5, 2022

(54) CANCER TREATMENT

(71) Applicant: Propanc Pty Ltd, Camberwell (AU)

(72) Inventors: Macarena Perán Quesada, Camberwell (AU); Julian Kenyon, Camberwell (AU); Juan Antonio Marchal Corrales, Camberwell (AU); Maria Angel Garcia Chaves, Camberwell (AU)

(73) Assignee: PROPANC PTY LTD, Camberwell (AU)

( * ) Notice: Subject to any disclaimer, the term of this patent is extended or adjusted under 35 U.S.C. 154(b) by 97 days.

(21) Appl. No.: 16/073,247

(22) PCT Filed: Jan. 27, 2017

(86) PCT No.: PCT/AU2017/050065
§ 371 (c)(1),
(2) Date: Jul. 26, 2018

(87) PCT Pub. No.: WO2017/127892
PCT Pub. Date: Aug. 3, 2017

(65) Prior Publication Data
US 2019/0038725 A1     Feb. 7, 2019

(30) Foreign Application Priority Data

Jan. 29, 2016  (ES) ............... ES201630112
Dec. 22, 2016  (ES) ............... ES201631662

(51) Int. Cl.
*A61P 35/00* (2006.01)
*A61K 38/48* (2006.01)
*A61K 38/47* (2006.01)

(52) U.S. Cl.
CPC .......... *A61K 38/4826* (2013.01); *A61K 38/47* (2013.01); *A61P 35/00* (2018.01); *C12Y 304/21001* (2013.01); *C12Y 304/21004* (2013.01); *A61K 2300/00* (2013.01)

(58) Field of Classification Search
CPC ................................................. A61K 38/4826
USPC ....................................................... 514/19.3
See application file for complete search history.

(56) References Cited

U.S. PATENT DOCUMENTS

| | | | |
|---|---|---|---|
| 4,514,388 A | 4/1985 | Psaledakis | |
| 4,978,332 A | 12/1990 | Luck et al. | |
| 5,595,756 A | 1/1997 | Bally et al. | |
| 5,858,357 A | 1/1999 | Trnka et al. | |
| 6,670,330 B1 | 12/2003 | Lampidis et al. | |
| 9,636,359 B2 | 5/2017 | Kenyon et al. | |
| 2004/0018987 A1 | 1/2004 | Hoffman et al. | |
| 2004/0167079 A1 | 8/2004 | Tidmarsh | |
| 2005/0026852 A1 | 2/2005 | Rustum et al. | |
| 2007/0031398 A1 | 2/2007 | Miller | |
| 2012/0251516 A1* | 10/2012 | Kenyon | A61K 31/095 424/94.2 |

FOREIGN PATENT DOCUMENTS

| | | |
|---|---|---|
| EP | 1 426 047 A1 | 6/2004 |
| EP | 1 652 519 A1 | 5/2006 |
| KR | 2007-0012040 A | 1/2007 |
| RU | 2149021 C1 | 5/2000 |
| WO | 2004/062604 A2 | 7/2004 |
| WO | 2009/061051 A1 | 5/2009 |
| WO | WO 2011/047434 A1 | 4/2011 |
| WO | WO 2015/070828 A1 | 5/2015 |
| WO | 2016/020572 A1 | 2/2016 |
| WO | 2017/127892 A1 | 8/2017 |
| WO | 2017/177270 A1 | 10/2017 |

OTHER PUBLICATIONS

Kaiserová (Proenzyme therapy of sarcoma S-180 and melanoma B16-F10; 2013, RNDr. Thesis, The University of South Bohemia, České Budějovice, Czech Republic).*
Jiang et al (Acta Biochim Biophys Sin, 2016, 48(3): 229-237).*
Lobo et al (Annu Rev Cell Dev Biol, 2007, 23: 675-99).*
Dou et al (Cellular & Molecular Immunology, 2007, 4(6): 467-472).*
Kaiserova, P. et al., Proenzyme Therapy of Sarcoma S-180 and Melanoma B16-F10, Journal of Applied Biomedicine, 2014, vol. 12, No. 1, pp. 39-47.
Novak, J.F., Proenzyme Therapy of Cancer, Anticancer Research 2005, vol. 25, pp. 1157-1178.
Peran, M. et al., In Vitro Treatment of Carcinoma Cell Lines with Pancreatic (pro)enzymes suppresses the EMT programme and promotes cell differentiation, Cellular Oncology, 2013, vol. 36, No. 4, pp. 289-301.
International Search Report of International Application No. PCT/AU2017/050065, 3 pages.
Written Opinion of International Application No. PCT/AU2017/050065, 4 pages.
Beuth, et al., (Jun. 2001) "Impact of complementary oral enzyme application on the postoperative treatment results of breast cancer patients—results of an epidemiological multicentre retrolective cohort study", Cancer Chemotherapy and Pharmacology, 47(Suppl. 1):S45-S54.
Chabner, et al., (Jan. 1, 2005) "Chemotherapy and the war on cancer", Nature Reviews Cancer, 5:65-72.
Cohen, et al., (Nov. 5, 1999) "Oral Enzyme Therapy and Experimental Rat Mammary Tumor Metastasis", Life Sciences, 65(24):2603-2614.

(Continued)

*Primary Examiner* — Sean E Aeder
(74) *Attorney, Agent, or Firm* — Lee & Hayes, P.C.

(57) ABSTRACT

The present invention relates to compositions, methods, uses and kits for treating cancer. The present invention relates to methods for minimising the progression of cancer in a subject, the method comprising administering to the subject therapeutically effective amounts of chymotrypsinogen and trypsinogen, thereby minimising the progression of cancer in the subject. In particular, the methods provide a means for treating cancer by reducing the number of cancer stem cells in the subject.

12 Claims, 33 Drawing Sheets

Specification includes a Sequence Listing.

(56) References Cited

OTHER PUBLICATIONS

Dreyer, et al., (Dec. 1, 1955) "The Activation of Chymotrypsinogen Isolation and Identification of a Peptide Liberated during Activation", Journal of Biological Chemistry, 217(2):527-540.
Gonzalez, et al., (1999) "Evaluation of Pancreatic Proteolytic Enzyme Treatment of Adenocarcinoma of the Pancreas, With Nutrition and Detoxification Support", Nutrition and Cancer, 33(2):117-124.
Gura, (Nov. 7, 1997) "Systems for Identifying New Drugs are Often Faulty", Science, 278(5340):1041-1042.
Gurkoff, et al., (Apr. 1974) "Preliminary Study on the Effects of Combined Hydrolytic Enzyme Agents on Mouse Krebs-2 Carcinoma", Journal of the American Osteopathic Association, 73(8):672-673.
Jiang, et al., (Dec. 1999) "Selenium-Induced Inhibition of Angiogenesis in Mammary Cancer at Chemopreventive Levels of Intake", Molecular Carcinogenesis, 26(4):213-225.
Keller, et al., (1958) "The Proteins of Bovine Pancreatic Juice", The Journal of Biological Chemistry, 233(2):344-349.
Leipner, et al., (Apr. 2000) "Systemic Enzyme Therapy in Oncology Effect and Mode of Action", Drugs, 59(4):769-780.
Merchan, et al., (Oct. 2010) "Antiangiogenic Activity of 2-Deoxy-D-Glucose", Plos One, 5(10):e13699.
Peran, et al., (Oct. 25, 2017) "A Formulation of Pancreatic Pro-Enzymes Provides Potent Anti-Tumour Efficacy: A Pilot Study Focused on Pancreatic and Ovarian Cancer", Scientific Reports, 7(1):13998, pp. 1-15.
Popiela, et al., (Jun. 2001) "Influence of a Complementary Treatment with Oral Enzymes on Patients with Colorectal Cancers—an Epidemiological Retrolective Cohort Study", Cancer Chemotherapy and Pharmacology, 47(Suppl. 1):S55-S63.
Pyun, et al., (Jan. 1, 2008) "Capsiate, a Nonpungent Capsaicin-Like Compound, Inhibits Angiogenesis and Vascular Permeability via a Direct Inhibition of Src Kinase Activity", Cancer Research, 68(1):227-235.
Saruc, et al., (May 2004) "Pancreatic Enzyme Extract Improves Survival in Murine Pancreatic Cancer", Pancreas, 28(4):401-412.
Wald, et al., (Jul. 2001) "Mixture of Trypsin, Chymotrypsin and Papain Reduces Formation of Metastases and Extends Survival Time of C57BI6 Mice with Syngeneic Melanoma B16", Cancer Chemotherapy and Pharmacology, 47(Suppl. 1):S16-S22.
Wald, et al., (1998) "Polyenzyme Preparation Wobe-Mugos® Inhibits Growth of Solid Tumors and Development of Experimental Metastases in Mice", Life Sciences, 62(3):43-48.
Wald, et al., (Sep. 18, 1998) "Proteinases Reduce Metastatic Dissemination and Increase Survival Time in C57BI6 Mice with the Lewis Lung Carcinoma", Life Sciences, 63(17):237-43.
Novak et al. (2006) "Trypsin/chymotrypsin and Their Respective Zymogens Inhibit Tumor Growth in Vitro and in Vivo", Cancer Research, 47:2 pages.
Zumiya et al. (2012) "Chemoresistance is Associated with Cancer Stem Cell-like Properties and Epithelial-to-Mesenchymal Transition in Pancreatic Cancer Cells". Anticancer Research, vol. 32, pp. 3847-3854.
Ju et al. (2014) "Maintenance of the sternness in CD44+ HCT-15 and HCT-116 human colon cancer cells requires miR-203 suppression". Stem Cell Research, vol. 12, pp. 86-100.
Lugli et al. (Jul. 6, 2010) "Prognostic impact of the expression of putative cancer stem cell markers CD133, CD166, CD44s, EpCAM, and ALDHI in colorectal cancer" British Journal of Cancer, vol. 103, pp. 382-390.
Ozawa et al. (Jun. 12, 2014) "Prognostic significance of CD44 variant 2 upregulation in colorectal cancer". British Journal of Cancer, vol. 111, pp. 365-374.
Roy et al. (Jun. 2014) "Decreased Camptothecin Sensitivity of the Stem-Cell-Like Fraction of Caco2 Cells Correlates with an Altered Phosphorylation Pattern of Topoisomerase I". PLOS One, vol. 9(6), e99628, pp. 1-11.
Charafe-Jauffret et al. (Jan. 1, 2010) "Aldehyde Dehydrogenase 1-Positive Cancer Stem Cells Mediate Metastasis and Poor Clinical Outcome in Inflammatory Breast Cancer", Clinical Cancer Research, 16(1):22 pages.
Chikamatsu et al. (Mar. 2012, e-published on Apr. 5, 2011) "Resistance to Apoptosis-Inducing Stimuli in CD44+ Head and Neck Squamous Cell Carcinoma Cells", Head & Neck, 34(3):336-343.
Huang et al. (Apr. 15, 2009) "Aldehyde Dehydrogenase 1 is a Marker for Normal and Malignant Human Colonic Stem Cells (SC) and Tracks SC Overpopulation During Colon Tumorigenesis", Cancer Research, 69(8):18 pages.
Ramirez et al. (May 13, 2014) "HER2-Signaling Pathway, JNK and Erks Kinases, and Cancer Stem-Like Cells are Targets of Bozepinib", Oncotarget, 5(11): 3590-3606.
Reya et al. (Nov. 1, 2001) "Stem Cells, Cancer, and Cancer Stem Cells", Nature, 414(6859):105-111.
Siclari et al. (Oct. 27, 2010) "Targeting the Osteosarcoma Cancer Stem Cell", Journal of Orthopaedic Surgery and Research, 5:10 pages.
Tang (Jan. 17, 2012) "Understanding Cancer Stem Cell Heterogeneity and Plasticity", Cell Research, 22(3):457-472.
Yu et al., "Cancer stem cells", Int J Biochem Cell Biol, Dec. 2012;44(12):2144-51. doi: 10.1016/j.biocel.2012.08.022.

\* cited by examiner

Pancreatic CSC, BXPC3
Triple labelling: CD326 CD44 CxCR4

A. 1st Assay

B. 2nd Assay

E

F

A.

B.

C.

A.

B.

CANCER TREATMENT

FIELD OF THE INVENTION

The present invention relates to compositions, methods, uses and kits for treating cancer.

CROSS REFERENCE TO RELATED APPLICATIONS

This application is a National Stage Application, filed under 35 U.S.C. § 371, of International Application No. PCT/AU2017/050065 filed Jan. 27, 2017, which claims the benefit of priority to Spanish patent applications, P 201630112 filed Jan. 29, 2016 and P 201631662 filed Dec. 22, 2016, the entire contents of each of which are incorporated herein by reference.

INCORPORATION-BY-REFERENCE OF SEQUENCE LISTING

The contents of the text file named "028616_506N01_US_Sequence_Listing.txt", which was created on Jul. 26, 2018 and is 4,502 bytes is size, is hereby incorporated by reference in its entirety.

BACKGROUND OF THE INVENTION

Despite improvements in therapies for the treatment of cancer, the cancer mortality rate worldwide remains high and strategies to prevent cancer recurrence are still needed. Current therapeutic strategies against cancer frequently result in treatment failure, often due to the development of multiple malignancies and/or resistance to chemotherapy and radiotherapy.

Cancer stem cells (CSCs) are immortal tumour-initiating cells that have the capacity to self-renew and have pluripotent capacity (Reya et al., (2001). Nature 414:105-111). CSCs are found in multiple malignancies, including leukaemia and many solid tumours and, given their stem-cell like properties, are thought to be the basis for tumour initiation, development, metastasis and recurrence (Tang DG. Cell Res 2012; 22: 457-72).

CSCs represent only a small fraction of the cancer cells within a tumour and can remain quiescent for extended periods of time, thereby evading conventional therapies (e.g., chemotherapy and radiotherapy) that are targeted to highly proliferative cells (Chikamatsu et al., (2011) Head Neck. 34(3):336-43). Consequently, a priority for improving cancer treatment and reducing the risk of cancer relapse is to develop new strategies that selectively target CSC eradication while sparing normal stem cells.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In a first aspect, the present invention relates to a method of minimising the progression of cancer in a subject who has received a treatment for cancer, the method comprising administering to the subject therapeutically effective amounts of chymotrypsinogen and trypsinogen, thereby minimising the progression of cancer in the subject.

In a further aspect, the invention relates to a method of treating minimal residual disease in a subject who has received a treatment for cancer, the method comprising administering to the subject therapeutically effective amounts of chymotrypsinogen and trypsinogen, thereby treating minimal residual disease in a subject.

In a further aspect, the invention relates to a method of preventing minimal residual disease in a subject who is receiving a treatment for cancer, the method comprising administering to the subject therapeutically effective amounts of chymotrypsinogen and trypsinogen, thereby preventing minimal residual disease in a subject.

In a further aspect, the invention relates to a method of preventing recurrence of cancer in a subject who has received a treatment for cancer, the method comprising administering to the subject therapeutically effective amounts of chymotrypsinogen and trypsinogen, thereby preventing recurrence of cancer in the subject.

In a further aspect, the invention relates to a method of preventing or inhibiting metastasis of cancer in a subject, the method comprising administering to the subject therapeutically effective amounts of chymotrypsinogen and trypsinogen, thereby preventing metastasis of cancer in the subject.

In yet a further aspect, the invention relates to a method of sensitising a subject for subsequent treatment for cancer, the method comprising administering a therapeutically effective amount of chymotrypsinogen and trypsinogen to the subject before the subject receives treatment for cancer, thereby sensitising the subject for subsequent treatment for cancer.

In yet a further aspect, the invention relates to a method of preventing cancer in a subject, the method comprising administering a therapeutically effective amount of chymotrypsinogen and trypsinogen to the subject, wherein the subject is considered at risk of the development of cancer.

The invention also relates to a method of delaying the onset of cancer in a subject, the method comprising administering therapeutically effective amounts of chymotrypsinogen and trypsinogen, thereby delaying the onset of cancer in the subject.

In any method or use of the invention, the number of cancer stem cells in the subject may be reduced or prevented from increasing in number. Alternatively, the cancer stem cells may be differentiated. Identification of cancer stem cells or the extent of differentiation may be determined by any method described herein using markers as described herein, particularly Table 1.

Further provided are compositions for minimising the progression of cancer in a subject who has received a treatment for cancer, comprising chymotrypsinogen and trypsinogen.

In another aspect, the invention provides compositions for treating minimal residual disease in a subject who has received a treatment for cancer, comprising chymotrypsinogen and trypsinogen.

In still a further aspect, the invention provides compositions for preventing metastasis of cancer in a subject, comprising chymotrypsinogen and trypsinogen.

The invention also contemplates the use of chymotrypsinogen and trypsinogen in the manufacture of a medicament for minimising the progression of cancer in a subject, wherein the subject has previously received a treatment for cancer.

Still further, the invention contemplates the use of chymotrypsinogen and trypsinogen in the manufacture of a medicament for treating minimal residual disease in a subject who has received a treatment for cancer.

In any method of the invention described herein, the method may further include the step of identifying the presence of cancer stem cells in the subject.

In any method of the invention described herein, the method may further include the step of providing a subject who has received a treatment for cancer. Further, the subject may not have detectable cancer at the time that the chymotrypsinogen and trypsinogen is administered, for example, the cancer may have substantially diminished in size, mass or other physical measure as a consequence of the prior treatment at the time that the chymotrypsinogen and trypsinogen is administered to the subject.

The invention also relates to a method of treating cancer in a subject, the method comprising the steps of:
- identifying the presence of cancer stem cells in the subject; and
- administering therapeutically effective amounts of chymotrypsinogen and trypsinogen, thereby treating cancer in the subject.

The invention also relates to a method of preventing cancer in a subject, the method comprising the steps of:
- identifying the presence of cancer stem cells in the subject who has not been diagnosed as having cancer; and
- administering therapeutically effective amounts of chymotrypsinogen and trypsinogen,
- thereby preventing cancer in the subject.

The invention also relates to a method of preventing cancer in a subject, the method comprising the steps of:
- providing a subject identified as being at risk of developing cancer but who has not been diagnosed as having cancer; and
- administering therapeutically effective amounts of chymotrypsinogen and trypsinogen,
- thereby preventing cancer in the subject.

The invention also relates to a method of delaying the onset of cancer in a subject, the method comprising the steps of:
- providing a subject at risk of cancer but who has not been diagnosed as having cancer; and
- administering therapeutically effective amounts of chymotrypsinogen and trypsinogen,
- thereby delaying the onset of cancer in the subject.

In any embodiment of the present invention, a subject or individual who is considered at risk of cancer may be an individual who has a family history of cancer, have one or more biomarkers associated with cancer, including having cancer stem cells.

As such, the present invention also relates to a method of preventing cancer in a subject, the method comprising the steps of:
- identifying the presence of cancer stem cells in the subject, wherein the subject has not been diagnosed as having cancer; and
- administering therapeutically effective amounts of chymotrypsinogen and trypsinogen,
- thereby preventing cancer in the subject.

The invention also relates to a method of preventing cancer in a subject, the method comprising the steps of:
- identifying the presence of cancer stem cells in the subject who is at risk of developing cancer but has not been diagnosed as having cancer; and
- administering therapeutically effective amounts of chymotrypsinogen and trypsinogen,
- thereby preventing cancer in the subject.

The invention also relates to a method of delaying the onset of cancer in a subject, the method comprising the steps of:
- identifying the presence of cancer stem cells in the subject who is at risk of developing cancer but has not been diagnosed as having cancer; and
- administering therapeutically effective amounts of chymotrypsinogen and trypsinogen,
- thereby delaying the onset of cancer in the subject.

In a further embodiment, the invention relates to a method of preventing the recurrence of cancer in a subject, the method comprising the steps of:
- providing an individual who has received a treatment for cancer; and
- administering therapeutically effective amounts of chymotrypsinogen and trypsinogen,
- thereby preventing the recurrence of cancer in the subject.

In a further embodiment, the invention relates to a method of preventing metastasis of cancer in a subject, the method comprising the steps of:
- providing an individual who is to receive a treatment for cancer, who is receiving a treatment of cancer, or who has received a treatment for cancer; and
- administering therapeutically effective amounts of chymotrypsinogen and trypsinogen,
- thereby preventing metastasis of cancer in the subject.

Yet further, the invention relates to a method of delaying the recurrence of cancer in a subject, the method comprising the steps of:
- providing an individual who has received a treatment for cancer; and
- administering therapeutically effective amounts of chymotrypsinogen and trypsinogen,
- thereby delaying the recurrence of cancer in the subject.

Still further, the invention relates to a method of delaying the onset of cancer in a subject, the method comprising the steps of:
- providing an individual who is at risk of the development of cancer; and
- administering therapeutically effective amounts of chymotrypsinogen and trypsinogen,
- thereby delaying the onset of cancer in the subject.

Preferably, identifying the presence of cancer stem cells occurs at the site of an existing tumour or at the site of therapeutic intervention. Typically, the therapeutic intervention is surgical resection, chemotherapy or radiotherapy.

Preferably, cancer stem cells are identified using any one or more markers as described herein such as in Table 1. For example, pancreatic-specific CSC markers include CD326, CD44 and CxCR4 and colon-specific CSC markers: CD326 and CD44 and analysed by immunofluorescence or flow cytometry.

The invention also relates to a method of treating cancer in a subject, the method comprising the steps of:
- identifying the presence of cancer stem cells in the subject by determining the presence of any one or more of the cell surface markers in Table 1; and
- administering therapeutically effective amounts of chymotrypsinogen and trypsinogen,
- thereby treating cancer in the subject.

The invention also relates to a method of treating colon cancer in a subject, the method comprising the steps of:
- identifying the presence of colon cancer stem cells in the subject by determining the presence of any one or more of the cell surface markers CD326 and CD44; and
- administering therapeutically effective amounts of chymotrypsinogen and trypsinogen,
- thereby treating colon cancer in the subject.

The invention also relates to a method of preventing colon cancer in a subject, the method comprising the steps of:

identifying the presence of colon cancer stem cells in the subject by determining the presence of any one or more of the cell surface markers CD326 and CD44; and administering therapeutically effective amounts of chymotrypsinogen and trypsinogen, thereby preventing colon cancer in the subject.

The invention also relates to a method of delaying the onset of colon cancer in a subject, the method comprising the steps of:

identifying the presence of colon cancer stem cells in the subject by determining the presence of any one or more of the cell surface markers CD326 and CD44; and administering therapeutically effective amounts of chymotrypsinogen and trypsinogen, thereby delaying the onset of colon cancer in the subject.

The invention also relates to a method of preventing the recurrence of colon cancer in a subject, the method comprising the steps of:

providing a subject who has received a treatment for colon cancer; and administering therapeutically effective amounts of chymotrypsinogen and trypsinogen, thereby preventing the recurrence of colon cancer in the subject.

The invention also relates to a method of sensitising a subject to a treatment for colon cancer, the method comprising the steps of:

providing a subject who is to receive a treatment for colon cancer and administering therapeutically effective amounts of chymotrypsinogen and trypsinogen, thereby sensitising the subject for a treatment for colon cancer.

The invention also relates to a method of treating pancreatic cancer in a subject, the method comprising the steps of:

identifying the presence of pancreatic cancer stem cells in the subject by determining the presence of any one or more of the cell surface markers CD326, CD44 and CxCR4; and administering therapeutically effective amounts of chymotrypsinogen and trypsinogen, thereby treating pancreatic cancer in the subject.

The invention also relates to a method of preventing pancreatic cancer in a subject, the method comprising the steps of:

identifying the presence of pancreatic cancer stem cells in the subject by determining the presence of any one or more of the cell surface markers CD326, CD44 and CxCR4; and administering therapeutically effective amounts of chymotrypsinogen and trypsinogen, thereby preventing pancreatic cancer in the subject.

The invention also relates to a method of delaying the onset of pancreatic cancer in a subject, the method comprising the steps of:

identifying the presence of pancreatic cancer stem cells in the subject by determining the presence of any one or more of the cell surface markers CD326, CD44 and CxCR4; and administering therapeutically effective amounts of chymotrypsinogen and trypsinogen, thereby delaying the onset of pancreatic cancer in the subject.

The invention also relates to a method of preventing the recurrence of pancreatic cancer in a subject, the method comprising the steps of:

providing a subject who has received a treatment for pancreatic cancer; and administering therapeutically effective amounts of chymotrypsinogen and trypsinogen, thereby preventing the recurrence of pancreatic cancer in the subject.

The invention also relates to a method of sensitising a subject to a treatment for pancreatic cancer, the method comprising the steps of:

providing a subject who is to receive a treatment for pancreatic cancer and administering therapeutically effective amounts of chymotrypsinogen and trypsinogen, thereby sensitising the subject for a treatment for pancreatic cancer.

The present invention also relates to a composition comprises or consists of chymotrypsinogen and trypsinogen for use in (a) minimising the progression of cancer in a subject who has received a treatment for cancer, (b) treating minimal residual disease in a subject who has received a treatment for cancer, or (c) of sensitising a subject for subsequent treatment for cancer. Typically, the composition further comprises a pharmaceutically acceptable diluent, excipient or carrier.

The invention also provides a kit minimising the progression of cancer in a subject who has received a treatment for cancer, comprising at least one dosage unit, wherein the dosage unit comprises chymotrypsinogen, trypsinogen and a pharmaceutically acceptable diluent, excipient or carrier. Optionally the kit also includes written instructions directing the user to administer a dosage unit of chymotrypsinogen according to a method of the invention described herein.

The invention also provides a kit of the invention when used in a method of the invention.

In any aspect of the invention, chymotrypsinogen and trypsinogen is administered in a weight ratio in the range of at or about 1:1 to at or about 10:1, at or about 4:1 to at or about 8:1, at or about 5:1 to at or about 7:1, or at about 6:1. Further, any composition described above has chymotrypsinogen and trypsinogen in a weight ratio in the range of at or about 1:1 to at or about 10:1, at or about 4:1 to at or about 8:1, at or about 5:1 to at or about 7:1, or at about 6:1.

In any aspect of the invention, chymotrypsinogen and trypsinogen is administered intravenously, subcutaneously or intramuscularly.

In any aspect of the invention, chymotrypsinogen and trypsinogen may be administered simultaneously or sequentially.

In any aspect of a method or use of the invention, the method or use further comprises the step of identifying a subject having, or at risk of developing, cancer. Preferably, the cancer is any one described herein.

In any aspect of the invention, the composition does not contain or the method or use does not administer, amylase.

In any aspect, embodiment or form of the invention described herein the amount of chymotrypsinogen administered may be greater than, or equal to, 1 mg/kg, 1.5 mg/kg, 2 mg/kg, 3.5 mg/kg, 5 mg/kg, 15 mg/kg, 20 mg/kg, 40 mg/kg, 45 mg/kg, 135 mg/kg, 250 mg/kg or 500 mg/kg.

In any aspect, embodiment or form of the invention described herein the amount of trypsinogen administered may be greater than, or equal to, 0.2 mg/kg, 0.25 mg/kg, 0.4 mg/kg, 0.6 mg/kg, 0.8 mg/kg, 2 mg/kg, 2.5 mg/kg, 3 mg/kg, 5 mg/kg, 7 mg/kg, 8 mg/kg, 20 mg/kg, 40 mg/kg or 80 mg/kg.

In any aspect, embodiment or form of the invention described herein the amount of chymotrypsinogen administered to a human may be greater than, or equal to, 0.1 mg/kg, 0.15 mg/kg, 0.25 mg/kg, 0.4 mg/kg, 1.2 mg/kg, 3.5 mg/kg, 10 mg/kg, 20 mg/kg or 40 mg/kg.

In any aspect, embodiment or form of the invention described herein the amount of trypsinogen administered to a human may be greater than, or equal to, 0.02 mg/kg, 0.03 mg/kg, 0.05 mg/kg, 0.06 mg/kg, 0.2 mg/kg, 0.6 mg/kg, 1.5 mg/kg, 3 mg/kg or 6 mg/kg.

Preferably, in any aspect, embodiment or form of the invention described herein the amount of chymotrypsinogen administered may be in the range of 1 mg/kg to 41 mg/kg, 1.5 mg/kg to 500 mg/kg, 2 mg/kg to 250 mg/kg, 3.5 mg/kg to 135 mg/kg, 5 mg/kg or 15 mg/kg to 45 mg/kg.

Preferably, in any aspect, embodiment or form of the invention described herein the amount of trypsinogen administered may be greater than 0.2 mg/kg to 7 mg/kg, 0.25 mg/kg to 80 mg/kg, 0.4 mg/kg to 40 mg/kg, 0.6 mg/kg to 20 mg/kg, 0.8 mg/kg to 8 mg/kg, or 2.5 mg/kg to 8 mg/kg.

In any composition of the invention above, the composition may be adapted to administer the relevant mg, or mg/kg, of chymotrypsinogen and trypsinogen to the subject.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
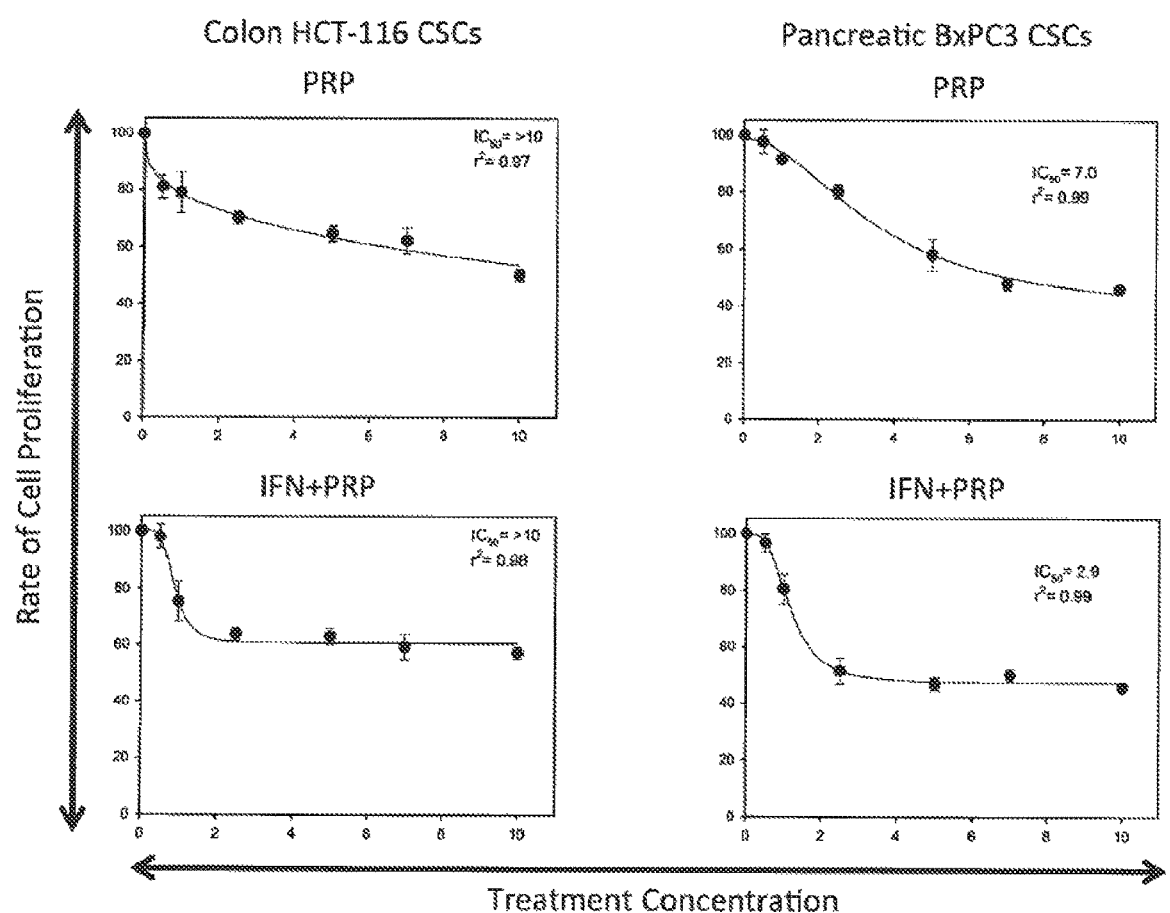
FIG. 1: MTT assay to determine $IC_{50}$ for Trypsinogen/Chymotrypsinogen. Rate of cell proliferation vs treatment concentration is shown for colon HCT-116 CSCs and pancreatic BxPC3 CSCs treated with varying concentrations of Trypsinogen/Chymotrypsinogen (1:6) or interferon alpha (IFN).

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

Current therapeutic strategies against cancer have severe limitations that frequently lead to treatment failure. Accumulated evidence suggests that the basis for these failures is due to the inability of current therapies to eliminate CSCs, meaning that patients are at risk of recurrence and metastasis. Moreover, there is evidence to suggest the CSC populations are more resistant to conventional cancer therapies than non-CSC populations. The elimination of CSCs is therefore critical in the treatment of malignant diseases.

The present invention is based on the surprising finding that by providing a combination of the pancreatic (pro) enzymes chymotrypsinogen and trypsinogen, it is possible to reduce the proliferation of CSCs, reduce the population of CSCs in a cancer cell population, inhibit sphere formation and reduce the expression of genes in CSCs associated with the transition from an epithelial to mesenchymal phenotype. Accordingly, the present inventors have identified a novel method for targeting of CSCs in a cancer cell population. This finding has important applications for the treatment of individuals who have previously received a treatment for cancer, particularly given that conventional cancer therapies often fail to eradicate target CSCs and there is a high likelihood of cancer recurrence, despite an apparently successful treatment of the cancer.

Accordingly, in a first aspect, the present invention provides a method for minimising the progression of cancer in a subject who has received a treatment for cancer, comprising administering to the subject therapeutically effective amounts of chymotrypsinogen and trypsinogen.

Chymotrypsinogen (which may be abbreviated to 'C' herein) is a proenzyme form of the enzyme chymotrypsin, which preferentially cleaves proteins at the following amino acids: tyrosine, tryptophan, phenylalanine and leucine. Chymotrypsin may be referred to or includes chymotrypsin A, chymotrypsin B (including B1 and B2 forms), chymotrypsin C, a-chymarophth, avazyme, chymar, chymotest, enzeon, quimar, quimotrase, α-chymar, α-chymotrypsin A, α-chymotrypsin. Chymotrypsin C can be formed from pig chymotrypsinogen C or from cattle subunit II of procarboxypeptidase A, and preferentially cleaves proteins at the following amino acids: tyrosine, tryptophan, phenylalanine, leucine, methionine, glutamine, and asparagine. Chymotrypsinogen includes chymotrypsinogen A, chymotrypsinogen B1 and chymotrypsinogen B2.

Trypsinogen (which may be abbreviated to 'T' herein) is a proenzyme form of trypsin, which preferentially cleaves proteins at arginine and lysine. Trypsin may be referred to or include α-trypsin, β-trypsin, cocoonase, parenzyme, parenzymol, tryptar, trypure, pseudotrypsin, tryptase, tripcellim, sperm receptor hydrolase β-trypsin can be formed from trypsinogen by cleavage of one peptide bond. Further peptide bond cleavages produce α and other iso-forms. Multiple cationic and anionic trypsins can be isolated from the pancreas of many vertebrates and from lower species including crayfish, insects (cocoonase) and microorganisms (*Streptomyces griseus*). In normal processes during digestion, inactive trypsinogen is activated by enteropeptidase present in intestinal mucosa to form the enzyme trypsin, which being a serine protease then acts to cleave the peptide bonds on the carboxyl side of basic amino acids/proteins.

As described above, the proenzyme form essentially provides an inactivated form of the enzyme that becomes activated in situ (e.g. by in vivo or in vitro activation). For example, activation of the proenzyme (conversion of proenzyme to active enzyme) may occur on contact with the CSC. It is believed that the proenzymes trypsinogen and chymotrypsinogen are selectively activated into the enzymes trypsin and chymotrypsin on contact with cancer cells and not on contact with healthy cells. The use of proenzymes reduces problems associated with providing, in situ, an active enzyme, such as undesirable reactions or inactivation of the enzyme before reaching an intended target of a cancer cell.

Without wishing to be bound by theory, the inventors believe that the combination of proenzymes chymotrypsinogen and trypsinogen acts to inhibit the production of growth factors and angiogenic stimulating factors that contribute to the tumour niche and consequently reduce the potential for tumour engrafting. In addition, the protease proenzymes induce the differentiation of CSCs, thereby reducing the total population of CSCs, and reducing the likelihood of recurrence or metastasis of the tumour. For example, the inventors have shown that chymotrypsinogen and trypsinogen, when provided to CSCs under appropriate conditions, reduce the proliferation of CSCs, reduce the population of CSCs in a cancer cell population, inhibit sphere formation and reduce the expression of genes in CSCs associated with the transition from an epithelial to mesenchymal phenotype. Given this, the use of chymotrypsinogen and trypsinogen has particular utility in minimising the progression, recurrence or metastasis of cancer in subjects who have received a treatment for cancer, particularly given that conventional cancer treatments typically do not target or minimise CSCs.

As used herein, "minimising the progression of cancer" means treating the subject so as to prevent or delay the recurrence or metastasis of a tumour. Minimising the progression of cancer includes preventing or delaying the recurrence of cancer, following a treatment of cancer. The recurrence that is being prevented includes a recurrence for example, in the tumour bed, following surgical excision. Alternatively, recurrence includes metastasis of the cancer in another part of the body. The terms "preventing recurrence" and "preventing relapse" as used herein, are interchangeable.

The present invention also includes methods of preventing the development of cancer in an individual. For example the individual for whom prevention of cancer is required may be considered to be at risk of developing cancer, but does not yet have detectable cancer. An individual at risk of the development of cancer may be an individual with a family history of cancer, and/or an individual for whom genetic testing or other testing indicates a high risk or high likelihood of the development of cancer. The individual may have cancer stem cells but does not yet have any detectable tumours. It will be understood that methods of preventing the development of cancer include methods of delaying the onset of cancer in a subject.

The treatment previously received by the subject can be any conventional cancer treatment, including chemotherapy, radiotherapy, immunotherapy and/or surgical excision of the tumour. In one embodiment, the treatment received by the subject is surgical excision of the tumour. In another embodiment, for example in the treatment of non-solid tumours, the subject has received chemotherapy, radiotherapy or immunotherapy, or a combination thereof. In yet a further embodiment, the subject has received surgical, chemotherapeutic and radiotherapeutic intervention prior to being administered chymotrypsinogen and trypsinogen in accordance with the methods of the instant invention. Any method to reduce the bulk or mass of a tumour is contemplated as a treatment previously received by the subject.

The subject who has received the treatment for cancer may be in partial or complete remission. In other words, the subject, having received a treatment for cancer, as described above, may have a 50% or greater reduction in the measurable parameters of tumour growth as may be found on physical examination, radiologic study, or by biomarker levels from a blood or urine test. Alternatively, where the subject is in complete remission, there is a complete disappearance of all detectable manifestations of disease, such that the subject does not have any detectable signs of cancer. The subject may have substantially undetectable signs of cancer. A cancer that is "substantially undetectable" generally refers to a circumstance where therapy has depleted the size, volume or other physical measure of a cancer so that using relevant standard detection techniques such as in vivo imaging, the cancer, as a consequence of the therapy, is not clearly detectable.

A key limitation of conventional cancer therapies is that even after surgical excision of the tumour, and adjuvant therapies (such as chemotherapy), there is likely to be minimal residual disease present. Minimal residual disease (MRD) refers to the small number of cancer cells that remain in a patient following treatment. Typically, these cells are difficult to detect or cannot be detected at all, such that the patient is said not to have any detectable cancer. However, MRD is a major cause of cancer relapse and the presence of CSCs even after extensive treatment, is thought to be the key contributor to MRD.

Accordingly, the present invention provides a method of treating or preventing minimal residual disease in a subject who has received a treatment for cancer, comprising administering to the subject therapeutically effective amounts of chymotrypsinogen and trypsinogen.

The objective or outcome of treatment with chymotrypsinogen and trypsinogen may be to reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder.

Efficacy of treatment can be measured by assessing the duration of survival, time to disease progression, the response rates (RR), duration of response, and/or quality of life.

In one embodiment, the method is particularly useful for delaying disease progression.

In one embodiment, the method is particularly useful for extending survival of the subject, including overall survival as well as progression free survival.

In one embodiment, the method is particularly useful for providing a complete response to therapy whereby all signs of cancer in response to treatment have disappeared. This does not always mean the cancer has been cured.

In one embodiment, the method is particularly useful for providing a partial response to therapy whereby there has been a decrease in the size of one or more tumors or lesions, or in the extent of cancer in the body, in response to treatment.

The methods of the present invention also include targeted treatment of CSCs before a subject receives a conventional treatment for cancer. The skilled person will appreciate that this approach has particular application for haematologic cancers, where it is not possible to surgically excise a tumour. As such, the invention provides a method of sensitising a subject prior to treatment for cancer, the method comprising administering a therapeutically effective amount of chymotrypsinogen and trypsinogen to the subject before the subject receives treatment for cancer.

Still further, the methods of the present invention also include targeted treatment of CSCs at the same time as a subject receives a conventional treatment for cancer. As such, the invention provides a method of further treating a subject for cancer, including preventing the likelihood of minimal residual disease at the completion of treatment or delaying or preventing the recurrence of cancer, the method comprising administering a therapeutically effective amount of chymotrypsinogen and trypsinogen to the subject concurrently with the conventional treatment for cancer.

Identification of cancer stem cells may be by detection of one or more markers. Exemplary markers are shown Table 1 below.

| Tumor type | Phenotype of CSCs markers |
|---|---|
| Leukemia | $CD34^+CD38^-HLA\text{-}DR\text{-}CD71^-CD90^-CD117^-CD123^+$ |
| Breast cancer | $ESA^+CD44^+CD24^{-/low}Lineage^-, ALDH\text{-}1^{high}$ |
| Liver cancer | $CD133^+, CD49f^+, CD90^+$ |
| Brain cancer | $CD133^+, BCRP1^+, A2B5^+, SSEA\text{-}1^+$ |
| Lung cancer | $CD133^+, ABCG2^{high}$ |
| Colon cancer | $CD133^+, CD44^+, CD166^+, EpCAM^+, CD24^+$ or $CD326^+$ and $CD44^+$ |
| Multiple myeloma | $CD138^-$ |
| Prostate cancer | $CD44^+, \alpha 2\beta 1^{high}, CD133^+$ |
| Pancreatic | $CD133^+, CD44^+, EpCAM^+, CD24^+$ or $CD326^+, CD44^+$ and $CxCR4^+$ |
| Melanoma | $CD20^+$ |
| Head and neck cancer | $CD44^+$ |

Cancer stem cells may be isolated from a tissue or sample using any method described herein. Cancer stem cells from a sample of the tumour or tumour stroma may be identified by sectioning the at least part of the sample, labelled (preferably immunolabelled) for any one or more cancer stem cells markers and analysed by immunofluorescence.

The "subject" includes a mammal. The mammal may be a human, or may be a domestic, zoo, or companion animal. While it is particularly contemplated that the methods of the invention are suitable for medical treatment of humans, they are also applicable to veterinary treatment, including treatment of companion animals such as dogs and cats, and domestic animals such as horses, cattle and sheep, or zoo animals such as felids, canids, bovids, and ungulates. A subject may be afflicted with cancer or other disorder, or may not be afflicted with cancer or other disorder (i.e., free of detectable disease).

The typical body weight of a human subject may be greater than, or equal to, 60, 65, 70, 75, 80, 85, 90, 95, 100, 105 or 110 kg.

The term "therapeutically effective amount" refers to an amount of composition, or agent or compound in the composition, capable of minimising the progression of, treating, preventing recurrence of or ameliorating cancer or the spread (metastasis) thereof. A therapeutically effective amount may be determined empirically and in a routine manner in relation to treating cancer, and will result in increased life expectancy.

As described herein, methods of the invention include minimising the progression, preventing the recurrence of or treating minimal residual disease associated with neoplasms and related conditions, cancers, tumours, malignant and metastatic conditions. Tissues and organs associated with solid tumours and metastases which can be treated with a method or pharmaceutical composition of the invention include, but are not limited to, biliary tract, bladder, blood, brain, breast, cervix, colon, endometrium, oesophagus, head, neck, kidney, larynx, liver, lung, medulla, melanin, ovarian, pancreas, prostate, rectum, renal, retina, skin, stomach, testes, thyroid, urinary tract, and uterus.

The methods and pharmaceutical compositions of the invention are useful for minimising the progression including preventing recurrence of cancers and metastatic carcinomas of the following types: pancreatic cancer, oesophageal cancer, colon cancer, bowel cancer, prostate cancer, ovarian cancer, stomach cancer, breast cancer, malignant melanoma, neuroblastoma or lung cancer. Preferably, the cancer is pancreatic cancer, colon cancer or ovarian cancer. More preferably, the cancer is pancreatic cancer.

The methods and pharmaceutical compositions of the invention may provide a multiple effect approach to treating cancer, for example by increasing apoptosis in tumour cells, increasing cell-to-cell adhesion, differentiation and immunogenicity (targeting and removal by immune system). It is therefore beneficial to conduct treatment in the absence of any other treatments that may suppress or harm the immune system.

In addition to providing methods of treatment, it will be appreciated that the instant invention includes the use of therapeutically effective amounts of chymotrypsinogen and trypsinogen in the manufacture of medicament for minimising the progression of cancer in a subject who has received a treatment for cancer.

In further embodiments, the use includes use of chymotrypsinogen and trypsinogen in the manufacture of a medicament for treating minimal residual disease in a subject, or for sensitising a subject before they receive a treatment for cancer.

The methods of the instant invention involve the administration of chymotrypsinogen and trypsinogen to a subject in need thereof.

The trypsinogen and chymotrypsinogen used in any aspect of the invention may be isolated, purified, substantially purified, recombinant or synthetic.

The proenzymes trypsinogen and chymotrypsinogen may be precursors of the enzymes selected from chymotrypsin classes 3.4.21.1 or 3.4.21.2 or trypsin from class 3.4.21.4, or selected from any other suitable source (classes grouped according to the classification of the Nomenclature Committee of the International Union of Biochemistry and Molecular Biology). These enzymes are commercially available and may be of human, bovine or porcine origin.

In certain aspects of the invention, the chymotrypsinogen and trypsinogen may be administered simultaneously or sequentially. When administered simultaneously, the chymotrypsinogen and trypsinogen can be included in the same pharmaceutical composition. When combined in the same pharmaceutical formulation, the weight ratio of chymotrypsinogen:trypsinogen may be in the range of between 1:1 to at or about 10:1, at or about 4:1 to at or about 8:1, at or about 5:1 to at or about 7:1, or at about 6:1. In one embodiment, the weight ratio of chymotrypsinogen:trypsinogen is in the range of between 5:1 to 7:1, preferably 6:1.

In one aspect, the pharmaceutical formulations of the instant invention comprise only chymotrypsinogen and trypsinogen as active agents. In alternative embodiments, additional active agents are included in the composition. For example, in addition to the pancreatic proenzymes chymotrypsinogen and trypsinogen, the compositions may include other known therapies for cancer treatment.

The pharmaceutical compositions of the invention may be formulated, for example, by employing conventional solid or liquid vehicles or diluents, as well as pharmaceutical additives of a type appropriate to the mode of desired administration (for example, excipients, binders, preservatives, stabilizers, flavours, etc.) according to techniques such as those well known in the art of pharmaceutical formulation.

The pharmaceutical compositions of the invention, and preparations or formulations thereof may be prepared by admixing together the components of the composition, including chymotrypsinogen and trypsinogen. The admixing may be performed sequentially or simultaneously.

The pharmaceutical compositions of the invention may conveniently be presented in dosage unit form and may be prepared by any of the methods well known in the art of pharmacy. All methods include the step of bringing the active agents and/or protease proenzyme into association with the carrier which constitutes one or more accessory ingredients. In general, the pharmaceutical compositions are prepared by uniformly and intimately bringing the active agents and/or protease proenzymes into association with a liquid carrier or a finely divided solid carrier or both, and then, if necessary, shaping the product into the desired formulation. The active agents and/or protease proenzymes are provided in a dosage unit form in an amount sufficient to produce the desired effect upon the process or condition of diseases after single or repeated administration.

The pharmaceutical compositions of the invention may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the protease proenzyme and active agent of the first and second aspects in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the protease proenzyme and active agent of the first and second aspects are mixed with an inert solid diluent, for example, calcium carbonate, calcium phosphate or kaolin, or as soft gelatin capsules wherein the protease proenzyme and active agent of the first and second aspects are mixed with water or an oil medium, for example peanut oil, liquid paraffin, or olive oil.

Aqueous suspensions contain the active agent and protease proenzyme in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active agent and protease proenzyme in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These may be preserved by the addition of an anti-oxidant such as ascorbic acid.

Dispersible powders and granules suitable for preparation of an aqueous suspension by the addition of water provide the protease proenzyme and active agent of the first and second aspects in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxy ethylene sorbitan monooleate. The emulsions may also contain sweetening and flavouring agents.

Syrups and elixirs may be formulated with sweetening agents, for example glycerol, propylene glycol, sorbitol or sucrose. They may also contain a demulcent, a preservative and flavouring and colouring agents.

The pharmaceutical compositions of invention may be in the form of a sterile injectable aqueous or oleagenous suspension. This suspension may be formulated according to the known art using those suitable dispersing or wetting agents and suspending agents which have been mentioned above. The pharmaceutical compositions of the first and second aspects may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In a particular embodiment, the pharmaceutical compositions of the invention are formulated as suppositories for rectal administration of the drug. These formulations can be prepared by mixing the protease proenzyme and active agent of the first and second aspects with a suitable non-irritating excipient which is solid at ordinary temperatures but liquid at the rectal temperature and will therefore melt in the rectum to release the drug. Such materials include cocoa butter and polyethylene glycols. Rectal administration may be used to eliminate entero-hepatic first pass effect in the gastrointestinal tract related to oral administration of enzymes.

The pharmaceutical compositions of the invention, may also be formulated in liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolisable lipid capable of forming liposomes can be used. The liposome formulation may contain stabilisers, preservatives, excipients and the like. The preferred lipids are the phospholipids and phosphatidyl cholines, both natural and synthetic. Methods to form liposomes are known in the art.

The pharmaceutical compositions of the invention, may be included in a container, pack, or dispenser together with instructions for administration. The protease proenzymes and active agents, and optionally additional active agent, of the pharmaceutical composition may be provided as separated components in the container, pack, or dispenser, to be taken separately or together at the same or different time in a use or method of the invention described herein.

An appropriate dosage level for the pharmaceutical compositions of the invention will generally be about 0.01 to 500 mg per kg patient body weight per day which can be administered in single or multiple doses. It may be about 0.1 to about 250 mg/kg per day; or about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05-0.5, 0.5-5 or 5-50 mg/kg per day.

For oral administration, the pharmaceutical compositions may be provided in the form of tablets containing 1.0-4000 milligrams of the protease proenzyme particularly 1.0, 5.0, 10.0, 15.0, 20.0, 25.0, 50.0, 75.0, 100.0, 150.0, 200.0, 250.0, 300.0, 400.0, 500.0, 750.0, 1000, 1500, 2000, 2500, 3000, 3500, and 4000 milligrams of the protease proenzymes for the symptomatic adjustment of the dosage to the patient to be treated. The pharmaceutical compositions as described herein may be administered on a regimen of 1 to 4 times per day, once or twice per day, or once daily, with reduced requirements of administration generally leading to greater compliance.

The dosage may vary widely depending on whether a single administration form of the composition is given. A suitable single administration for an embodiment of the pharmaceutical compositions as described herein may comprise:
Trypsinogen in an amount of between 1-100 mg, particularly 2-50 mg, more particularly (in mg) 1.0, 2.5, 5.0, 7.5, 10.0, 15.0, 20.0, 25.0, 30.0, 40.0, 50.0; and
Chymotrypsinogen in an amount of between 1-100 mg, particularly 2-50 mg, more particularly (in mg) 1.0, 2.5, 5.0, 7.5, 10.0, 15.0, 20.0, 25.0, 30.0, 40.0, 50.0.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Suitable dosage levels for the various components (if present) of an embodiment of the pharmaceutical compositions as described herein, may comprise:
Chymotrypsinogen in an amount of at least 0.2 mg/kg, or in a range of 0.2-5 mg/kg, in a range of 0.5-2.0 mg/kg, or about 0.8 mg/kg;
Trypsinogen in an amount of less than 0.5 mg/kg, or in a range of 0.01-0.4 mg/kg, or in a range of 0.05-0.20 mg/kg, or about 0.1 mg/kg;

Suitable concentrations for the various components (if present) of the pharmaceutical compositions as described herein, which may be particularly effective if present at or near the surface of a tumour cell, may comprise:
Chymotrypsinogen in a concentration of at least 0.5 mg/ml, or in a range of 1-2 mg/ml;
Trypsinogen in a concentration of less than 0.25 mg/ml, or in a range of 0.1-0.2 mg/ml;

The pharmaceutical compositions of the invention may be administered by any suitable means, for example, orally, such as in the form of tablets, capsules, granules or powders; sublingually; buccally; parenterally, such as by subcutaneous, intravenous, intramuscular, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. They may, for example, be administered in a form suitable for immediate release or extended release, for example, by the use of devices such as subcutaneous implants, encapsulated spheroids or osmotic pumps.

In certain embodiments, it may be preferably to administer the chymotrypsinogen and trypsinogen directly to the tumour bed or surrounding tissues, for example following excision of the tumour mass. In alternative embodiments, the chymotrypsinogen and trypsinogen are provided as a systemic dose, which may be more suitable for haematologic cancers.

The above disclosure generally describes the present invention. A more complete understanding can be obtained by reference to the following specific examples which are provided herein for purposes of illustration only, and are not intended to limit the scope of the invention.

EXAMPLES

Example 1

A series of in vitro studies were performed to study the effect of pancreatic proenzymes on proliferation and differentiation of CSCs.

A. Materials and Methods

Treatment Solutions and Control

A stock solution of 6 mg/ml of Chymotrypsinogen A and 1 mg/ml of Trypsinogen was prepared in PBS and stored at −20° C. until required. For each experiment, the stock solution was further diluted in culture medium to obtain the desired concentrations (see Table 2).

The anti-proliferative agent Interferon alpha (IFN) was used as a positive control at a concentration of 10000 UI/ml (INTRON® A Interferon alfa-2b).

A solution comprising Chymotrypsinogen A/Trypsinogen and IFN was also used to assess the combined effect of these reagents.

Cell Lines

The human pancreatic cancer cell lines BxPC3 and the human colon cancer cell line HCT-116 were obtained from American Type Culture Collection (ATCC) and maintained in RPMI 1640 Medium (for BxPC3) and Dulbecco's Modified Eagle Medium (for HCT-116) (Sigma-Aldrich) supplemented with 10% FBS.

The neuroblastoma cell line SK-N-SH (ATCC® HTB-11™ derived from neuroblastoma at metastatic site, bone marrow), was obtained from American Type Culture Collection (ATCC) and maintained in Eagle's Minimum Essential Medium supplemented with 10% FBS.

Cell passaging was performed using the trypsin replacement reagent TrypLE™ (Life Technologies).

Isolation of CSCs

BxPC3 pancreatic and HCT-116 colon cancer cells lines were grown in sphere forming medium in ultralow attachment plates. After 1 week, cells formed spheres and cancer stem-like cells were isolated using the ALDEFLUOR assay (StemCell Technologies) and the following markers: CD326, CD44 and CxCR4 (BxPC3) and CD326 and CD44 (for HCT-116) by fluorescence-activated cell sorting (FACS). The enriched subpopulation of CSCs were grown with a specific sphere-forming medium in ultralow attachment plates (Corning) as previously described in Charafe-Jauffret et al. (2010) Clin Cancer Res. 16(1):45-55. A similar method is described in Ramirez et al. (2014) Oncotarget, 5(11): 3590-3606.

Determination of Optimal Concentration of Trypsinogen/Chymotrypsinogen to Use in Downstream Assays Cell viability and proliferation was assessed using the MTT (3-(4,5-dimethylthiazolyl-2)-2,5-diphenyltetrazolium bromide) assay (Sigma). Briefly, cells ($2 \times 10^3$ cells/well) were seeded onto 96-well plates and incubated for 24 h and then treated with different solutions of Trypsinogen/Chymotrypsinogen, (see Table 2), IFN (control) and Trypsinogen/Chymotrypsinogen+IFN.

Three days later, treatment was repeated and cells were maintained for 3 additional days. Cells were maintained with the treatment for six days. Thereafter, cells were processed as follow, 10 μL of 2 mM MTT reagent was added to each well and cells were incubated at 37° C. for 4 hours. 100 μL detergent reagent was then added and cells were leaved at room temperature in the dark for 2 hours. Absorbance was recorded at 570 nm.

The $IC_{50}$ values were calculated from four parametric logistic curves by linear interpolation using Sigma Plot software. All of the experiments were plated in triplicate wells and were carried out at least twice.

The effect of anticancer drugs on cell viability and proliferation was assessed using the MTT (3-(4,5-dimethylthiazolyl-2)-2,5-diphenyltetrazolium bromide) assay (Sigma).

TABLE 2

Composition and concentration of treatment solutions

| Reagent | Treatment solution composition (mg/ml) | | | | | |
|---|---|---|---|---|---|---|
| | 1 | 2 | 3 | 4 | 5 | 6 |
| Chymotrypsinogen | 0.03 | 0.06 | 0.18 | 0.3 | 0.42 | 0.6 |
| Trypsinogen | 0.005 | 0.01 | 0.03 | 0.05 | 0.07 | 0.1 |

Cell Cycle Assay

Cell cycle distribution was measured in control and treated cells. After treatment, cells were collected in 15 ml tubes and washed once in cold 5 ml PBS. To fix the cells, cells were vortexed gently while 200 μl of 70% ethanol was added drop-by-drop and incubated at least for 20 min at 4° C. in the dark. After fixation the ethanol was discarded by centrifugation and cells were stained by addition of a solution containing PI and RNase and incubated in the dark for 45 minutes. The samples were immediately processed using a FACSAria III flow cytometer (Becton Dickinson, BD Biosciences, Franklin Lakes, N.J., USA) from the Scientific Instrumental Center (University of Granada). At least 10,000 events were collected in each final gated histogram. Cell cycle analysis was performed using Dean and Jett's algorithm (Multicycle, Phoenix Flow Systems, San Diego, Calif.).

CSC Marker Analysis by Flow Cytometry

ALDEFLUOR sorted BxPC3 pancreas and HCT-116 colon cancer cells were maintained for 6 days in culture and treated twice (day 2 and day 5) with Chymotrypsinogen: 0.42 mg/ml—Trypsinogen: 0.07 mg/ml.

Treated and untreated CSCs were disassociated using Tryple and washed twice in PBS supplemented with 1% bovine serum albumin (Sigma-Aldrich, St Louis, Mo.). The cell surface Fc receptor was blocked using IgG (Santa Cruz Biotechnology, Inc., Santa Cruz, Calif.) on ice for 15 min. Cells were stained for 30 min at 4° C. with anti-CD44-PE and anti-CD326 FITC and CxCR4-APC monoclonal antibodies (BD Biosciences, Franklin Lakes, N.J.). After washing, cells were analysed using a FACSAria III flow cytometer (Becton Dickinson, BD Biosciences, Franklin Lakes, N.J., USA) from the Scientific Instrumental Center (University of Granada).

CSC Sphere Formation in the Presence of Trypsinogen/Chymotrypsinogen

SK-N-SH cells were detached from the culture flask and cultured in CSC-enriched conditioned medium in presence of Trypsinogen/Chymotrypsinogen (0.07:0.42 mg/ml). Sphere formation was monitored every day under light microscopy, pictures were taken on day 6.

BxPC3 pancreatic and HCT-116 colon cancer cells lines were detached from the culture flask and cultured in CSC-enriched conditioned medium in presence of either:

1. Trypsinogen/Chymotrypsinogen (0.07 mg/ml:0.42 mg/ml)
2. Trypsinogen/Chymotrypsinogen (0.07 mg/ml:0.42 mg/ml) plus IFN (10000 UI/ml); or
3. IFN (10000 UI/ml)

Sphere formation was monitored every day under light microscopy, pictures were taken on day 2 and day 5.

For the secondary sphere-forming assay, cells from primary spheres were collected by centrifugation, then dissociated with Tryple and mechanically disrupted with a pipette. $10^3$ single cells were plated and resuspended in spheres culture medium in ultra-low adherence 24-well plates. Spheres>75 μM diameter were counted after 6 days by light microscopy.

Quantitative Real Time RT-PCR

Total RNA from the different cell lines was extracted from duplicate 80% confluent cultures using the TRIZOL reagent following the instructions of the manufacturer (Life Technologies). cDNA was synthesized by reverse transcription of total RNA using the Reverse Transcription System (Promega) and qRT-PCR assay was done using SYBR Green PCR Master Mix (Promega) and random primers. Each reaction was performed in triplicate from two cDNA dilutions. The comparative threshold cycle (Ct) method was used to calculate the amplification factor as specified by the manufacturer. Human GADPH was used as an internal standard to normalize variations in RNA quality in the quantities of input cDNA. Primer sequences for determining expression of genes associated with Epithelial-mesenchymal transition (EMT) are listed Table 3.

TABLE 3

Primer sequences used to determine expression levels of genes associated with Epithelial-mesenchymal transition (EMT)

| Gene | | Primer Sequence |
|---|---|---|
| SNAIL | Forward | 5' ACCCCACATCCTTCTCACTG 3' (SEQ ID NO: 1) |
| | Reverse | 5' TACAAAAACCCACGCAGACA 3' (SEQ ID NO: 2) |
| SLUG | Forward | 5' TGCGATGCCCAGTCTAGAAA 3' (SEQ ID NO: 3) |
| | Reverse | 5' TTCTCCCCGTGTGAGTTC 3' (SEQ ID NO: 4) |
| E-CADHERIN | Forward | 5' AATTCCTGCCATTCTGGGGA 3' (SEQ ID NO: 5) |
| | Reverse | 5' TCTTCTCCGCCTCCTTCTTC 3' (SEQ ID NO: 6) |
| N-CADHERIN | Forward | 5' TGAGCCTGAAGCCAACCTTA 3' (SEQ ID NO: 7) |
| | Reverse | 5' AGGTCCCCTGGAGTTTTCTG 3' (SEQ ID NO: 8) |
| VIMENTIN | Forward | 5' AGCTAACCAACGACAAAGCC 3' (SEQ ID NO: 9) |
| | Reverse | 5' TCCACTTTGCGTTCAAGGTC 3' (SEQ ID NO: 10) |
| OCT4 | Forward | 5' CACCATCTGTCGCTTCGAGG 3' (SEQ ID NO: 11) |
| | Reverse | 5' AGGGTCTCCGATTTGCATATCT 3' (SEQ ID NO: 12) |

TABLE 4

Primer sequences used to determine expression levels of genes associated with pluripotency

| Gene | | Primer Sequence |
|---|---|---|
| KLF4 | Forward | 5' CGAACCCACACAGGTGAGAA 3' (SEQ ID NO: 13) |
| | Reverse | 5' TACGGTAGTGCCTGGTCAGTTC 3' (SEQ ID NO: 14) |
| SOX2 | Forward | 5' CAAGATGCACAACTCGCAGA 3' (SEQ ID NO: 15) |
| | Reverse | 5' CATGAGCGTCTTGGTTTTCC 3' (SEQ ID NO: 16) |
| NANOG | Forward | 5' TCCTGAACCTCAGCTACAAAC 3' (SEQ ID NO: 17) |
| | Reverse | 5' GCGTCACACCATTGCTATTC 3' (SEQ ID NO: 18) |
| C-MYC | Forward | 5' GAGTCTGGATCACCTTCTGCTG 3' (SEQ ID NO: 19) |
| | Reverse | 5' AGGATAGTCCTTCCGAGTGGAG 3' (SEQ ID NO: 20) |
| CD133 | Forward | 5' CAGAATAATAAACAGCAGCCC 3' (SEQ ID NO: 21) |
| | Reverse | 5' GATTATGACAAGCCAGAAACT 3' (SEQ ID NO: 22) |

Microarray Studies

The expression of genes involved in epithelial to mesenchymal transition (EMT) or related to CSC expression was analysed with RT² Profiler™ PCR Arrays (Qiagen) processed following manufacturer's instructions.

A set of controls present on each array enabled data analysis using the ΔΔCT method of relative quantification and assessment of reverse transcription performance, genomic DNA contamination, and PCR performance.

The RT² Profiler™ PCR Arrays used were:

1. The Human Epithelial to Mesenchymal Transition (EMT) RT² Profiler™ PCR Array, that profiles the expression of 84 key genes that either change their expression during EMT or regulate gene expression changes during EMT. The array includes cell surface receptor, extracellular matrix, and cytoskeletal genes mediating cell adhesion, migration, motility, and morphogenesis; genes controlling cell differentiation, development, growth, and proliferation; as well as signal transduction and transcription factor genes that cause EMT and all of its associated processes.

2. The Human Cancer Stem Cells RT² Profiler PCR array profiles the expression of 84 genes linked to cancer stem cells (CSCs). The genes profiled with this array include CSC molecular markers and genes regulating CSC proliferation, self-renewal, and pluripotency to help ensure the stability of CSC isolates in culture. Also included are genes involved in CSC asymmetric cell division, migration and metastasis, and relevant signal transduction pathways.

B. Results $IC_{50}$ Determination by MTT Assay

The MTT assay is based on the reduction of MTT (3-(4,5-dimethylthiazolyl-2)-2,5-diphenyltetrazolium bromide) by metabolically active cells. The resulting intracellular purple formazan can be solubilized and quantified by spectrophotometric means.

FIG. 1 shows the response curves at various concentrations of Trypsinogen/Chymotrypsinogen and Trypsinogen/Chymotrypsinogen+IFN.

The data show that the optimal concentration of Trypsinogen/Chymotrypsinogen A is Trypsinogen 0.07 mg/ml and Chymotrypsinogen A 0.42 mg/ml (a 1:6 ratio), however ratios of between 1:1 to about 1:10 Trypsinogen/Chymotrypsinogen are also expected to reduce cell metabolic activity and inhibit cell proliferation. These concentrations of Trypsinogen 0.07 mg/ml and Chymotrypsinogen A 0.42 mg/ml were used in subsequent experiments and is referred to as "PRP" in subsequent experiments. The data also show that the combination of IFN and Trypsinogen/Chymotrypsinogen significantly enhances the antiproliferative effect of Trypsinogen/Chymotrypsinogen.

Cell Cycle Assay

Cell cycle assays were performed on cells that were grown under sphere formation conditions (CSCs) and on adherent cells (non-CSCs). Cells were treated once with IFN (10000 UI/ml), PRP (Trypsinogen/Chymotrypsinogen 0.07 mg/ml:0.42 mg/ml) and PRP+IFN (Trypsinogen/Chymotrypsinogen 0.07 mg/ml:0.42 mg/ml plus IFN 10000 UI/ml) and after 4 days processed for cell cycle assay.

The numbers of cells in G1/G0 phase were similar in pancreatic CSCs and non-CSCs (72.8% vs 82.4%) and in colon CSCs and non-CSCs (77.1% vs 79.9%). Treatment with PRP did not appear to change the number of cells in G1/G0 in pancreatic CSC (82.4% vs 89.4%) or in colon CSC (79.9% vs 78.8%) (FIG. 2a-c; FIG. 3a-c).

Figure 2:
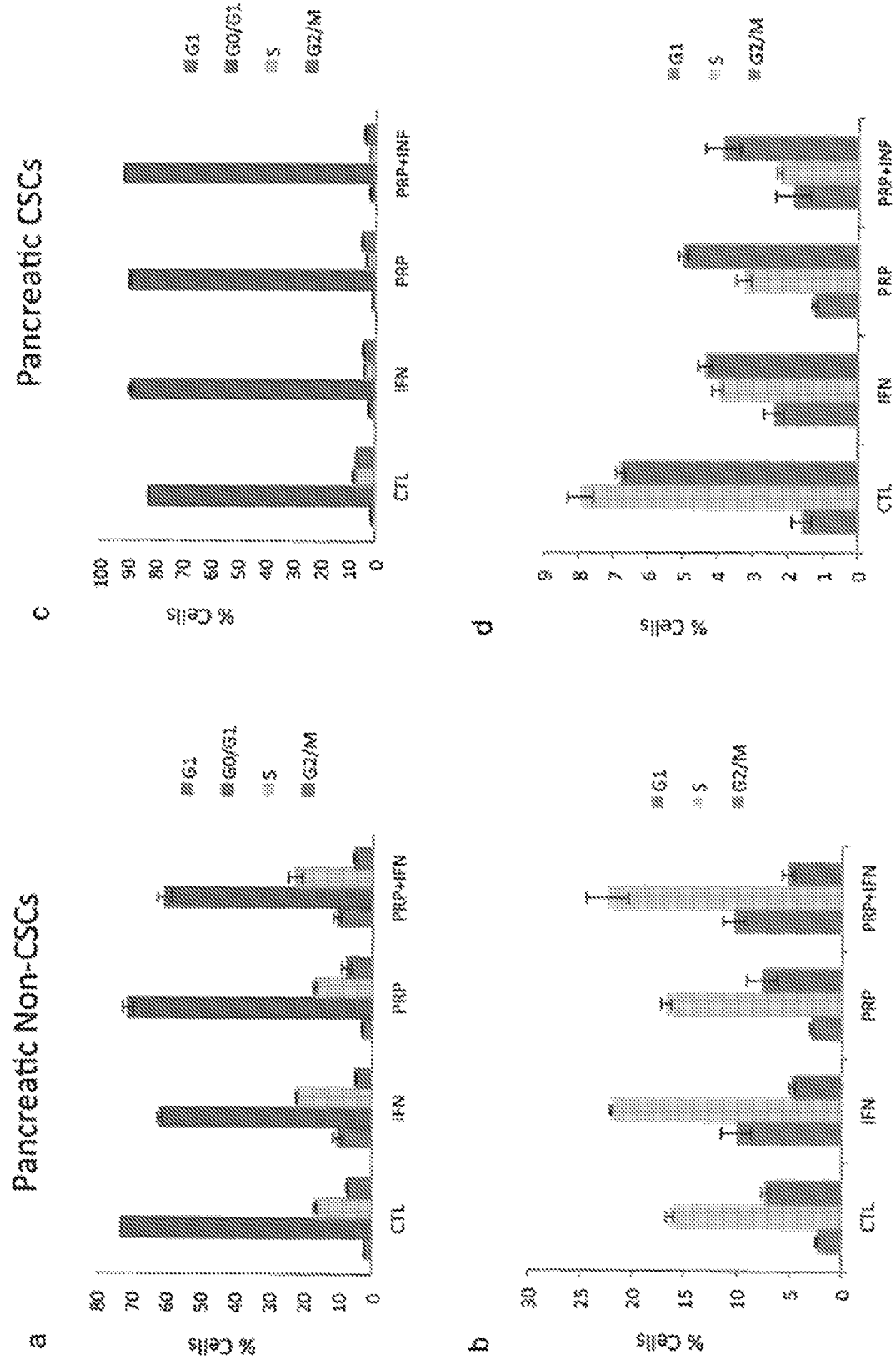
FIG. 2: Cell cycle assay for human pancreatic cancer cell line BxPC3. Panels a and b show assay results for pancreatic non-CSCs; panels c and d show assay results for pancreatic CSCs.
Figure 3:
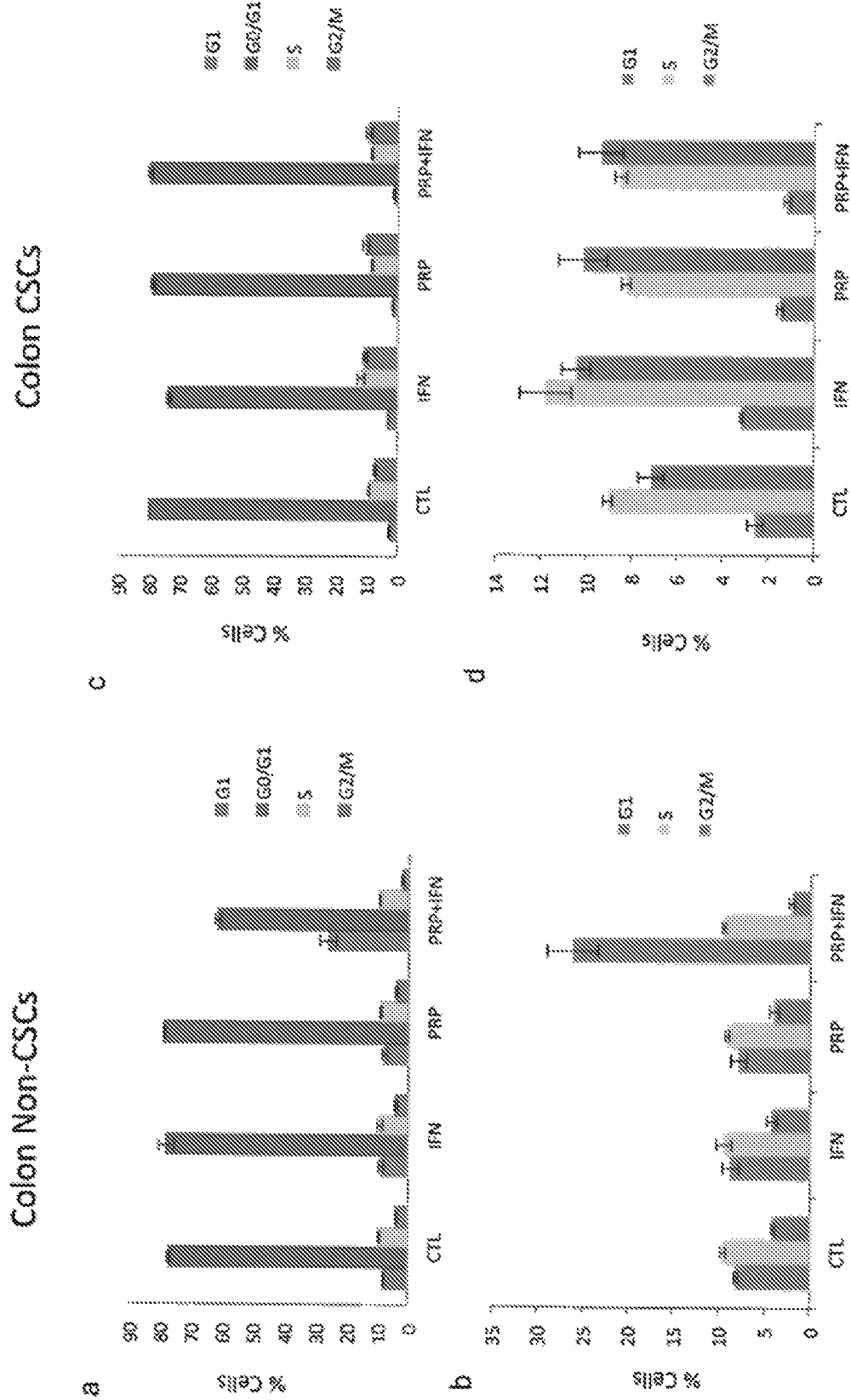
FIG. 3: Cell cycle assay for human colon cancer cell line HCT-116. Panels a and b show assay results for colon non-CSCs; panels c and d show assay results for colon CSCs.

PRP treatment resulted in a slight decrease in the number of cells in phase S compared with the control (3.25% vs 7.95%), an effect that was potentiated with the addition of IFN (2.25%) (FIG. 2d). There was no marked difference in cell cycle in colon CSCs after treatment with PRP (FIG. 3d).

These results suggest that Trypsinogen/Chymotrypsinogen decreases the ability of pancreatic CSCs to proliferate and reduces S phase in pancreatic CSCs.

ALDEFLUOR Assay

CSC mechanisms for survival include an increased metabolic activity through aldehyde dehydrogenase (ALDH). For this reason ALDH has been described as a marker for the identification of cancer stem cells (Huang et al. (2009). Cancer Res Vol. 69 (No. 8):3382-3389). ALDH positive cells can be detected with ALDEFLUOR reagent by using flow cytometry. Aldefluor assay is based on the conversion of fluorescent non-toxic substrate for ALDH substrate to the fluorescent reaction product. Non-toxic substrate for ALDH can freely diffuse into intact, viable cells. The BODIPY aminoacetaldehyde is converted to the fluorescent product BODIPY aminoacetate by ALDH activity. ALDH positive cells have been found in various cancer tissues including breast, liver, colon, pancreas, prostate, lung, ovarian and acute myelogenous leukemia and are related to cancer chemo resistance (Siclari and Qin (2010) J Orthop Surg Res 5(78)).

Figure 4:
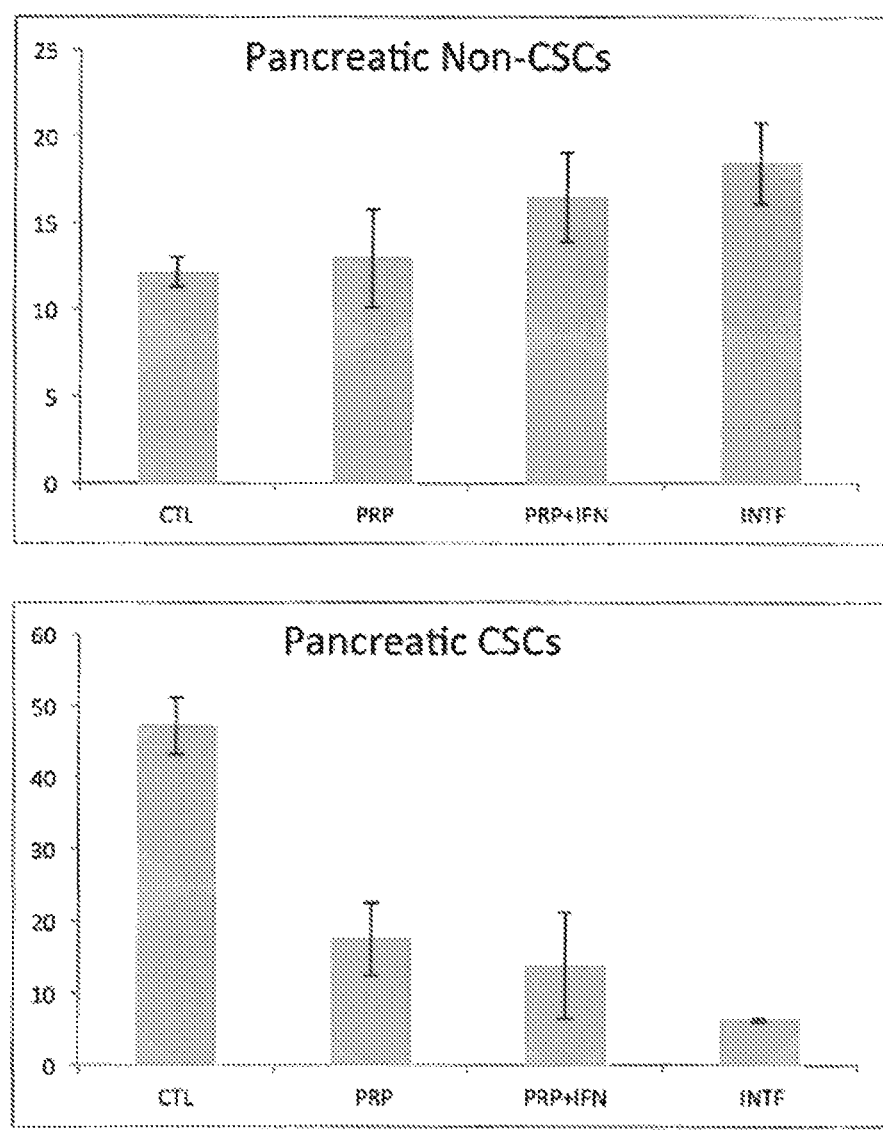
FIG. 4: Aldehyde dehydrogenase assay for human pancreatic cell line BxPC3. The percentage of ALDH-positive cells in pancreatic non-CSCs and CSCs is shown following treatment of the cells with control, PRP, PRP+IFN or IFN.

FIG. 4 shows the results of ALDH assay on pancreatic CSCs and non-CSCs.

The percentage of ALDH-positive cells in non-CSC samples was approximately 12%. For cells cultured under sphere-forming conditions, approximately 50% of cells were ALDH-positive. Treatment of cells with PRP significantly reduced the population of ALDH-positive cells (from 47.2% to 17.5%) in pancreatic CSCs. The addition of IFN further increased the effect of PRP (13.8%). These results indicate that Trypsinogen/Chymotrypsinogen reduces the CSC population in pancreatic cancer.

Expression of CSC Markers in Trypsinogen/Chymotrypsinogen-Treated Cells

Pancreatic cancer cells were grown under sphere-forming conditions to enrich the subpopulation of CSCs. Pancreatic CSCs were then treated with PRP (Trypsinogen/Chymotrypsinogen 0.07 mg/ml:0.42 mg/ml), PRP+IFN and IFN and the pancreatic-specific CSC markers CD 326, CD 44 and CxCR4 were measured by flow cytometry.

Figure 5:
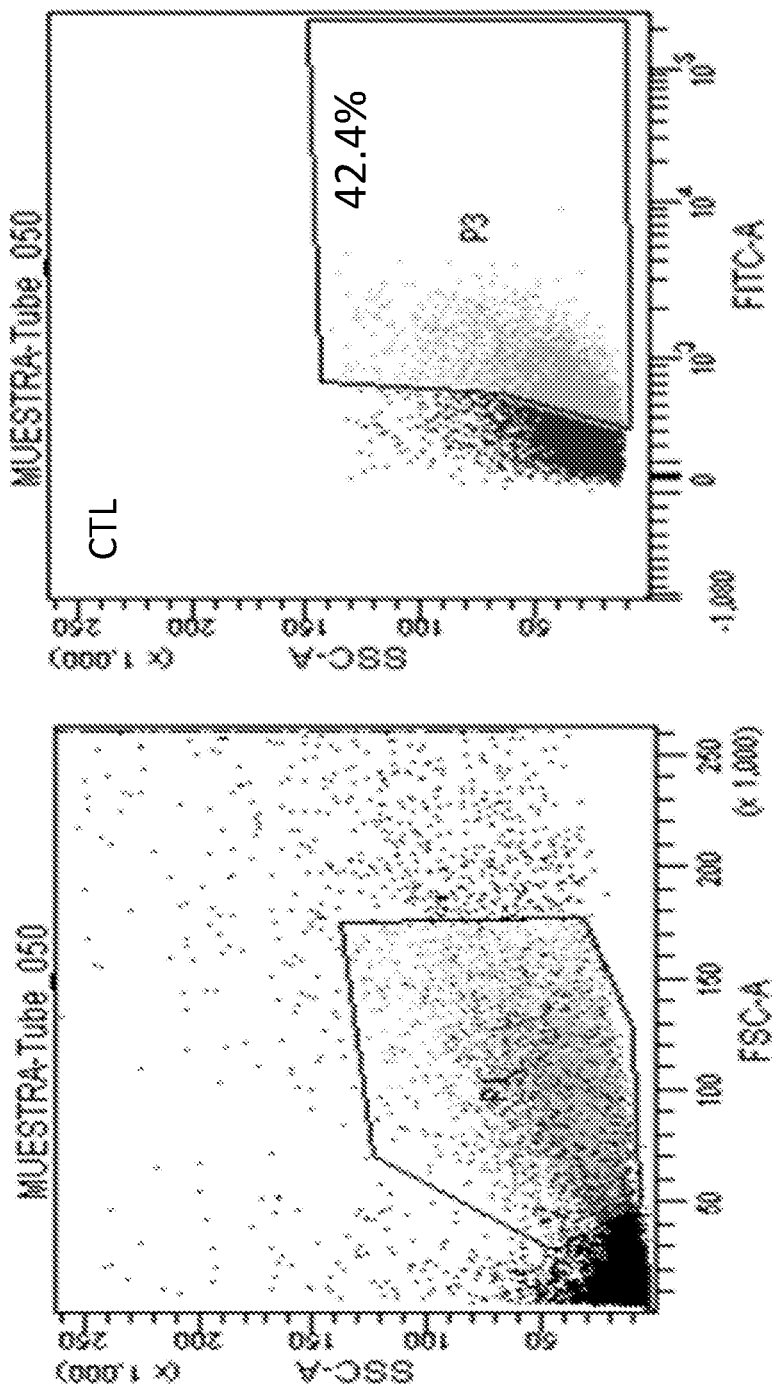
FIG. 5: Dot plot results of flow cytometry sorting of pancreatic CSCs on the basis of cell-surface expression of markers CD 326, CD 44 and CxCR4 following treatment of the cells with PRP, PRP+IFN or IFN.
Figure 5:
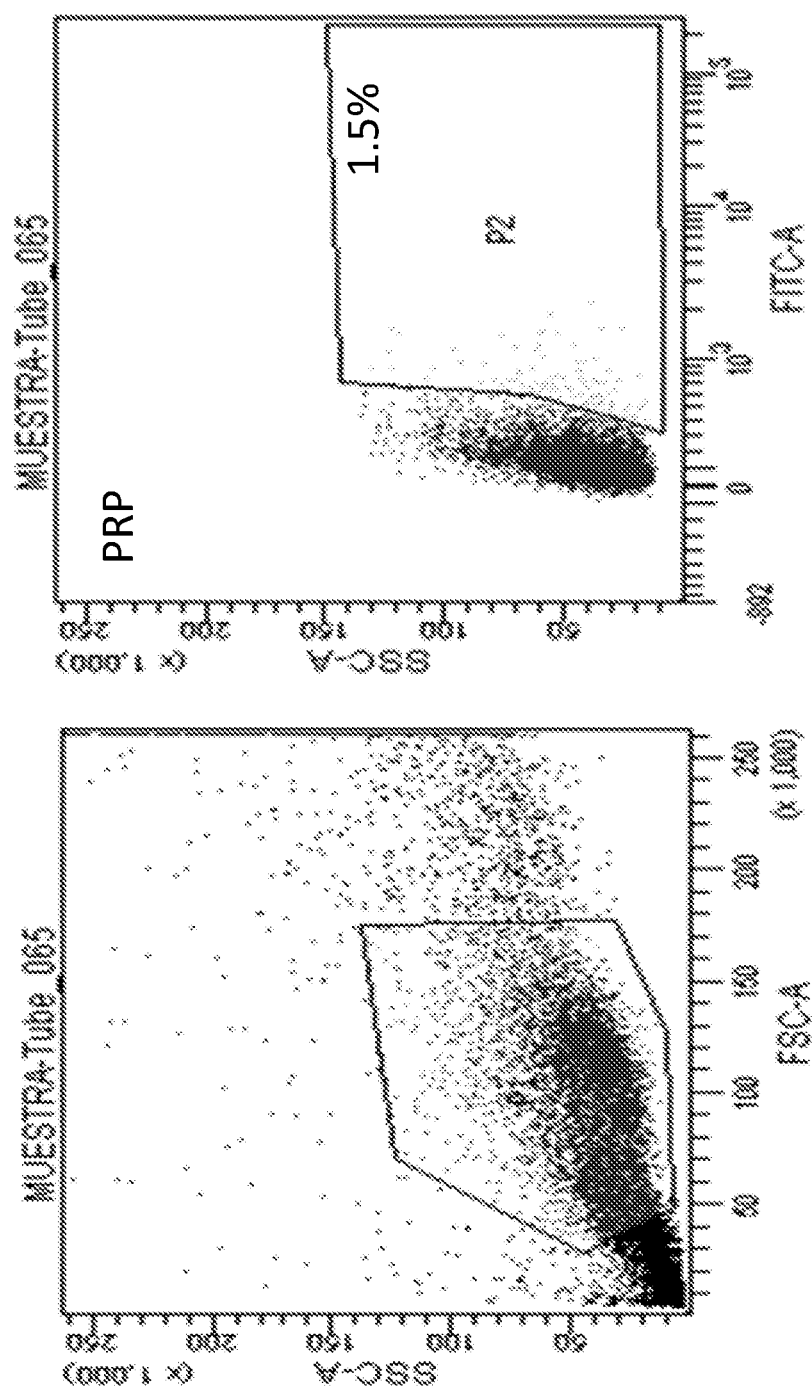
Figure 5:
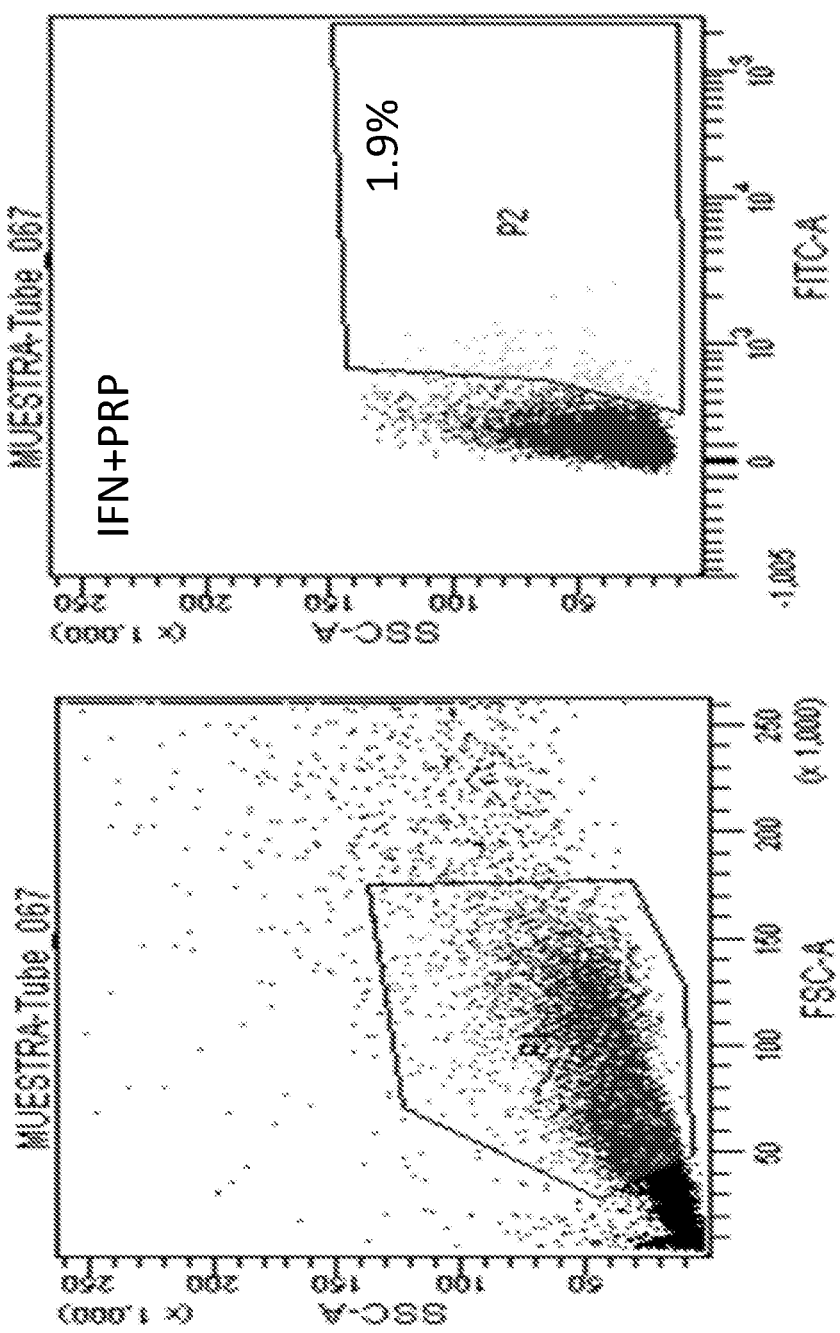
Figure 5:
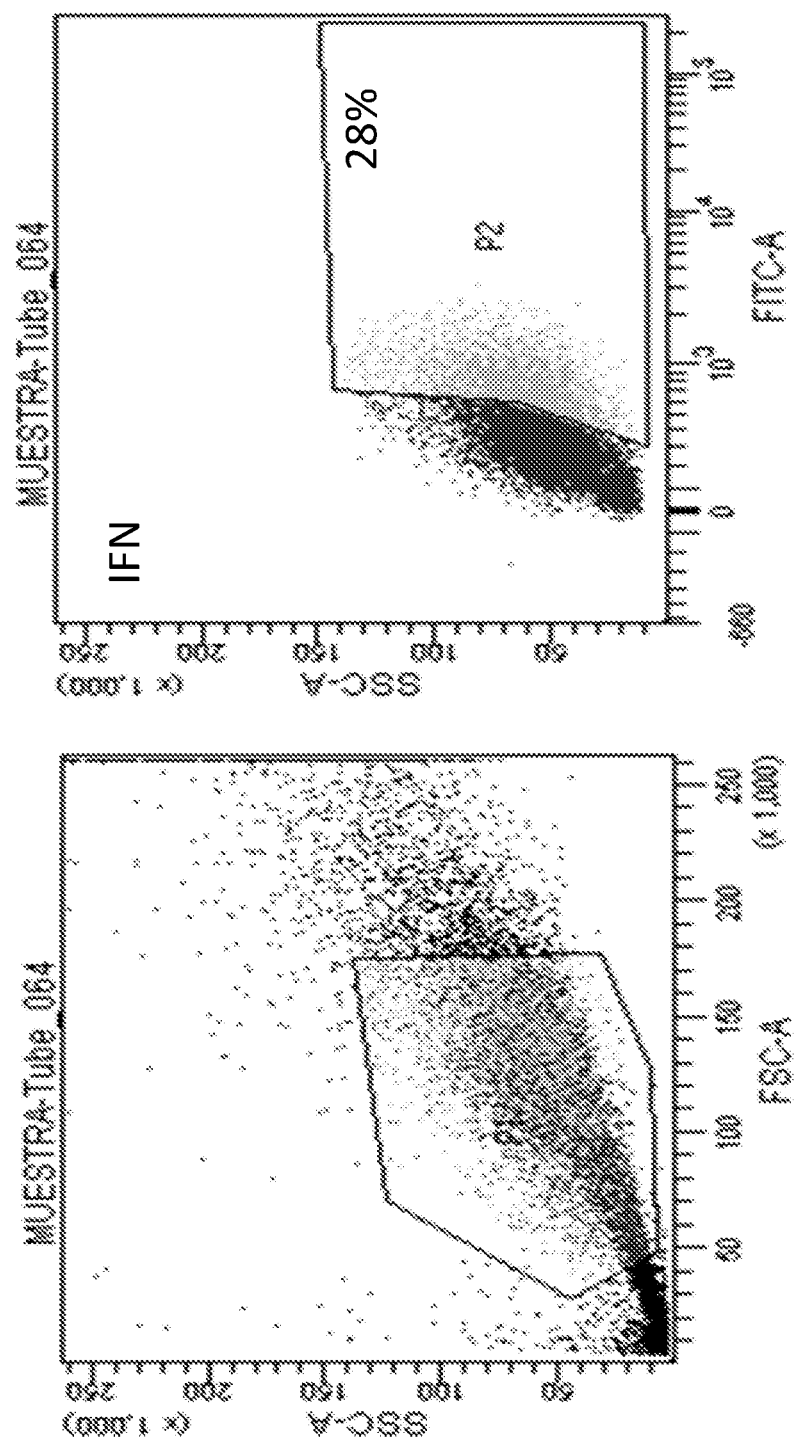
Figure 5:
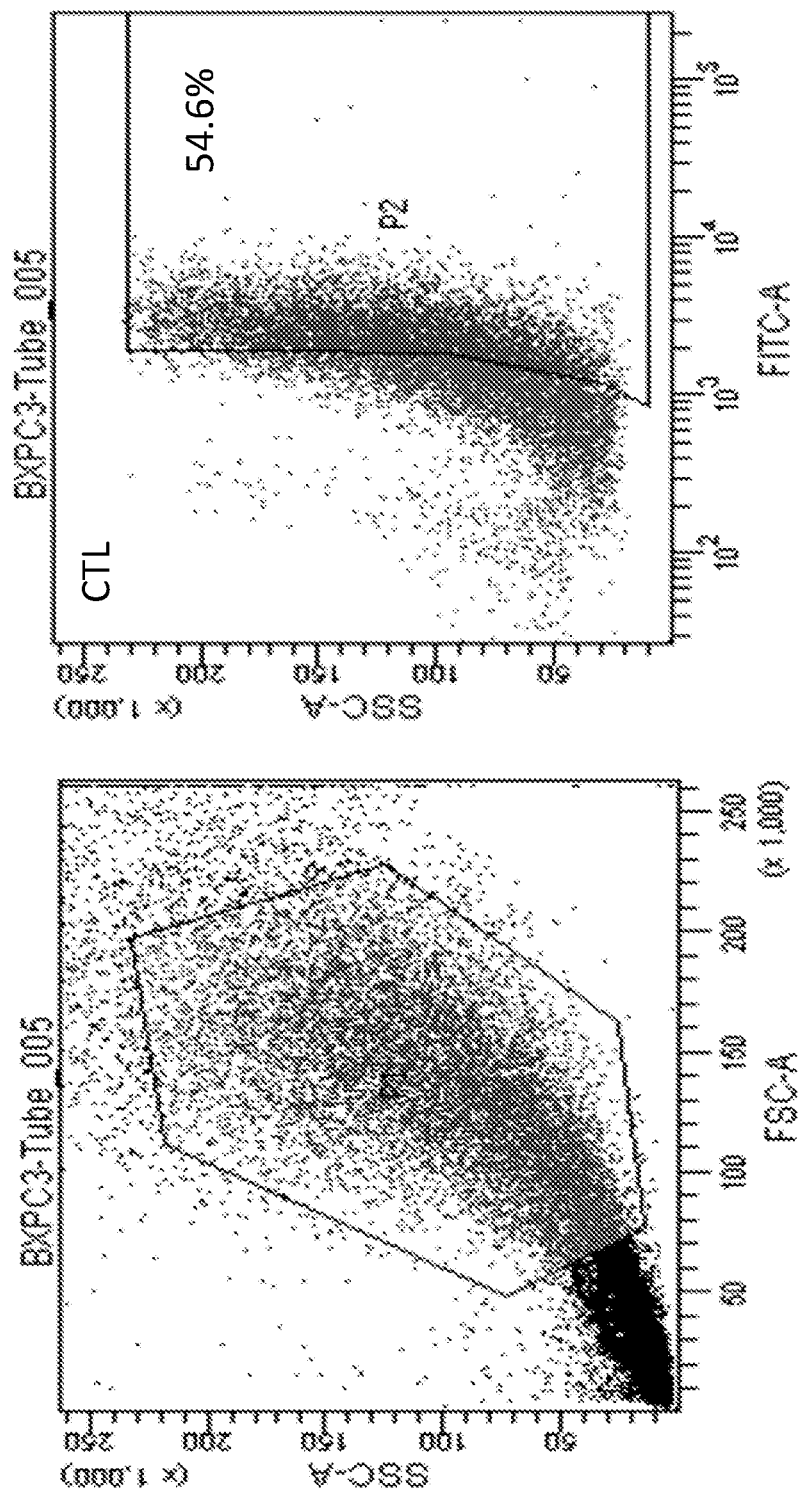
Figure 5:
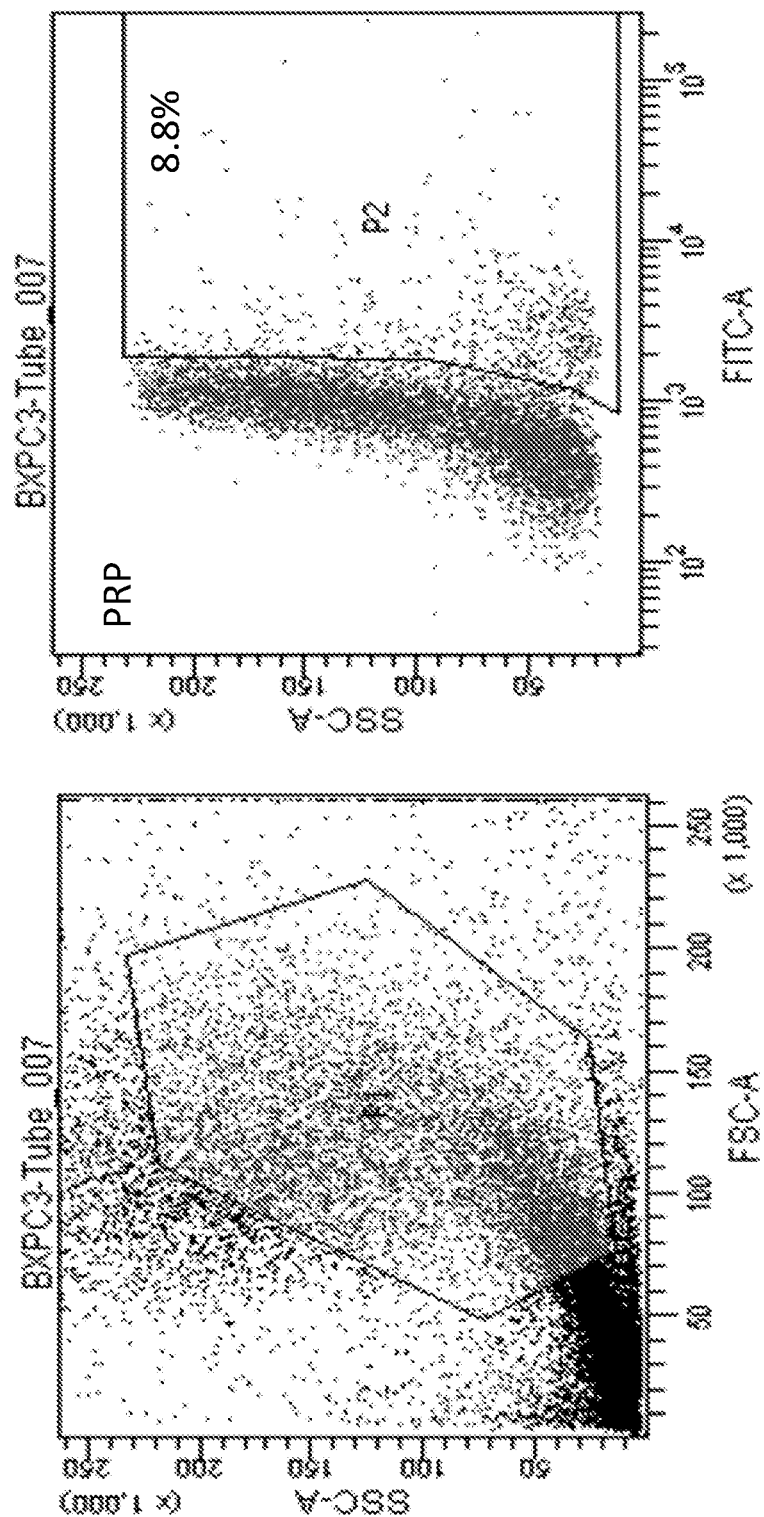
Figure 5:
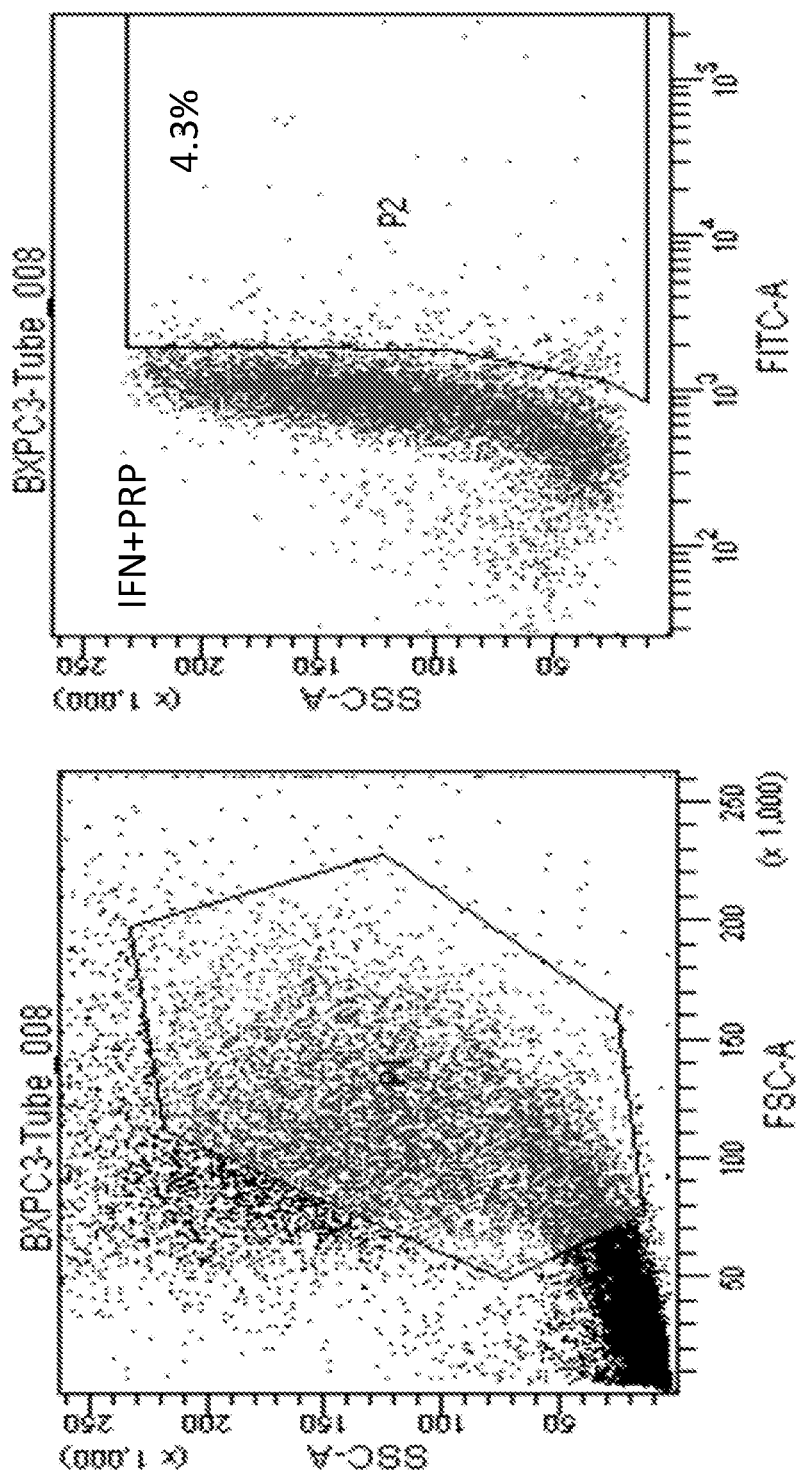
Figure 5:
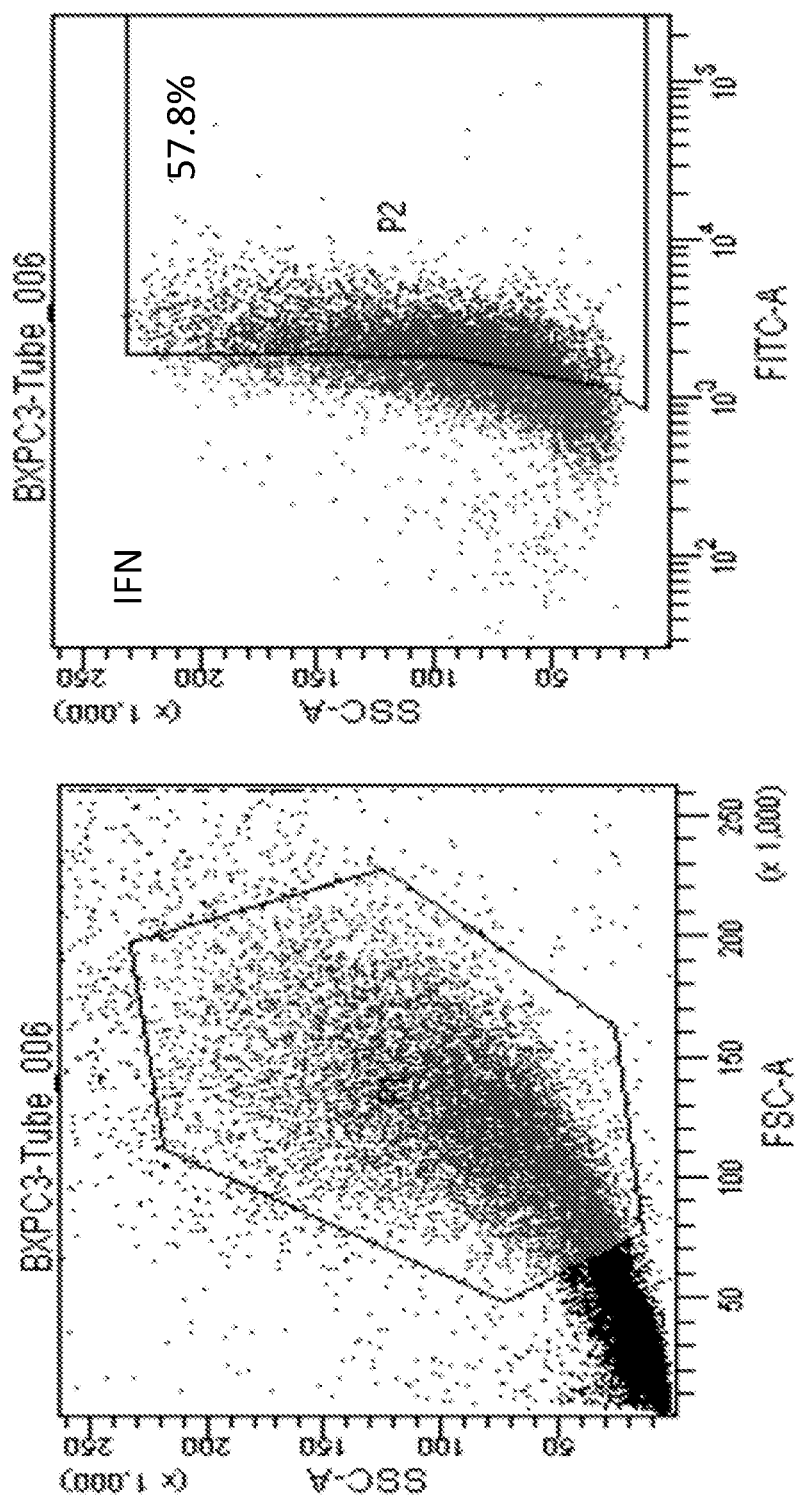
Figure 6:
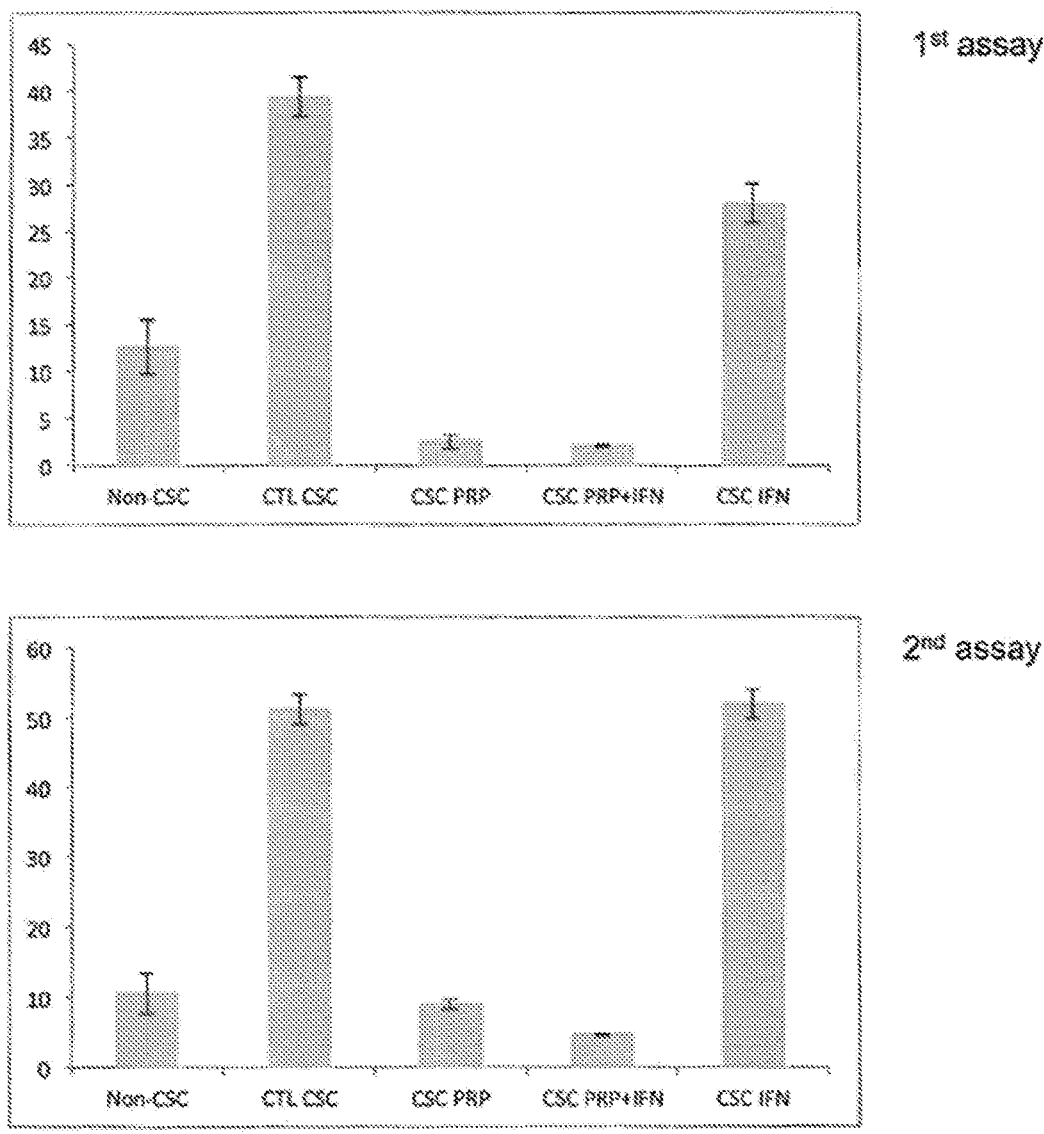
FIG. 6: Histogram showing expression of CSC markers in pancreatic CSCs: percentage of cells having the three markers CD326, CD44, CxCR4 are shown for CSCs treated with PRP, PRP+IFN or IFN and for non-CSCs. The results of two separate assays are shown.

Flow cytometry results demonstrate that the percentage of cells expressing the three CSC markers significantly decreases after treatment with PRP (from 56.6% to 8.8%). Treatment with PRP+IFN reduced the population of cells expressing those markers to 4.3% (FIGS. 5 and 6). These results suggest that treatment with PRP reduces the CSC population in pancreatic cancer.

Colon cancer cells were grown under sphere formation condition to enrich the subpopulation of CSCs. Colon CSCs were then treated with PRP, PRP+IFN and IFN. Cells were marked with ALDH together with the colon-specific CSC markers: CD326 and CD44 and analysed by flow cytometry.

Figure 7:
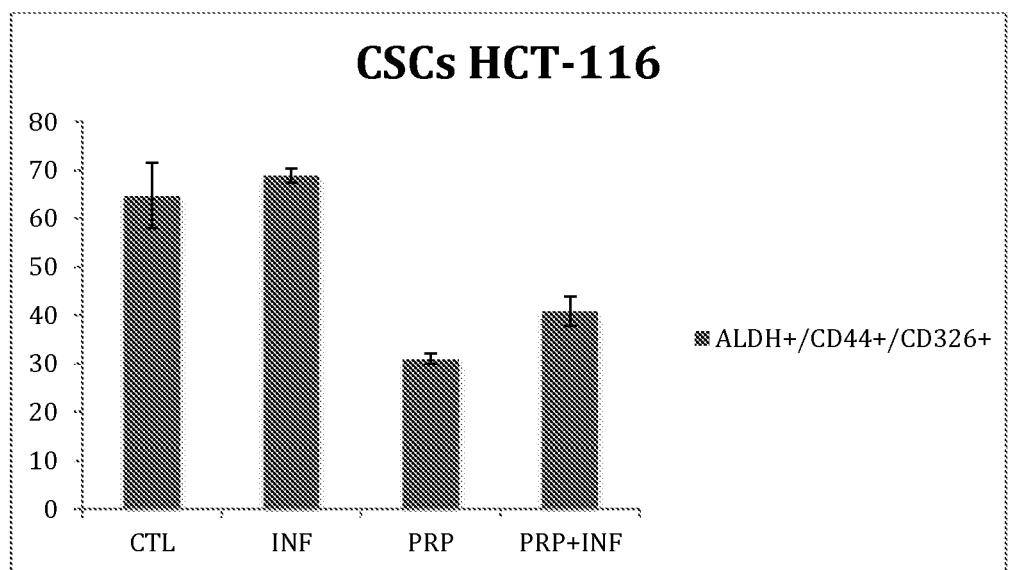
FIG. 7: Histogram depicting the results of flow cytometry sorting of colon CSCs. The percentage of HCT-116 CSCs which are ALDH positive and express CD44 and CD326 markers are shown for cells following treatment with PRP, IFN or PRP+IFN.
Figure 8:
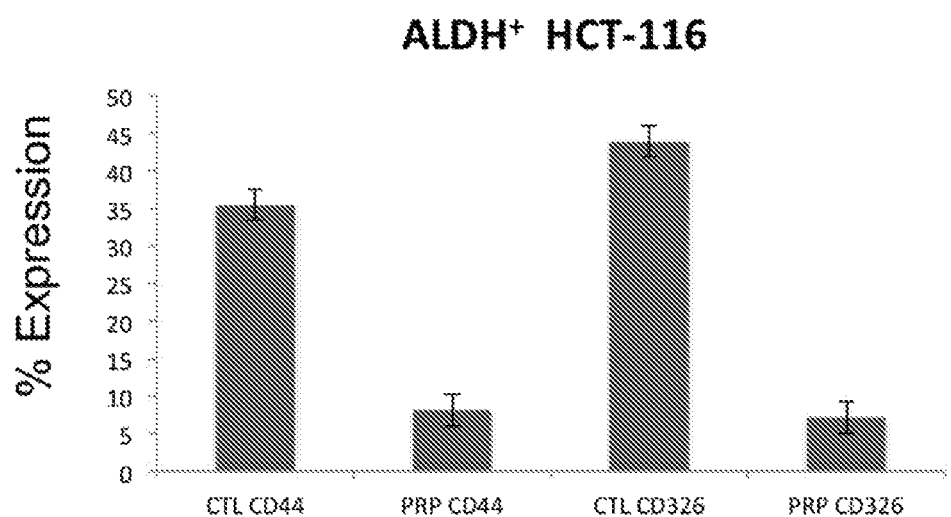
FIG. 8: Histogram depicting the percentage of ALDH-positive HCT-116 CSCs which express the markers CD44 or CD326 following treatment with PRP.

Flow cytometry results (FIGS. 7 and 8) demonstrate that the percentage of cells that were both ALDH-positive and expressed both colon-specific CSC markers significantly decreased after PRP treatment (from 64.8% to 31.05%). Treatment with PRP+ INF reduced the population of cells that expressed those markers to 40.8% (FIG. 7). The percentage of cells that were ALDH+ and express either CD44 or CD326 markers significantly decreased after PRP treatment (from 35.5% to 8.1% for ALDH+CD44+ cells and from 43.9 to 7.1% for ALDH+CD326+ cells—FIG. 8).

CSC Sphere Formation in Presence of Trypsinogen/Chymotrypsinogen

The ability of PRP to suppression sphere formation was tested. PRP (Trypsinogen/Chymotrypsinogen 0.07 mg/ml: 0.42 mg/ml), IFN (10000 UI/ml) and PRP+IFN were added to the medium at day 0, when the cancer cells were cultured under sphere conditions (conditioned medium and low attachment culture wells).

Figure 9:
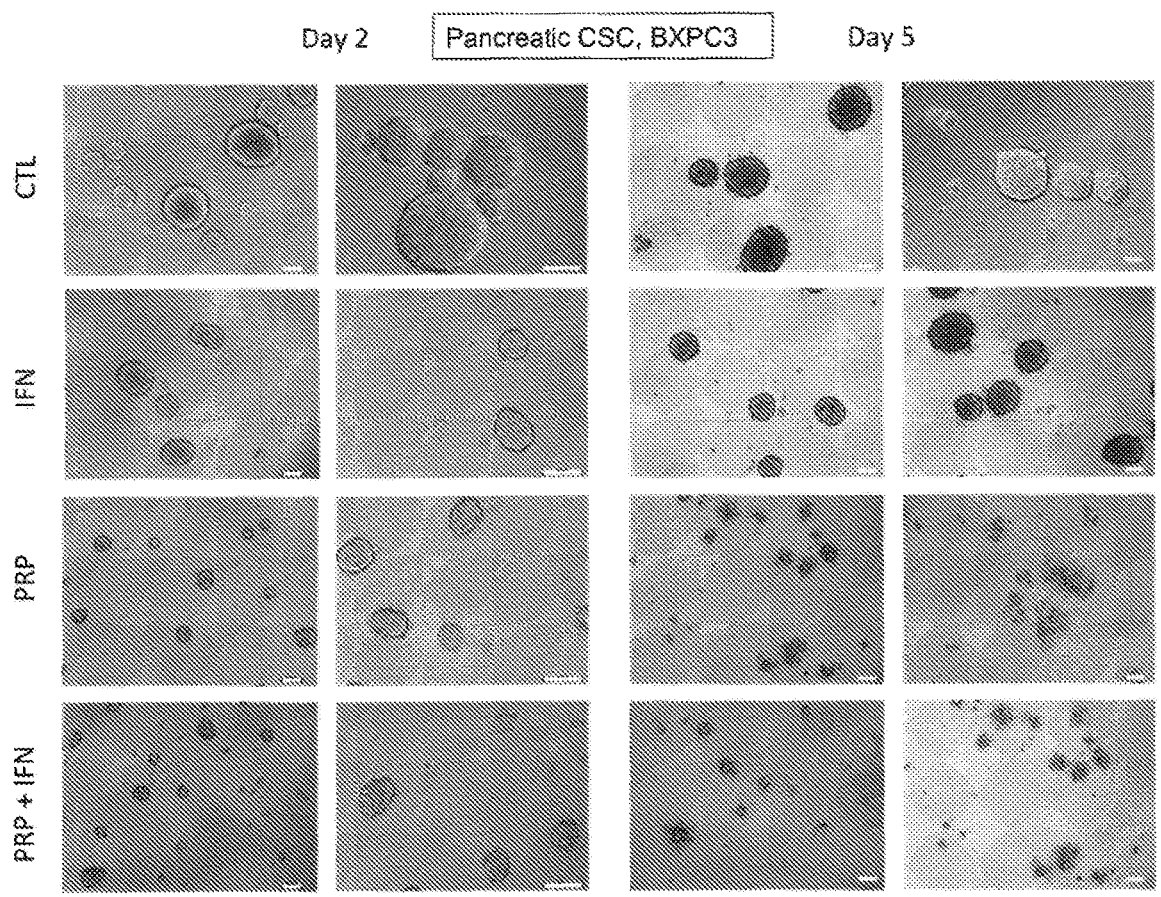
FIG. 9: Representative light microscopy images showing sphere formation of pancreatic BxPC3 CSCs at days 2 and 5 following treatment with PRP, INF or PRP+IFN.

FIG. 9 show images of the pancreatic cell cultures on day 2 and day 6. The day 2 images show that the addition of PRP to the medium significantly reduces the number and size of pancreatic CSC spheres. In addition, the morphology of the spheres formed is markedly different (being regular in the control non-treated cells while irregular in PRP-treated cells).

The day 5 images show key differences between Trypsinogen/Chymotrypsinogen A-treated cells and control cells. PRP and PRP+IFN treated cells do not form spheres. Cells appear to be disassociated and ruptured.

Figure 10:
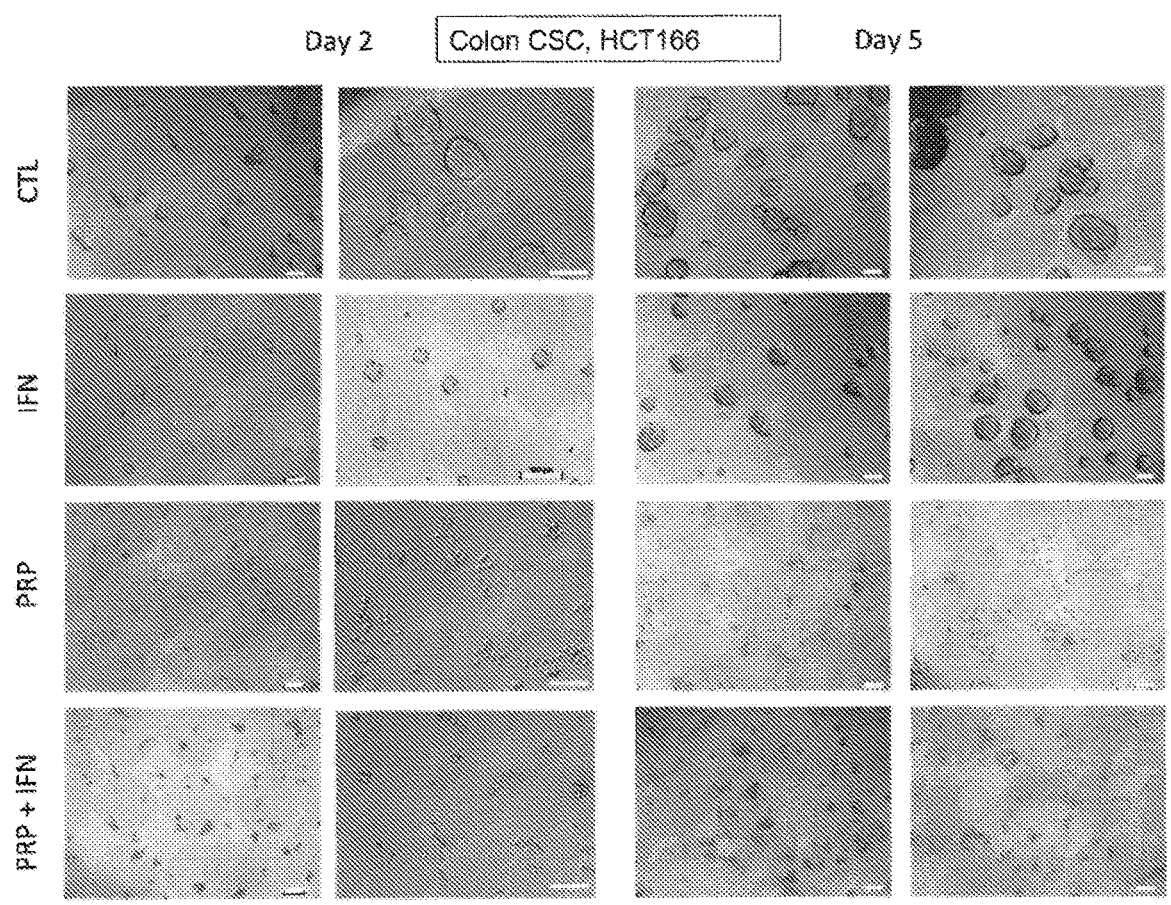
FIG. 10: Representative light microscopy images of sphere formation by colon HCT-166 CSCs at days 2 and 5 following treatment with PRP, INF or PRP+IFN.

The results with the colon cancer cells were different. FIG. 10 show that the addition of PRP inhibited the formation of the spheres even at day 2. Cells appear disperse but not dead. On day 5 the sphere had not yet been formed and the cells were not aggregated.

These results indicate that Trypsinogen/Chymotrypsinogen markedly inhibits spheroid formation by CSCs.

Neuroblastoma CSC Sphere Formation in Presence of PRP

PRP (Trypsinogen/Chymotrypsinogen 0.07 mg/ml:0.42 mg/ml), was added to the cell medium at day 2 and at day 4, when the cancer cells were cultured under sphere conditions (conditioned medium and low attached culture wells).

Figure 11:
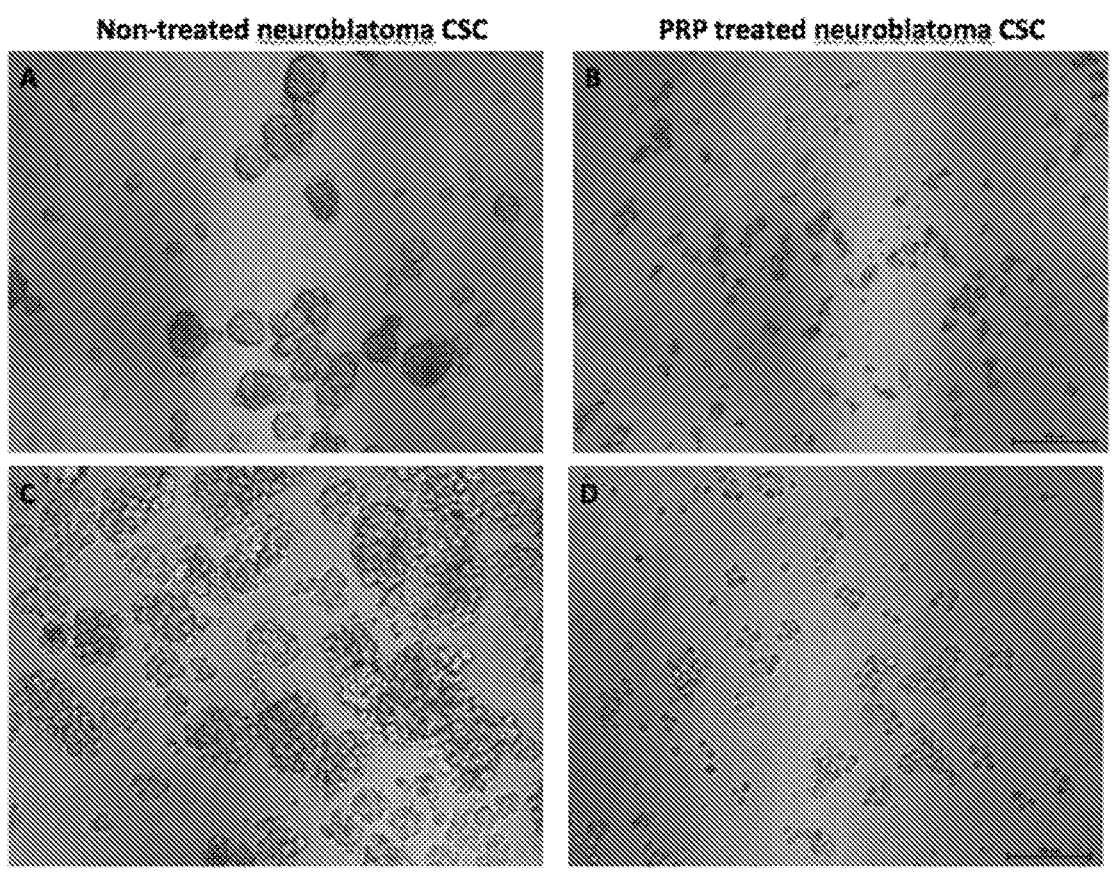
FIG. 11: Representative light microscopy images of neuroblastoma spheres formed when SK-N-SH cells were cultured under CSC conditions (Panel A and C). The addition of PRP to the medium prevents the formation of neuroblastoma spheres (Panel B and D). Original magnification: 10× for panels A and B; 20× for panels C and D. E and F: number of primary (E) and secondary (F) spheres in non-treated and PRP-treated BxPC3 and SK-N-SH cells.
Figure 11:
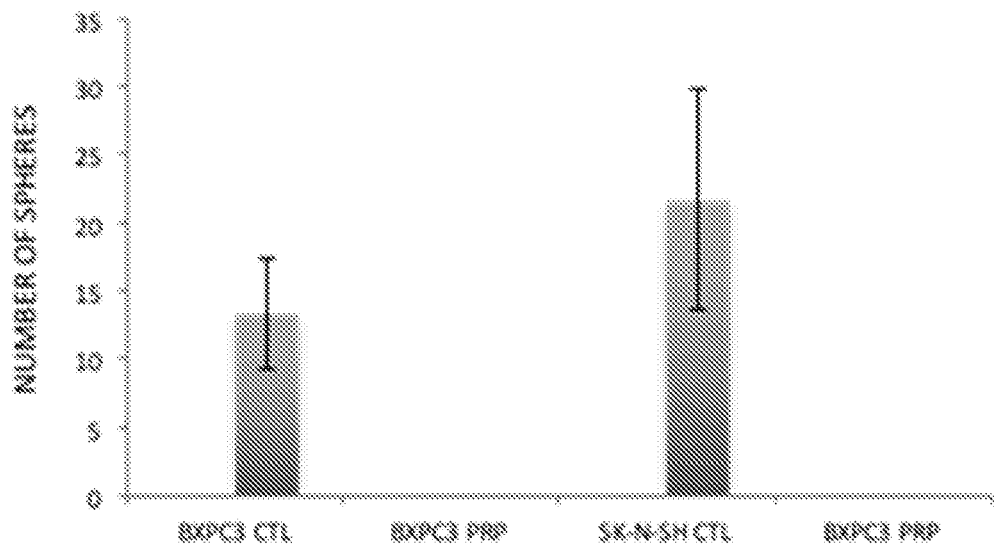
Figure 11:
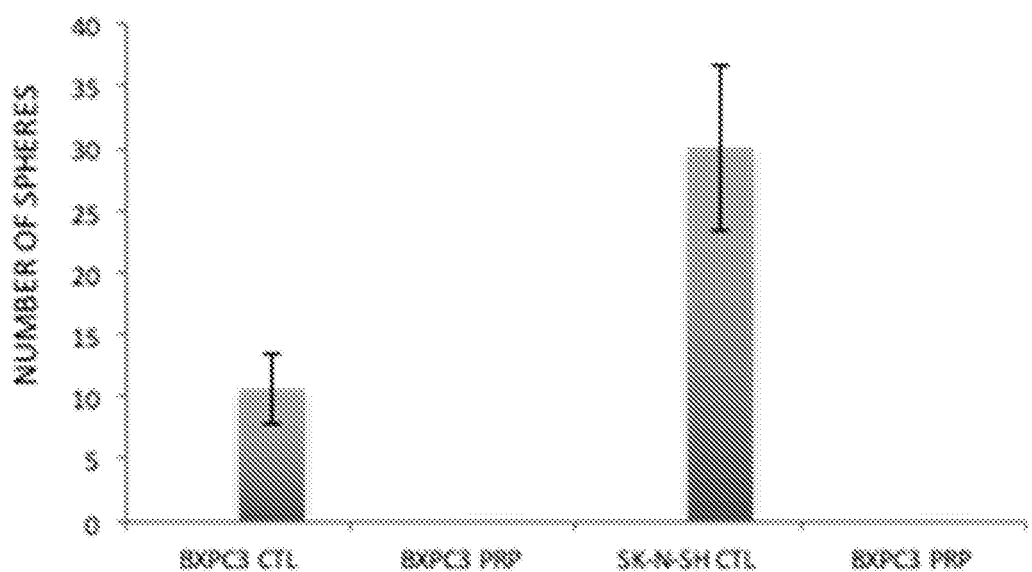

FIG. 11 shows images of the cell cultures on day 6. Neuroblastoma treated with PRP do not form CSC spheres: cells grow in suspension but do not form cell clusters (FIGS. 11 B and D). Neuroblastoma sphere CSCs are shown in panels A and C, when cells were maintained under control conditions in the absence of PRP.

Secondary Sphere Formation

A secondary sphere-formation assay was performed by dissociating primary spheres formed by PRP treated cells and comparing with control non-treated cells. FIG. 11E shows that for the cancer cell lines BxPC3 and SK-N-SH, no secondary spheres could be counted after PRP treatment. In contrast non-treated control cells were able to recover the ability to form cell clusters.

PRP destroys primary spheres and also suppresses the ability of CSCs to form secondary spheres. As tumor spheres are defined as clonally derived non-adherent colonies of cells derived from a single tumor stem cell, the results obtained demonstrate that PRP treatment has a direct effect on the cancer stem cell population.

EMT and Pluripotency-Associated Gene Expression

Figure 12:
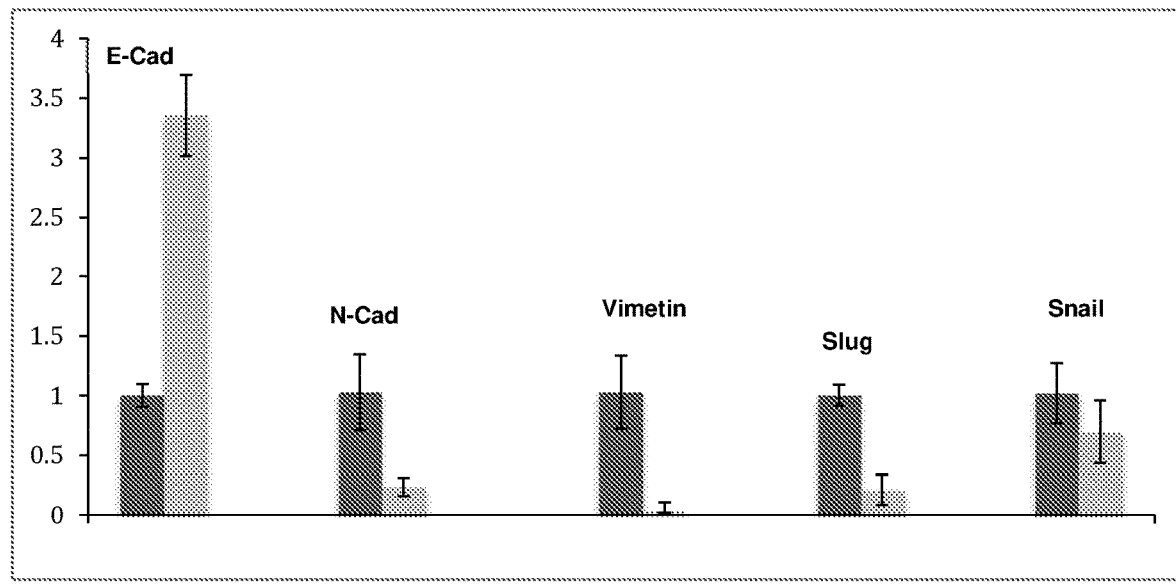
FIG. 12: Results of qRT-PCR analysis for the expression of EMT-related genes after treatment with PRP (light grey). Data are normalized to 1 for non-treated CSC using GAPDH as internal control, and graphed as mean±SEM (n=3).

The expression of genes related with the EMT process and/or pluripotency was analysed in pancreatic CSCs treated with PRP (Trypsinogen/Chymotrypsinogen A 0.07 mg/ml: 0.42 mg/ml), and compared with untreated CSCs. qRT-PCR results show that genes related to EMT such as SNAIL, SLUG, VIMENTIN and N-CADHERIN had decreased expression after treatment (FIG. 12). E-CADHERIN expression was increased after treatment. These results suggest that PRP treatment may reduce the conversion from an epithelial to a mesenchymal phenotype.

Figure 13:
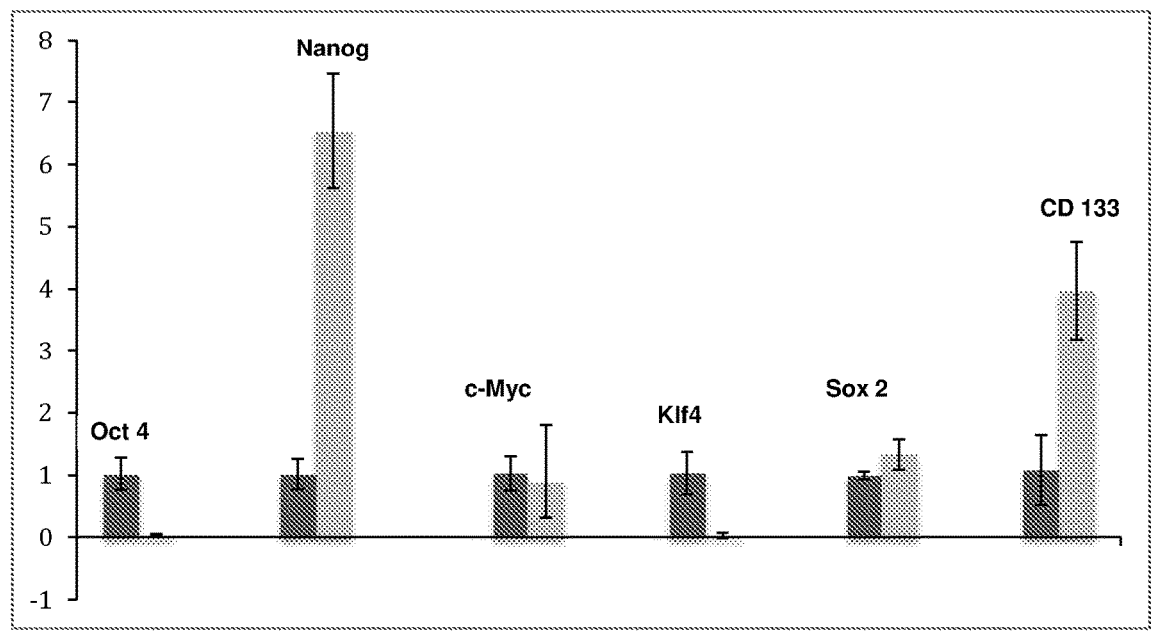
FIG. 13: Results of qRT-PCR analysis for the expression of CSC-related genes after treatment with PRP (light grey). Data are normalized to 1 for non-treated CSC using GAPDH as internal control, and graphed as mean±SEM (n=3).

To determine if PRP treatment alters expression of CSC markers, several genes of pluripotency were analysed by qRT-PCR (primers used are described in Table 4). The results show that OCT4, CMYC and KLF4 gene expression slightly decreased following treatment with Trypsinogen/ Chymotrypsinogen A when compared with non-treated CSCs. In contrast, expression of NANOG and CD133 increased after treatment, indicating that the effect of PRP is not mediated though these two genes (FIG. 13).

Microarray Studies

The following results relate to changes in gene expression in CSCs following PRP treatment.

a) Expression Genes Associated with EMT

To study the effect of PRP on EMT process, the expression of several key genes involved in EMT was analysed in treated CSCs and compared with the gene expression profile of control non-treated CSCs. Results are shown as the fold regulation (up or down) compared with control cells.

Figure 22:
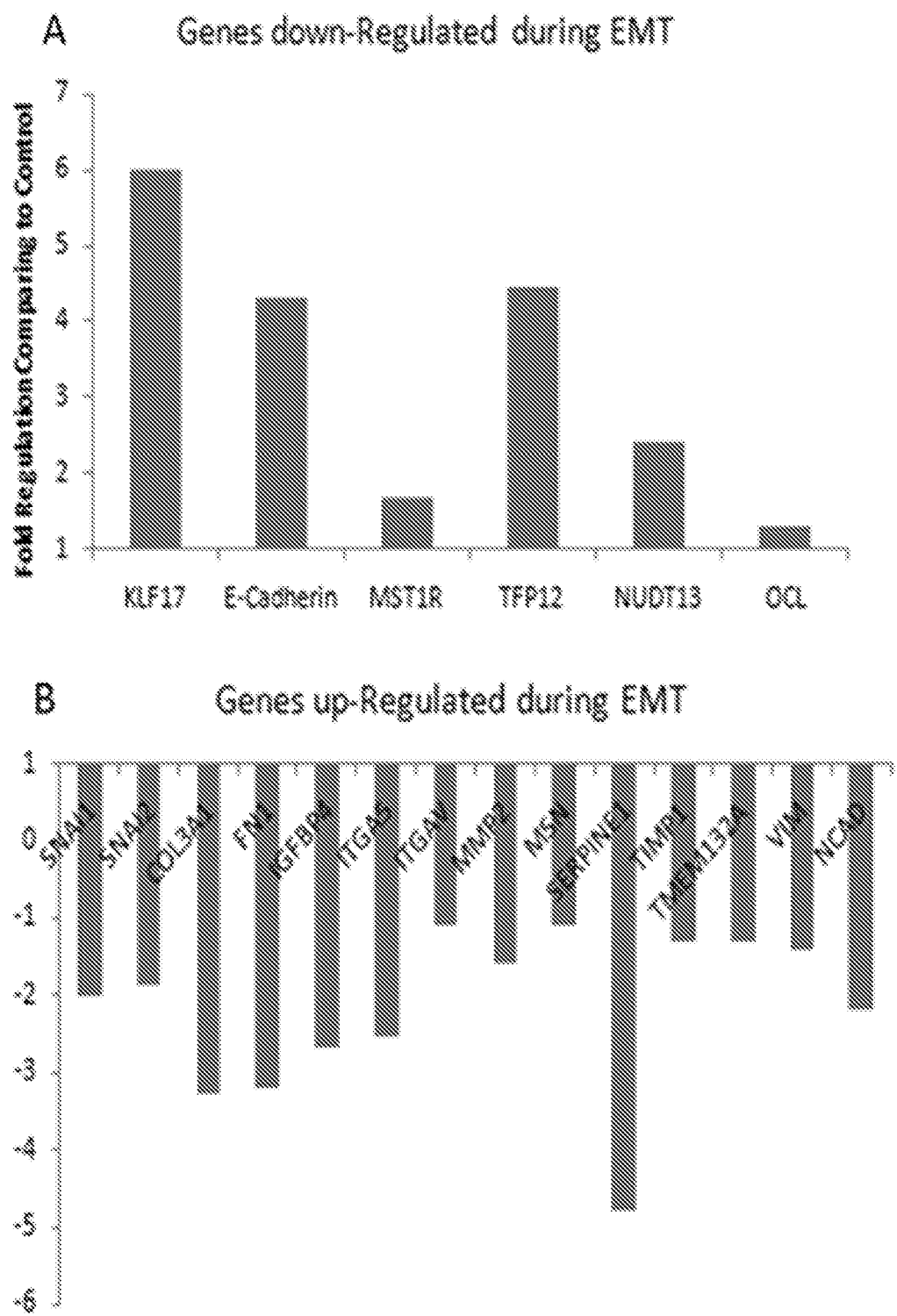
FIG. 22: Expression levels of EMT-related genes in CSCs following PRP treatment. A: expression of genes normally down-regulated during EMT but up-regulated following PRP treatment. B: expression of genes normally up-regulated during EMT but down-regulated following PRP treatment.

FIG. 22A shows the change in gene expression of select genes that are normally down regulated during the EMT process. FIG. 22A shows that following PRP treatment, expression of E-cadherin increased 4.28-fold, indicating that PRP treatment induces expression of this gene. Furthermore, Kruppel-like-factor 17 (KLF17) was also up-regulated by PRP treatment, reaching a fold up-regulation of 5.9. KLF17 has previously been reported to directly supress EMT, angiogenesis, invasion and metastasis. The expression of other genes was also increased following PRP treatment (e.g., MST1R: 1.6928-fold; TFPI2: 4.4272-fold and NUDT13: 2.3692-fold), suggesting that PRP has an anti-EMT effect.

Genes that are normally up regulated during EMT were analysed and the results are summarized in FIG. 22B. 13 genes that have been described to induce EMT were down regulated following treatment with PRP. For example, the transcription factor Snail, which is typically up-regulated in metastatic cells that are undergoing EMT, was down regulated following PRP treatment (SNAI1:−1.9678 and SNAI2:−1.8604). The serine protease inhibitor SERPINE1, was significantly down-regulated (4.6-fold downregulation) following PRP treatment. Expression of the integrins ITGA5 and ITGAV was also was down regulated (2.5697 and 1.0193 downregulation, respectively). ITGA5 has been reported to promote tumor invasion and higher expression of this gene has previously been correlated with a shorter survival time in cancer patients. ITGAV is also implicated in the regulation of angiogenesis and cancer progression.

In conclusion, PRP treatment has a significant effect on the expression of genes that are involved in the EMT process, by inducing the expression of genes normally downregulated during EMT, and reducing the expression of genes normally upregulated during EMT. The results indicate the therapeutic potential for PRP in reducing tumor progression and metastasis, in addition to repressing the CSC population.

b) Expression of Genes Involved in Stem Cell Differentiation

The expression of key genes involved in pancreatic differentiation were analysed in pancreatic CSCs. The expression of genes in CSCs treated with PRP was compared with expression of genes in control non-treated CSCs. Results are showed as the fold regulation (up or down) compared with control cells.

Figure 23:
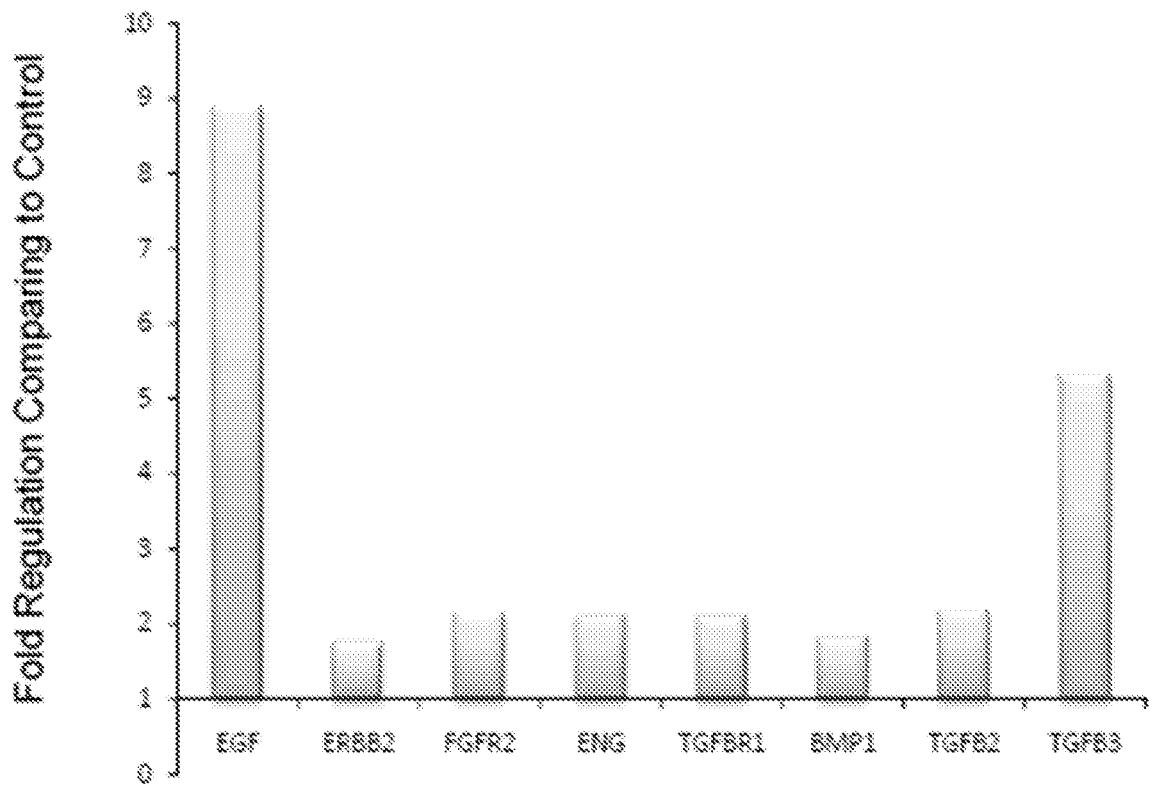
FIG. 23: The effect of PRP treatment on the expression levels of genes associated with cell differentiation in CSCs.

The results obtained are summarized in FIG. 23, and were concordant with studies, showing that PRP treatment induces cell differentiation. 7 genes related to differentiation were up regulated following PRP treatment, including the expression of epidermal growth factor (EGF), which increased 8.9 fold when compared with control cells.

c) Expression of Tumor Suppressor Genes

Figure 24:
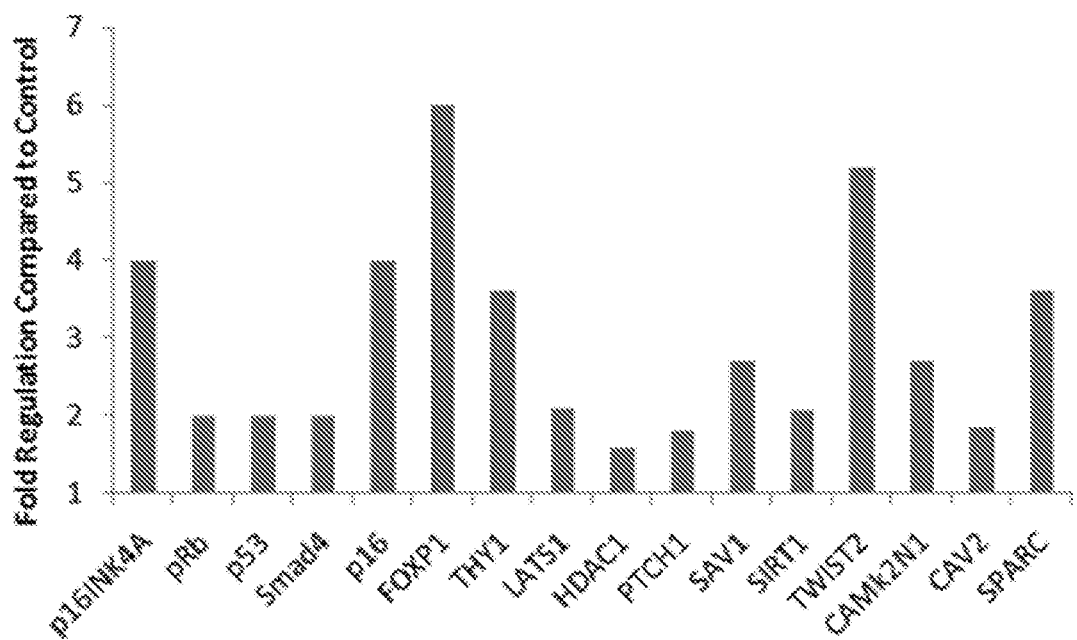
FIG. 24: The effect of PRP treatment on the expression levels of tumour suppressor genes in CSCs.

FIG. 24 shows the up-regulation of 11 genes with previously reported tumor suppressor roles, following PRP treatment.

The expression of the transcription factor FOXP1 increased 6.04 fold after PRP treatment. In addition, the expression of TWIST2 was up-regulated (5.2737-fold) following to PRP treatment. Another tumor suppressor gene that was up regulated as a consequence of PRP treatments was THY1 (3.622 fold increase).

SPARC, an extracellular protein involved in the deposition and modelling of the extracellular matrix that is down-regulated in many tumor types, was found to be up-regulated (3.611 fold) following PRP treatment. SIRT1 expression was also increased 2 fold in treated cells. SIRT1 encodes a member of the sirtuin family of proteins and has been reported to inhibit proliferation of pancreatic cancer cells expressing pancreatic adenocarcinoma up-regulated factor (PAUF).

d) Expression of Genes Related to Metastasis and Invasion

Figure 25:
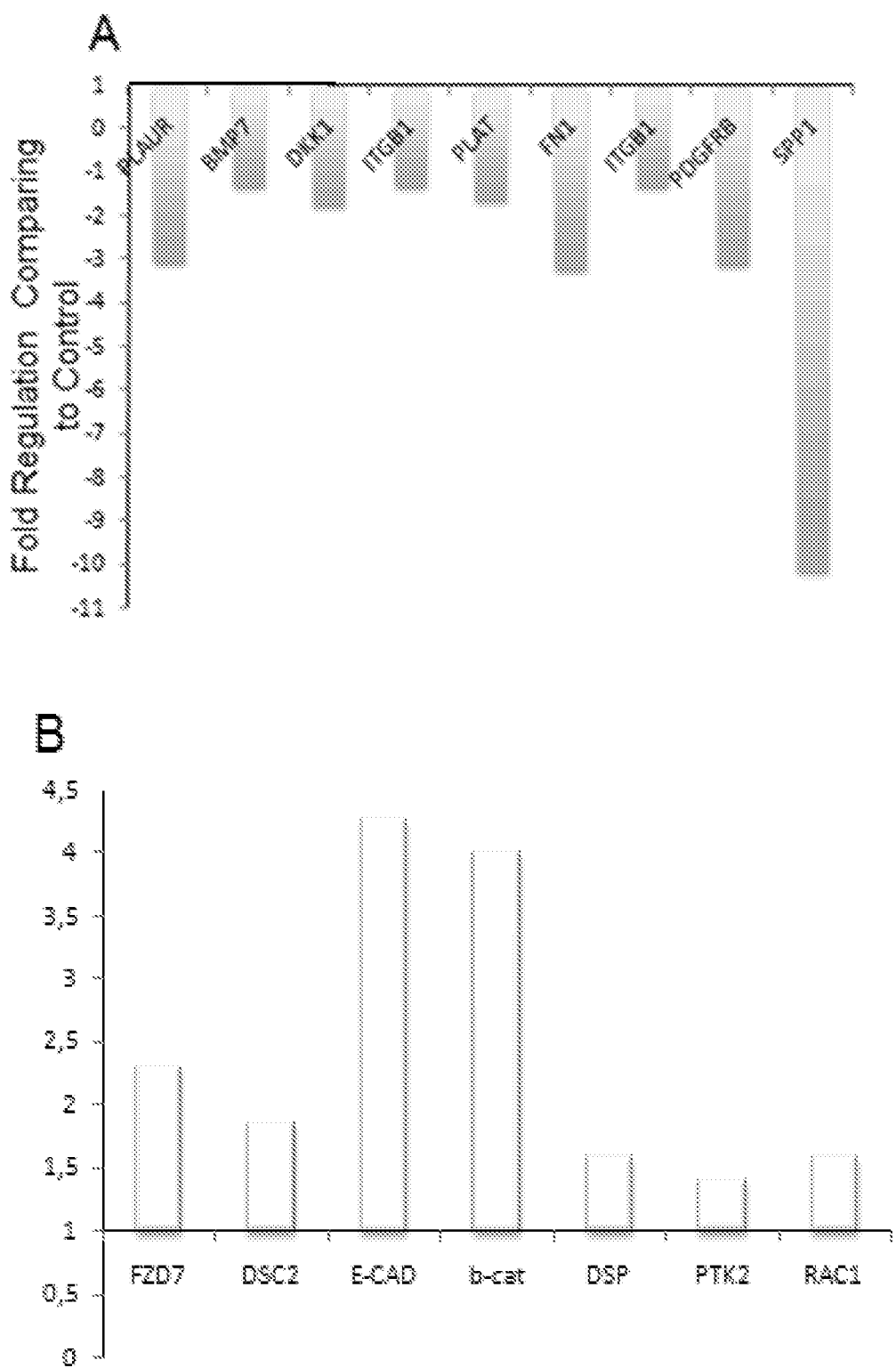
FIG. 25: The effect of PRP treatment on the expression levels in CSCs of genes associated with metastasis and invasion (A) and cell adhesion (B).

The expression level of 9 genes implicated in metastasis and cell invasion was determined following PRP treatment (FIG. 25A). The results show that PRP treatment resulted in significant down-regulation of these genes. For example, the expression of Osteopontin (SPP1) was reduced 10 fold. SPP1 is a chemokine-like, calcified ECM-associated protein that has been reported to play a crucial role in determining the metastatic potential of various cancers.

Signalling through platelet derived growth factor receptors (PDGFR) is involved in multiple tumor associated processes. The expression of PDGFR is up regulated in many tumors, for instance endothelial cells of metastatic tumors in models of orthotopically grown pancreatic carcinoma showed high expression of PDGFR. Following PRP treatment, expression of PDGFRB was reduced 3.1093-fold, indicating that PRP has an anti-metastatic effect. In addition, expression of the gene FN1 that encodes fibronectin, was also significantly reduced after PRP treatment (3.2 fold down-regulation). Fibronectin is involved in cell adhesion and migration processes including metastasis.

e) Expression of Genes Related to Cell Adhesion

FIG. 25B shows the up-regulation of genes involved in cell adhesion. The expression of E-Cadherin and β-catenin was increased (4.3 and 4-fold, respectively) following PRP treatment, in agreement with previous studies. E-Cadherin and β-catenin have known roles in EMT. The results indicate that PRP inhibits EMT by directly enhancing expression of E-cadherin and β-catenin expression in CSCs.

f) Expression of Genes Encoding Cytokines

Figure 26:
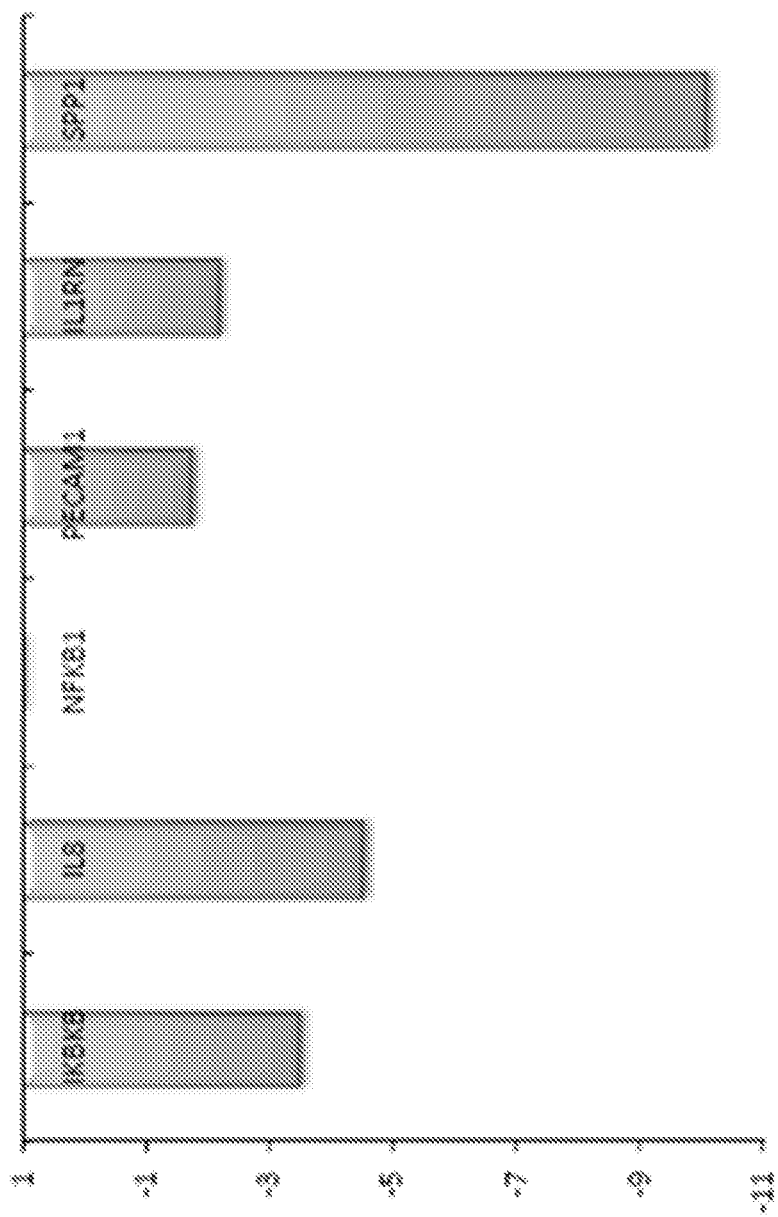
FIG. 26: The effect of PRP treatment on the expression levels in CSCs of genes encoding cytokines.

The impact of PRP treatment on the expression of genes encoding cytokines in pancreatic CSCs was investigated. FIG. 26 shows the down-regulation of genes encoding cytokines associated with cell proliferation, migration and invasion in cancer.

IL-8 and IL-8 receptors have been shown to be overexpressed in pancreatic cancer but suppressed in normal pancreatic tissues, suggesting that IL-8 plays an important role in the invasiveness of human pancreatic cancer. Furthermore, IL-8 has also been reported to promote EMT by modulation of the tumor microenvironment. The results presented here show that the expression of IL-8 was down-regulated (4.5 fold) following PRP treatment. The decrease in IL-8 gene expression detected after PRP treatment further supports the observation that PRP exerts an anti-CSC effect.

Treatment of CSCs with PRP dramatically decreased the expression of Secreted phosphoprotein-1 (SPP1, 10 fold downregulation). SPP1 has been reported to promote cancer cell survival and regulate tumor-associated angiogenesis and inflammation. In addition, PRP treatment induced the down regulation of membrane glycoprotein CD31/PECAM-1, a protein that has been found on many tumor cells, such as human brain gliomas, carcinoma of the cervix, lung cancer, and breast cancer.

g) Expression of CSC Markers Genes

Figure 27:
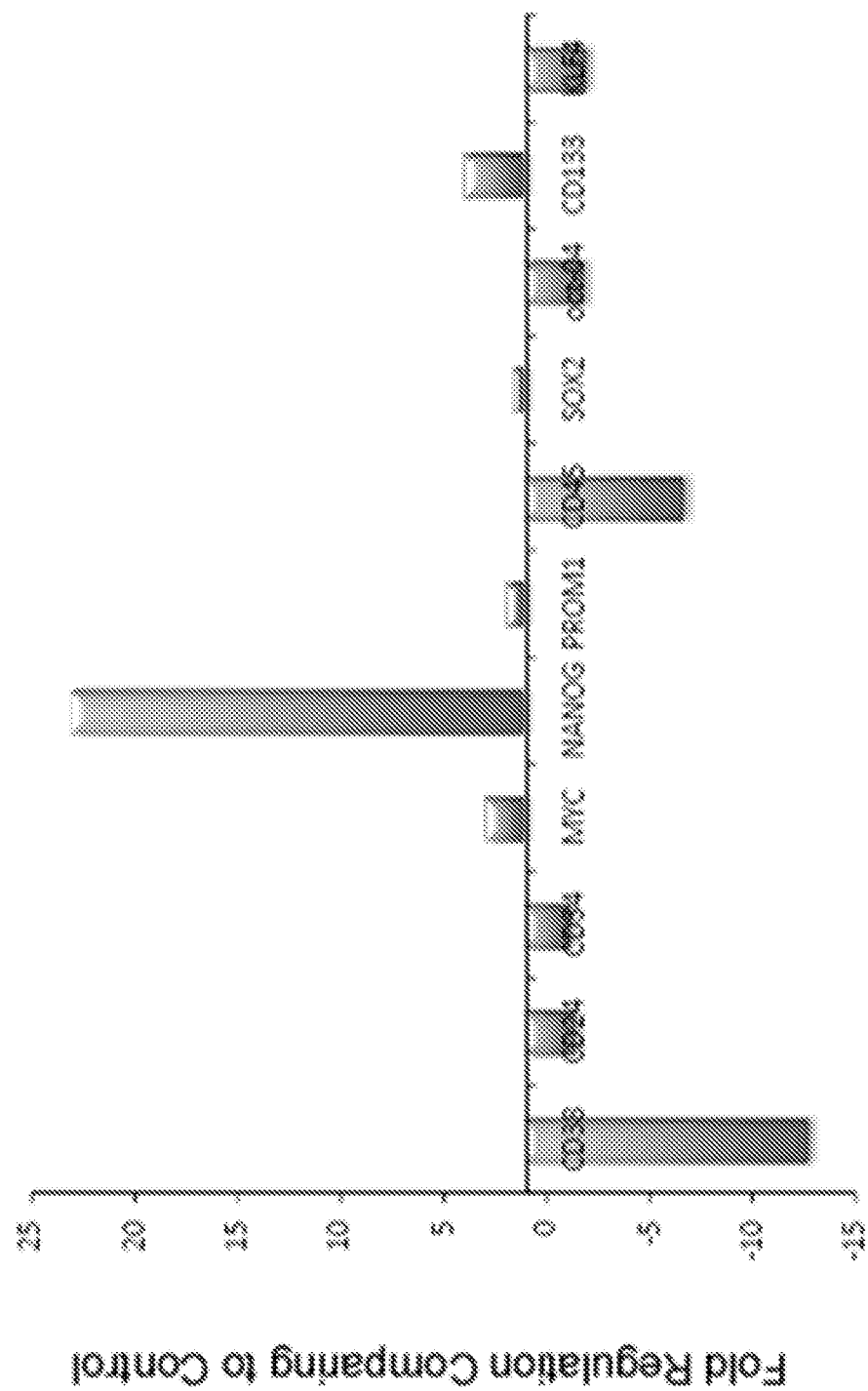
FIG. 27: The effect of PRP treatment on the expression of CSC-marker genes.

PRP treatment of pancreatic CSCs induced the down-regulation of 6 genes recognized as CSC markers (FIG. 27), including CD38, CD45, Oct-04 and KLF4.

h) Expression of Genes Associated with MAPK/ERK Pathway

Figure 28:
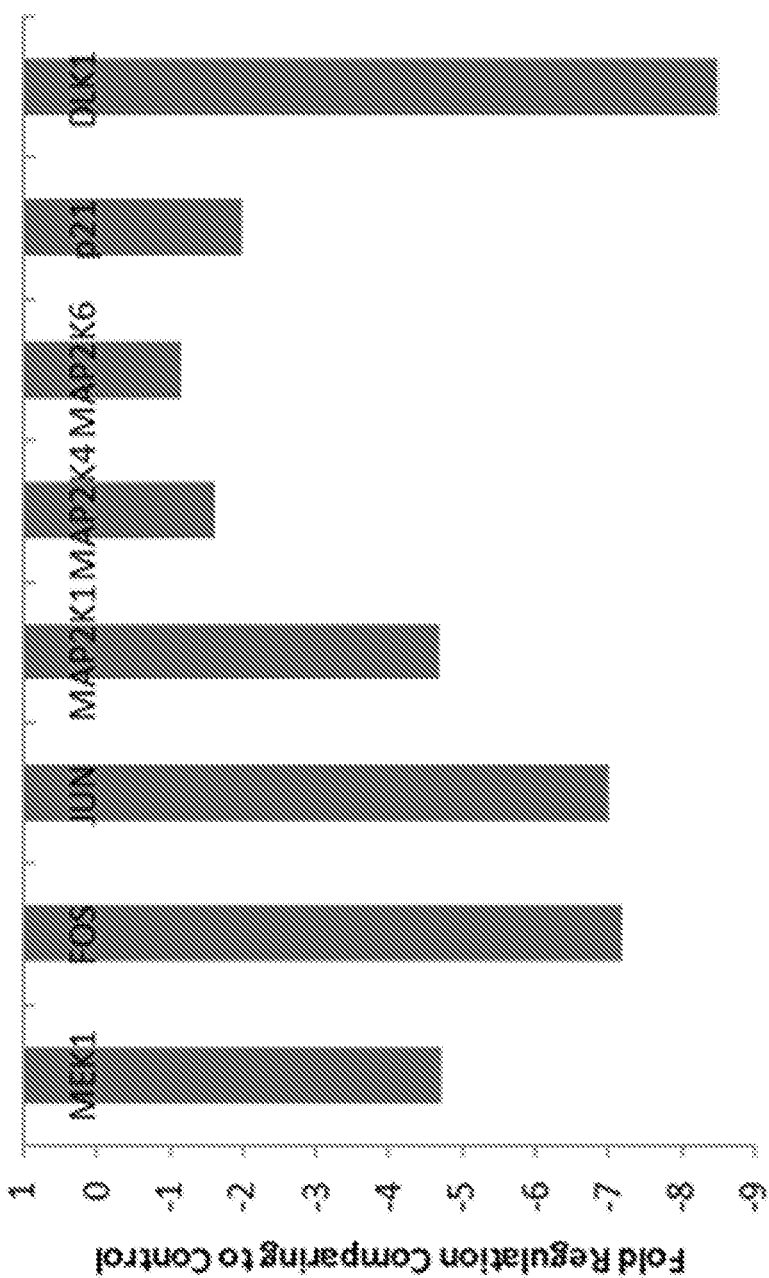
FIG. 28: The effect of PRP treatment on the expression of MAPK-related genes in CSCs.

PRP treatment of pancreatic CSC induced the down-regulation of several MAPK-related genes. The results are shown in FIG. 28.

Conclusion

The results of the above in vitro studies show that:
1. PRP treatment destroys primary spheres and suppresses the ability of CSCs to form secondary spheres and thereby has a direct effect on the cancer stem cell population;
2. PRP has a potent anti-EMT effect in CSCs;
3. PRP has an anti-metastatic effect, enhancing expression of factors which promote cell adhesion and reducing the expression of factors associated with migration processes in CSCs;
4. PRP enhances expression of relevant tumor suppressor genes in CSCs;
5. PRP modulates the expression of CSC marker genes;
6. PRP may induce differentiation of CSCs; and
7. PRP down-regulates the expression of cytokines that are associated with cell proliferation, migration and invasion in cancer.

These results reinforce the therapeutic potential of PRP as an anti-CSC, anti-EMT, anti-metastasis, and anti-tumour drug.

Example 2

Phase 1—In Vivo Study of the Antitumor Activity of PRP Against CSCs

A. Experimental Design:

1—Control group (n=10): untreated mice (inoculated with physiological saline solution)

2—Prevention group: mice are treated with PRP (Trypsinogen/Chymotrypsinogen A), prior to inoculation with CSCs (n=10). PRP was dissolved in physiological saline solution is administered in a single i.v. bolus injection every other day for 3 weeks.

3—Prevention+Treatment group: mice are treated with PRP (Trypsinogen/Chymotrypsinogen A), prior to and after CSC inoculation (n=10). PRP dissolved in physiological saline solution is administered in a single i.v. bolus injection every other day for 3 weeks. The treatment is maintained for 3-4 months.

4—Treatment group: mice are treated with PRP (Trypsinogen/Chymotrypsinogen A), only after CSC inoculation. PRP dissolved in physiological saline solution is administered in a single i.v. bolus injection every other day for 3-4 months.

Phase 2—Study of the Ability of PRP to Inhibit the Initiation of Tumor Capacity of Pancreatic CSC To determine whether PRP treatment can reduce the tumor-initiating capacity of pancreatic CSCs, the following set of experiments are performed. Xenograft experiments are conducted in which tumor formation is induced by injection of pancreatic CSCs previously treated in vitro with PRP. Assessment of tumor formation, and study of tumor characteristics is performed.

A. Experimental design:

1—Control group (n=8). NSG mice are injected with non-treated pancreatic CSCs.

2—IC50 PRP group (n=8). Mice are injected with pancreatic CSCs treated with the IC50 of PRP (Trypsinogen/Chymotrypsinogen A) over 3-6 days.

3—2× IC50 PRP group (n=8). Mice are injected with pancreatic CSCs treated with 2× the IC50 of PRP (Trypsinogen/Chymotrypsinogen A) over 3-6 days.

4—5× IC50 PRP group (n=8). Mice are injected with pancreatic CSCs treated with 5× the IC50 of PRP (Trypsinogen/Chymotrypsinogen A) over 3-6 days.

Phase 3—Experimental Metastasis In Vivo Assay

To determine whether PRP can be used as an anti-metastasis agent, an experimental metastasis assay is performed using immune-deficient mice. The in vivo metastasis model makes use of CSCs-L2T (enriched subpopulation obtained from BxPC3 transfected in vitro with luciferase and the red fluorescent protein td-Tomato) that is directly injected into the circulation of NSG mice (NOD scid gamma mice) through their tail veins. Metastatic progression is monitored by IVIS (Spectrum Preclinical In Vivo Imaging System). Mice are treated with PRP prior to and after the injection of CSC-L2T according to the following experimental design:

A. Experimental Design:

1—Control group (n=8): untreated mice are inoculated with physiological saline solution.

2—Prevention group: Mice are treated with PRP (Trypsinogen/Chymotrypsinogen A) prior to the inoculation of CSCs– L2T. PRP dissolved in physiological saline solution is administered in a single i.v. bolus injection every other day for 3 weeks.

3—Prevention+Treatment group: Mice are treated with PRP (Trypsinogen/Chymotrypsinogen A) prior to and after CSC-L2T inoculation. PRP dissolved in physiological saline solution is administered in a single i.v. bolus injection every other day for 3 weeks. The treatment is maintained for 3-4 months.

4—Treatment group: Mice are treated with PRP (Trypsinogen/Chymotrypsinogen A) only after inoculation with CSCs-L2T. PRP dissolved in physiological saline solution is administered in a single i.v. bolus injection every other day for 3-4 months.

Material and Methods

Phase 1 and 2

Isolation of CSCs

Cancer stem-like cells from BxPC3 pancreatic cancer (adenocarcinoma) cell line are isolated using the ALDEFLUOR assay (StemCell Technologies) by fluorescence-activated cell sorting (FACS) and enriched subpopulation of CSCs will be grown with our specific sphere forming medium (PCT/ES2015/070606) in ultralow attachment plates (Corning).

In Vivo Anti-Tumor Xenograft Studies

To establish xenograft tumors six- to eight week old NSG immunodeficient mice were used. All procedures were approved by the Institutional Animal Care and Use Committee at the University of Granada. Mice were housed and maintained at 20° C. to 24° C., 50% RH, a 14 to 10 h lightdark cycle with food and water ad libitum.

For phase 2, pancreatic CSCs are treated for 3 and 6 days with $IC_{50}$, $2 \times IC_{50}$ and $5 \times IC_{50}$ of PRP. Cell viability is determined prior to the inoculation of PRP-treated CSCs into NSG mice model.

Figure 14:
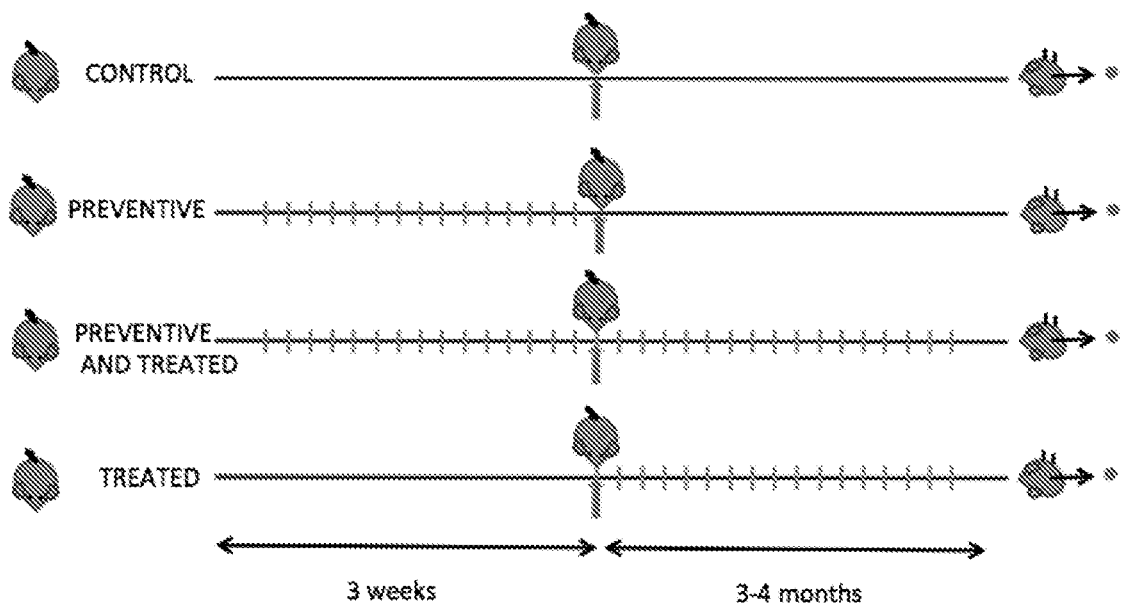
FIG. 14: A. In vivo study design for assessing the antitumor activity of PRP against CSCs. Perpendicular bars represent PRP bolus injection. B. In vivo study design for assessing the ability of PRP to inhibit the initiation of tumour capacity of pancreatic CSCs. C. In vivo study design for assessing metastatic potential of CSCs in vivo. Perpendicular bars stand for PRP bolus injection.
Figure 14:
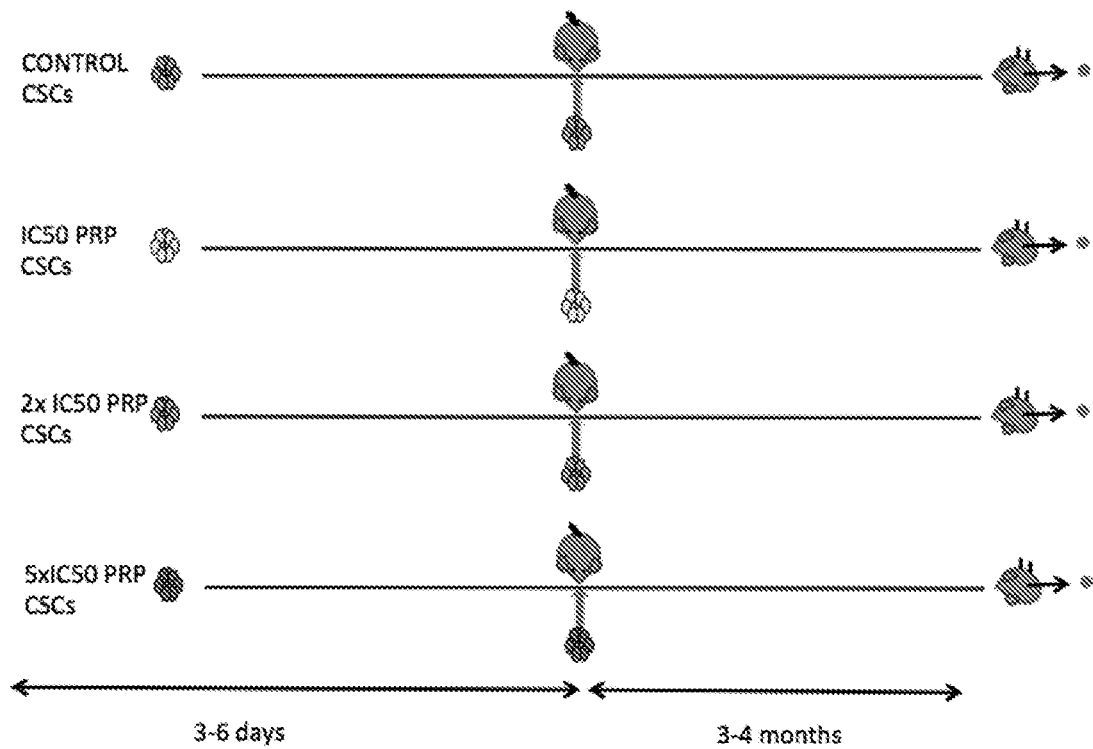
Figure 14:
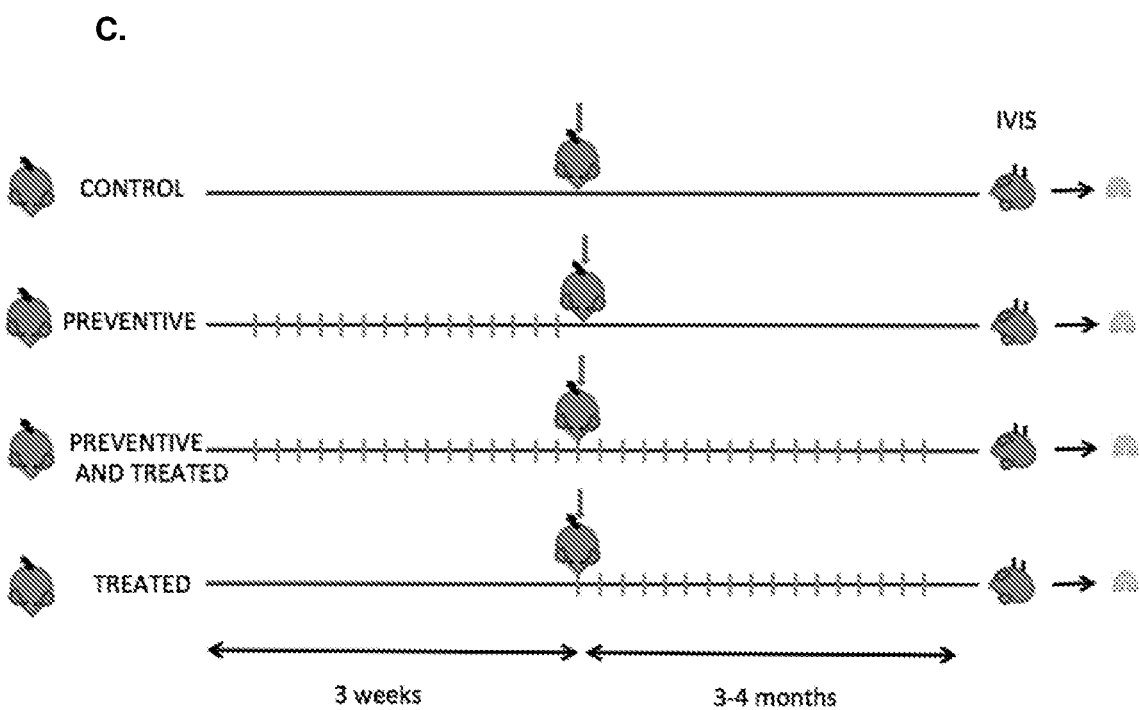

The BxPC3 pancreatic cancer cell line tumors were generated by subcutaneous injections of 100-500 viable cells/mouse* using 26-gauge needles. Animals (n=10 per group) are then randomly assigned as control and treatment groups (groups 1-4) and are treated according to the experimental procedure described previously (FIGS. 14 A and B).

Tumor weight was calculated according to the formula: TW (mg)=tumor volume (mm$^3$)=d$^2 \times$D/2, where d and D are the shortest and longest diameters, respectively. Paraffin-embedded blocks of all tumors are sectioned at 5 µm. Each sample was stained with hematoxylin and eosin (H&E) for histopathologic analysis.

In Vivo PRP Treatment

PRP (Trypsinogen/Chymotrypsinogen A) dissolved in physiological saline solution was administered in a single i.v. bolus injection every other day during the treatment period. The dose administered to groups 2 and 3 was 83.3 mg/kg trypsinogen and 500 mg/kg chymotrypsinogen A. Trypsinogen and Chymotrypsinogen A were provided in combination and administered in a single injection. The dosing volume was 10 mL/kg. The volume of dosing solution administered to each animal was calculated and adjusted based on individual body weight measured immediately prior to dosing.

Treatments were administered for 3 weeks before tumour induction (prevention group) or for 3 weeks before tumour induction and for at least 4 weeks (preferably up to 9.5 weeks) after induction (prevention+treatment group).

Preliminary Metastasis Assay

Mice were killed with a lethal dose of sodium pentobarbital (100 mg/kg body weight). Thoracic organs are removed, the lung is washed in cold PBS and weighed. Other visceral organs are removed and inspected for presence of metastases. Lung is fixed in formalin and embedded in paraffin. Hematoxylin and eosin (H&E)-stained lung-sections is analysed for metastatic nodule presence.

Measurement of Effect of PRP on Tumour Growth

The effect of PRP on tumour growth was determined by calculating the tumour growth inhibition ratio, T/C. T/C was determined using two different methods: the first measuring tumour volume at the end of treatment and the second measuring the rate of tumour growth over the course of treatment.

Figure 18:
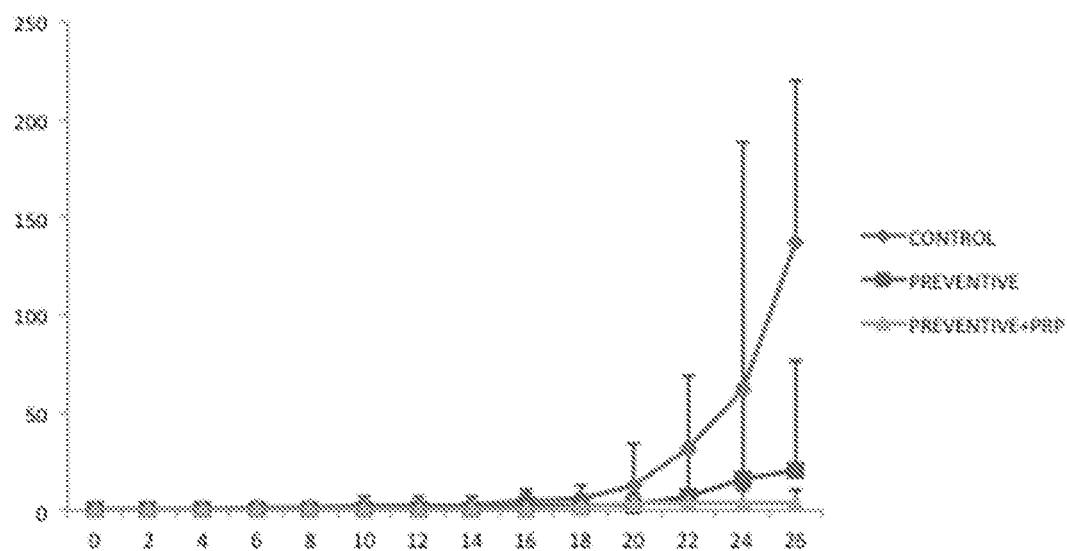
FIG. 18: A. Graph depicting the tumour volumes in each experimental group (control, prevention group and prevention+treatment group), measured every 2 days following CSC inoculation. X-axis denotes the number of days from development of the tumour. Day 0 corresponds to 30 days from CSC inoculation. B. Graph depicting the tumour volumes in each experimental group (control, prevention group and prevention+treatment group), measured every 2 days (rate-based T/C) following CSC inoculation. X-axis denotes the number of days from development of the tumour. Day 0 corresponds to 30 days from CSC inoculation. Asterisks denote statistical significance, $p<0.05$.
Figure 18:
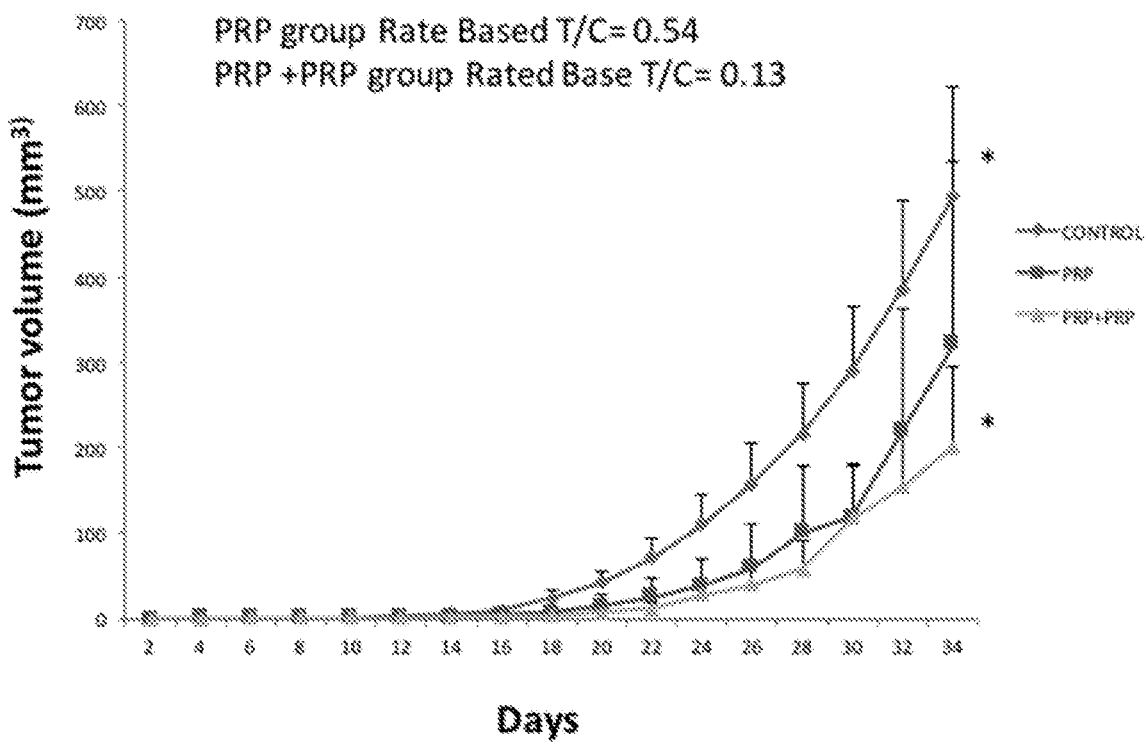

In the first method, the ratio of mean volume of control tumours (C) versus the mean volume of treated tumours (T) at the final day of treatment was calculated. T/C≤0.45 is the consensus cut-off to indicate efficacy of a given treatment, In the second method, the rate based T/C described by Hather et al., (2014) was used. This method is based on fitting the growth curve of each tumour to an exponential model. The rate based T/C uses all available data, thus, is able to account for random differences in the initial volume. In addition, fitting all the data reduces the effect of measurement noise and allows the rate based T/C estimates to be more precise. A p-value is also computed using a two sided t-test with unequal variances applied to the estimated tumour growth rates. The p-value calculation assumes that the estimated tumor growth rates are normally distributed within each treatment group. A threshold of 0.4 was chosen because it is a common cut-off to determine if the antitumor activity is sufficient to be of practical significance. The evolution of tumour growth was therefore evaluated by measuring tumour volume every 2 days over 36 days and the data was analyzed using an Excel spreadsheet that computes the rate based T/C (FIG. 18). The rate based T/C was 0.54 (p=0.17) for pre-treated group and 0.13 (p=0.001) for the pre-treated and treated group. Indicating that the follow up treatment with PRP significantly inhibits tumour growth.

Effect of PRP on Tumour Incidence and Weight

The Tumourigenesis Index (TIn) is an index that reflects the relative tumour incidence and tumour weight in a subject. The TIn can be used to measure malignancy or tumour aggressiveness.

Phase 3

Lentivirus Transfections 293T cells are co-transfected with a lentiviral vector encoding for the firefly luciferase and the red fluorescent protein td-Tomato (L2T) 26, a packaging vector (psPAX2) and an envelope vector (pCMV-VSVG) using lipofectamine transfection reagent (Life Technologies). Viral particles produced from 293T cells are collected and used to infect BxPC3 cells. Briefly, supernatant is recovered after 48 h from 293T transfected cells and filtered by a 0.45 µm pore membrane and added to BxPC3 plated cells supplemented with 4 µg/mL polybrene (Sigma-Aldrich). After viral infection, td-Tomato+ cells are selected for stable integration of the transfects by FACS.

Experimental Lung Metastasis In Vivo Assay

BxPC3 CSCs-L2T are injected into the tail vein of 4-6 weeks old female NSG mice (n=8 per group). Bioluminescence is monitored by IVIS at day 0 and weekly by injecting intraperitoneally 150 mg/kg of D-Luciferine (Thermo Fisher). After 4 weeks, mice are euthanized and lungs are excised, photographed for td-Tomato expression and assayed for luciferase activity washing lungs with 150 µg/mL of D-luciferine diluted in PBS. Excised lungs are also used for Hematoxylin and Eosin staining and confocal microscopy analysis.

In Vivo PRP Treatment

PRP (Trypsinogen/Chymotrypsinogen A) dissolved in physiological saline solution is administered in a single i.v. bolus injection every other day for 3-4 months.

Histological Analysis

Lungs are immersed in 4% paraformaldehyde in 0.1 M PBS for 4 h at 4° C., washed in 0.1M PBS and embedded in paraffin in an automatic tissue processor (TP1020, Leica, Germany). The paraffin blocks are cut into 4 mm sections for staining. Sections are deparaffinized with xylene and hydrated with decreasing alcohol concentrations (absolute to 70%), and will be stained with hematoxylin-eosin. Sections are then dehydrated with increasing alcohol concentrations (95% to absolute), and cleared with xylene and mounted with mounting medium. Observation under light microscopy and digital image acquisition is performed with an inverted microscope (Nikon H550s).

Immunohistochemical Analysis

Lungs are immersed in 10% formaline at room temperature overnight, washed in 0.1M PBS, and preserved in 30% sucrose in PBS for 24 h. The material is then soaked in OCT compound (Sakura Finitek Europe B.V., Netherlands), frozen in liquid nitrogen and blocks stored at −40° C. until use. The OCT blocks are cut into 8 mm sections and collected on SuperFrost slides (Menzel-Glasser, Germany). The sections are hydrated with PBS and mounted with mounting medium with DAPI. Observation under fluorescent microscopy and digital image acquisition will be performed with a confocal microscope (Nikon A1).

Results

Preliminary results for Phase 1 experiments were obtained 4 weeks and 9.5 weeks after CSC inoculation. The results demonstrate the anti-tumour efficacy of PRP (Trypsinogen/Chymotrypsinogen A) against tumours induced by BxPC3 in human pancreatic CSCs.

FIGS. 15 to 19 show the results for the Phase 1 study, 9.5 weeks after commencement of the trial (i.e., 67 days after CSC inoculation).

Figure 15:
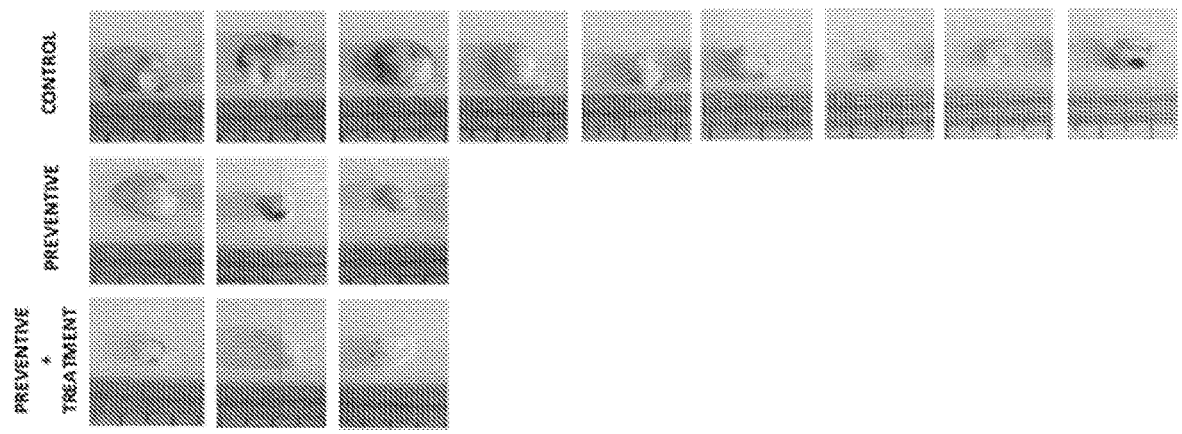
FIG. 15: Images of tumours excised from mice, 9.5 weeks after inoculation with CSCs. Control group, n=10; prevention group, n=8; prevention+treatment group n=6.

FIG. 15 provides images of excised tumours from mice in groups 1, 2 and 3.

Figure 16:
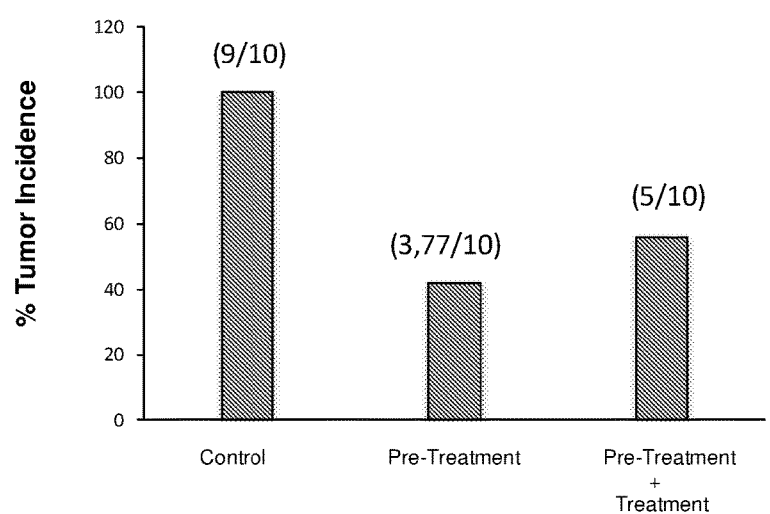
FIG. 16: Percentage tumour incidence in mice following inoculation with CSCs. Tumour incidence was measured 9.5 weeks after inoculation. Percentage incidence in prevention and prevention+treatment groups is shown as a proportion of the incidence observed in control mice (no prevention or treatment). P=0.039

FIG. 16 shows % tumour incidence in groups 1, 2 and 3: 9 of 10 control mice developed a tumour after subcutaneous injection of the CSC-enriched population of pancreatic BxPC3 (this value was interpreted as 100% tumour incidence). In both groups 2 and 3 (i.e., prevention and prevention+treatment), fewer than 50% of mice developed tumours (41% in group 2; 50% in group 3). These results show that preventative treatment with PRP (Trypsinogen/Chymotrypsinogen A) prior to CSC inoculation has a clear suppressive effect on pancreatic CSC tumour engrafting.

Figure 17:
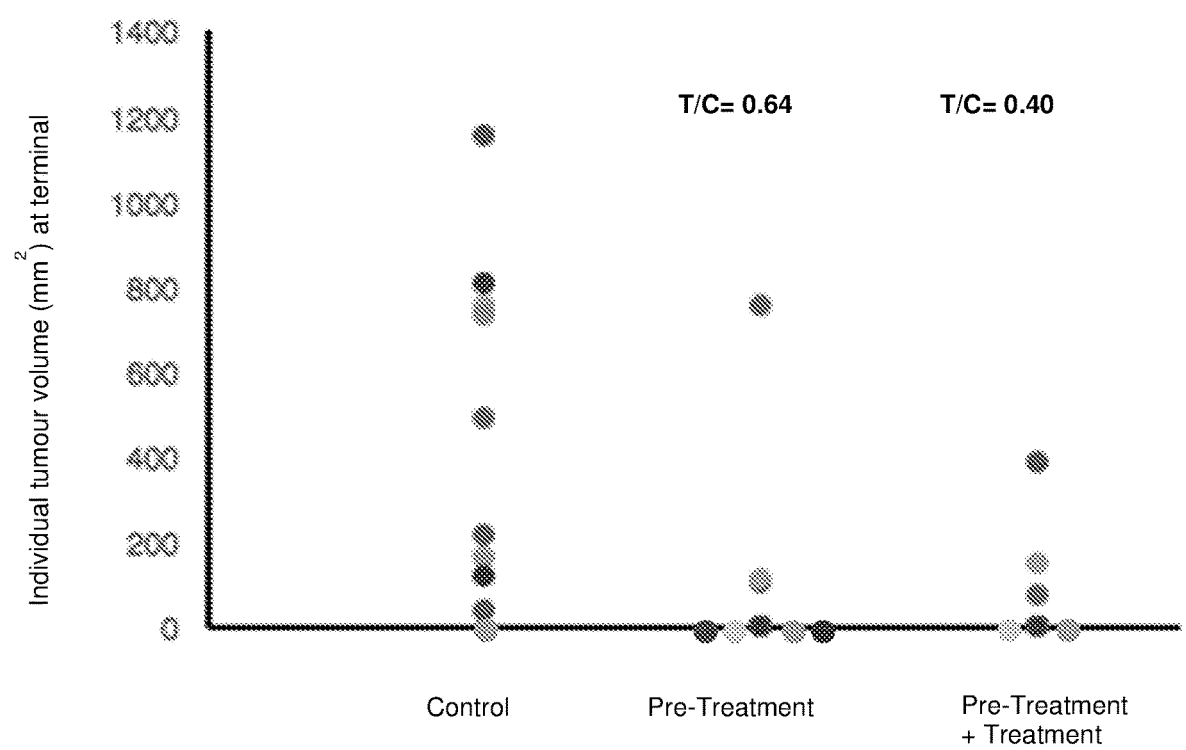
FIG. 17: Mean tumour volume ($mm^2$) in mice±SE, at treatment termination (9.5 weeks after inoculation). The difference in tumour weight between the control group and the prevention+treatment group was statistically significant, $p<0.05$.

The effect of PRP treatment in reducing tumour growth was assessed and the results are shown in FIGS. 17 and 18. FIG. 17 shows the volume of each tumour at the final day of treatment together with the T/C value (calculated using method 1) for both group 2 and 3 mice. These results show that preventative treatment with PRP (group 2) and prevention+treatment (group 3) decrease tumour uptake and impair tumour growth compared with control non-treated animals (T/C=0.64 in group 2 and T/C=0.40 in group 3).

Rate-based T/C for the two experimental groups is shown in FIG. 18. The rate based T/C was 0.54 (p=0.17) for prevention group (group 2) and 0.13 (p=0.001) for the prevention+treatment group (group 3). These results show that the follow up treatment with PRP significantly inhibits tumour growth, evidenced by the reduced volume of tumours in this treatment group. Specifically, for group 2 mice, tumour volume was only 54% of the volume seen in tumours of control mice. In group 3 mice, the tumour volume was only 13% that of the tumours in control mice.

Taken together, the results presented in FIGS. 17 and 18 show a significantly reduced incidence of tumour development and reduced volume of any tumours that do develop in mice receiving PRP as a preventative and in mice receiving both preventative and post-CSC inoculation (treatment) PRP.

Figure 19:
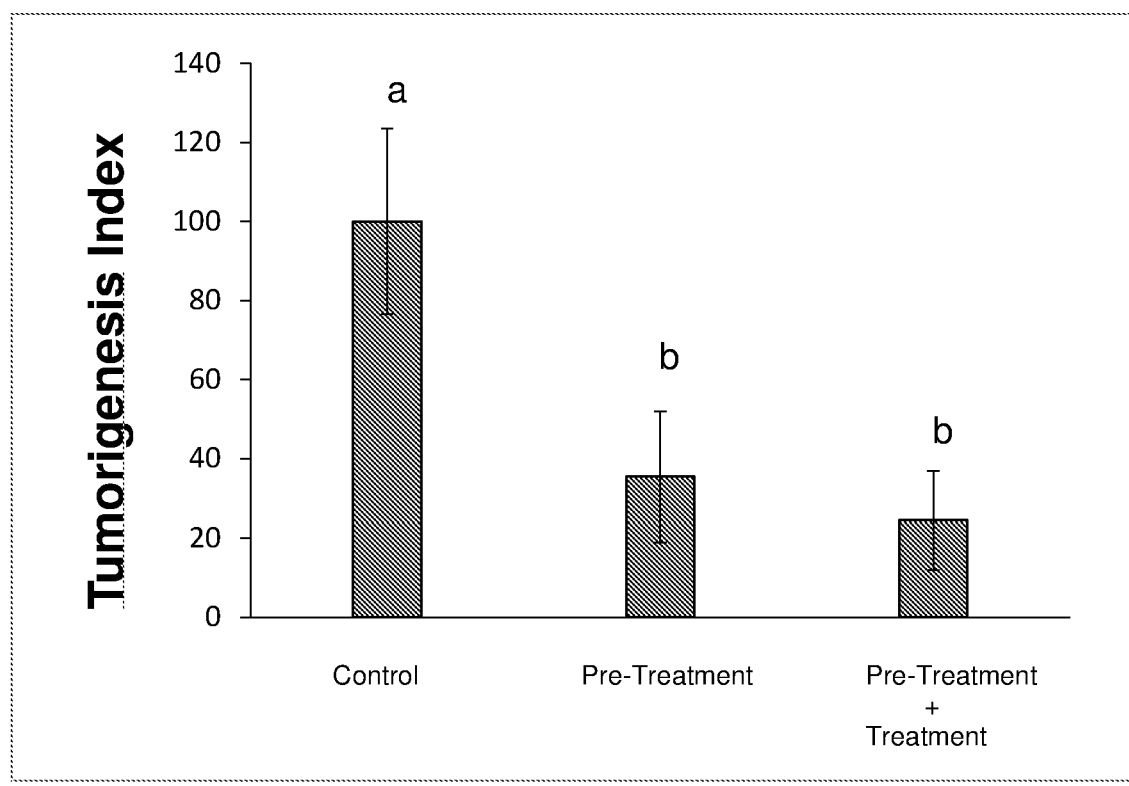
FIG. 19: Tumourigenesis index (TIn)±SE in control, prevention and prevention+treatment groups 9.5 weeks after CSC inoculation. TIn is a measure of tumour incidence and tumour weight. The difference in TIn between control and both prevention and prevention+treatment groups was statistically significant, $p<0.01$.

FIG. 19 shows that significant differences in TIn (p<0.01) were observed when mice received preventative PRP or when they received both preventative PRP and PRP after CSC inoculation, indicating the anti-tumourigenic effect of PRP.

Figure 20:
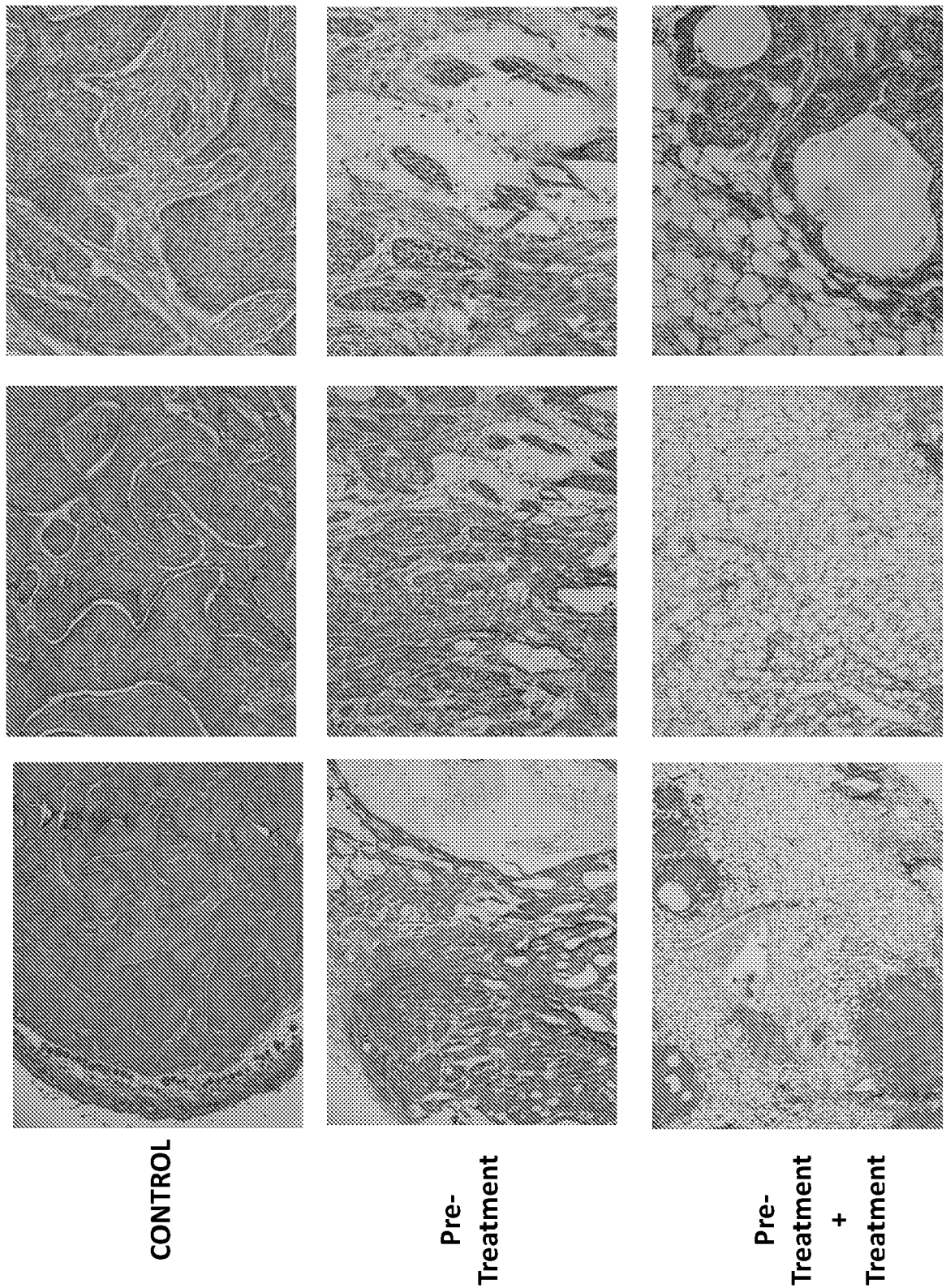
FIG. 20: Representative images showing H&E staining. In the subcutaneous xenograft model, tumours from mice in the control, prevention and prevention+treatment groups were excised and fixed. BxPC3 tumor tissues were embedded in paraffin, sectioned with 5 µm thickness and stained with H&E (left: magnification, 20×; middle: magnification, 10×; right: magnification, ×40).
Figure 21:
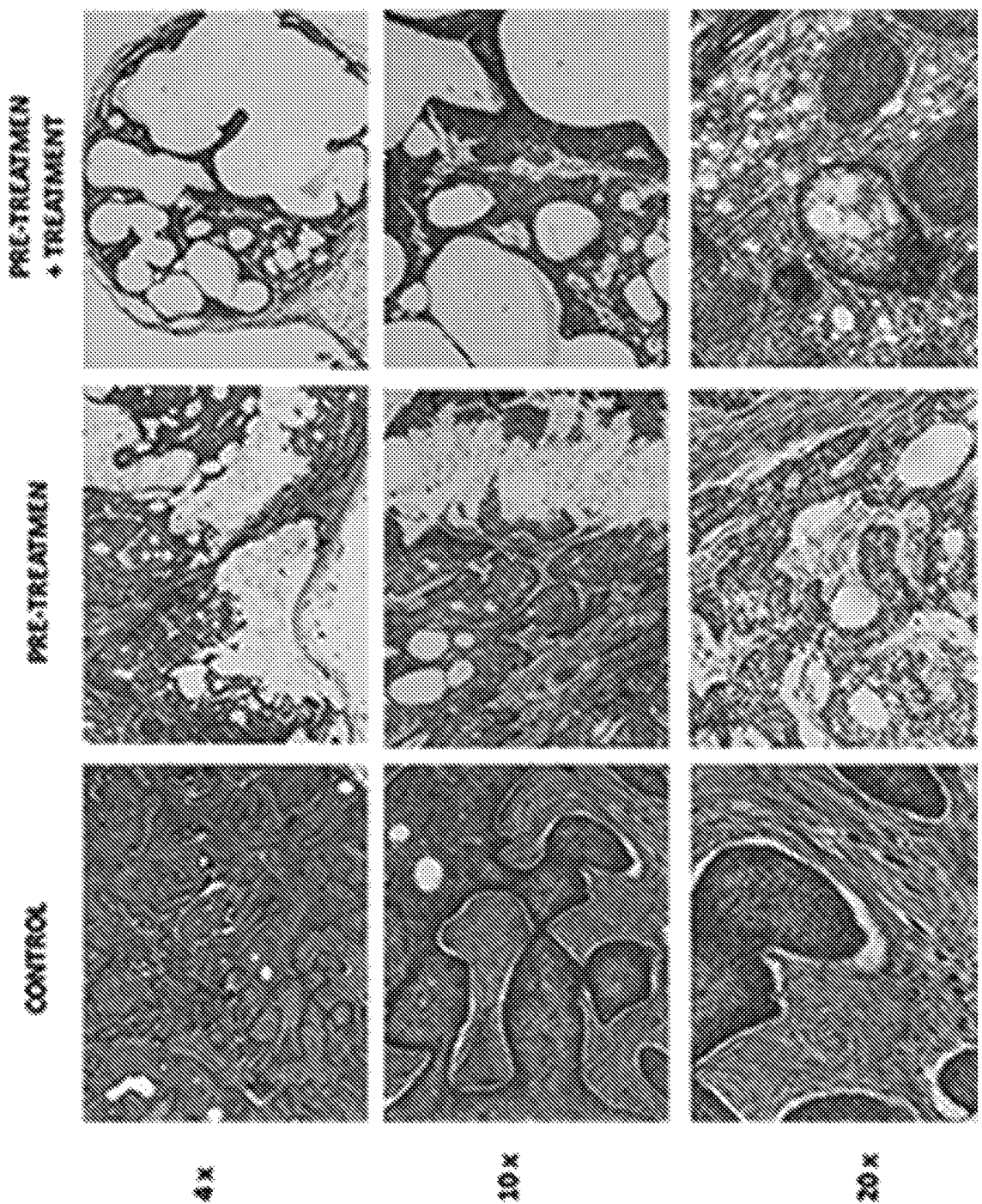
FIG. 21: Representative images showing Masson-trichome staining of BxPC3 tumors in the subcutaneous xenograft model. Staining of tumours from mice in the control, prevention and prevention+treatment groups are shown.

FIGS. 20 and 21 shows H&E staining and Masson-trichome staining, respectively, of sections from tumours that were excised from mice in the control, prevention and prevention+treatment groups. The representative images show noticeable differences in the density of the tumours, with significantly reduced density and increased gaps between cells observed in the tumours from both prevention and prevention+treatment groups. Further, the presence of fibrotic tissue in tumours from mice receiving PRP (both prevention and prevention+treatment groups) was significantly reduced compared to control mice.

In conclusion, the data demonstrate the anti-tumour effect of PRP as a preventative and treatment. PRP impaired engrafting of CSC tumours in mice and substantially reduced progression for those tumours which were initiated following CSC inoculation.

Example 3

Treatment of cancer using the invention may be implemented in accordance with the following.

An individual diagnosed with colon cancer may have the bulk of the tumour mass removed by surgery (laparoscopic or conventional). After resection of the tumour mass the individual is administered chymotrypsinogen and trypsinogen, optionally in combination with chemotherapy or radiotherapy. Prior to administration the presence of colon cancer stem cells may be determined by identifying cells in the individual, or near the site of resection, that express markers characteristic of colon cancer stem cells. Exemplary markers may be CD326 and CD44 or any other markers described herein (see, Table 1). The individual is then monitored for recurrence at the original tumour site and appearance of metastasis at known sites of colon cancer metastasis. The result is prevention or delay of recurrence or metastasis.

An individual diagnosed with pancreatic cancer may have the bulk of the tumour mass removed by surgery (laparoscopic or conventional). After resection of the tumour mass the individual is administered chymotrypsinogen and trypsinogen, optionally in combination with chemotherapy or radiotherapy. Prior to administration, the presence of pancreatic cancer stem cells may be determined by identifying cells in the individual, or near the site of resection, that express markers characteristic of pancreatic cancer stem cells. Exemplary markers may be CD326, CD44 and CxCR4 or any other markers described herein (see, Table 1). The individual is then monitored for recurrence at the original tumour site and appearance of metastasis at known sites of pancreatic cancer metastasis. The result is prevention or delay of recurrence or metastasis.

Similar methods may be applied to other cancers, preferably solid tumours, such as prostate cancer, breast cancer, ovarian cancer or any other cancer described herein.

The invention claimed is:

1. A method of minimising the progression of cancer in a subject who has received a treatment for cancer, wherein the method comprises:
    detecting the presence of cancer stem cells in the subject by identifying cells expressing one or more cancer stem cell markers, wherein the cancer stem cell markers comprise: CD34+, CD38−, CD71−, CD90−, C117−, CD123+; or ESA+, CD44+, CD24−, ALDH-1 or CD133+CD49f+, CD90+; or CD133+, BCRP1+, A2B5+, SSEA-1+; or CD133+, ABCG2: or CD133+, CD44+, CD166+, EpCAM+, CD24+, CD326+, C D44+; or CD138−; or CD44+, α2β1, CD 133+; or CD133+, CD44+, EnCAM+, CD24+, CD326+, CD44+, CxCr4+; or CD20+, or CD144+; and
    wherein when the subject is determined to have cancer stem cells, administering to the subject, therapeutically effective amounts of chymotrypsinogen and trypsinogen, wherein the weight ratio of chymotrypsinogen:trypsinogen is in the range of between 4:1 to 8:1.

2. The method according to claim 1, wherein the subject is in partial or complete remission.

3. The method according to claim 1, wherein the method comprises treating minimal residual disease in a subject who has received a treatment for cancer.

4. The method according to claim 1, wherein the method comprises preventing recurrence of cancer in the subject.

5. The method according to claim 1 wherein the treatment for cancer is selected from the group consisting of surgical excision of the tumour, radiotherapy, chemotherapy, immunotherapy or a combination thereof.

6. A method according to claim 1 wherein the subject does not have detectable cancer at the time that the chymotrypsinogen and trypsinogen are administered.

7. The method according to claim 1 wherein the weight ratio of chymotrypsinogen:trypsinogen is in the range of between 5:1 to 7:1.

8. The method according to claim 1 wherein the weight ratio of chymotrypsinogen:trypsinogen is about 6:1.

9. The method according to claim 1 wherein the chymotrypsinogen and trypsinogen are administered simultaneously.

10. A method according to claim 1, wherein the cancer stem cells are differentiated following administration of the chymotrypsinogen and trypsinogen.

11. A method according to claim 1, wherein the cancer is selected from the group consisting of pancreatic cancer, colon cancer, neuroblastoma, ovarian cancer, non-small lung cell cancer, skin cancer, esophageal cancer, lung cancer and breast cancer.

12. The method of claim 1, wherein the therapeutically effective amounts of chymotrypsinogen and trypsinogen reduce proliferation of cancer stem cells, reduce the population of cancer stem cells in a cancer cell population, inhibit sphere formation, reduce the expression of genes in cancer stem cells, prevent tumour-initiating capacity of cancer stem cells, or reduce tumour volume.

* * * * *

SEQUENCE LISTING

<160> NUMBER OF SEQ ID NOS: 22

<210> SEQ ID NO 1

```
<211> LENGTH: 20
<212> TYPE: DNA
<213> ORGANISM: Artificial Sequence
<220> FEATURE:
<223> OTHER INFORMATION: SNAIL Forward primer

<400> SEQUENCE: 1
accccacatc cttctcactg                                            20

<210> SEQ ID NO 2
<211> LENGTH: 20
<212> TYPE: DNA
<213> ORGANISM: Artificial Sequence
<220> FEATURE:
<223> OTHER INFORMATION: SNAIL Reverse primer

<400> SEQUENCE: 2
tacaaaaacc cacgcagaca                                            20

<210> SEQ ID NO 3
<211> LENGTH: 20
<212> TYPE: DNA
<213> ORGANISM: Artificial Sequence
<220> FEATURE:
<223> OTHER INFORMATION: SLUG Forward primer

<400> SEQUENCE: 3
tgcgatgccc agtctagaaa                                            20

<210> SEQ ID NO 4
<211> LENGTH: 19
<212> TYPE: DNA
<213> ORGANISM: Artificial Sequence
<220> FEATURE:
<223> OTHER INFORMATION: SLUG Reverse primer

<400> SEQUENCE: 4
ttctcccccg tgtgagttc                                             19

<210> SEQ ID NO 5
<211> LENGTH: 20
<212> TYPE: DNA
<213> ORGANISM: Artificial Sequence
<220> FEATURE:
<223> OTHER INFORMATION: E-CADHERIN Forward primer

<400> SEQUENCE: 5
aattcctgcc attctgggga                                            20

<210> SEQ ID NO 6
<211> LENGTH: 20
<212> TYPE: DNA
<213> ORGANISM: Artificial Sequence
<220> FEATURE:
<223> OTHER INFORMATION: E-CADHERIN Reverse primer

<400> SEQUENCE: 6
tcttctccgc ctccttcttc                                            20

<210> SEQ ID NO 7
<211> LENGTH: 20
<212> TYPE: DNA
<213> ORGANISM: Artificial Sequence
<220> FEATURE:
<223> OTHER INFORMATION: N-CADHERIN Forward primer

<400> SEQUENCE: 7
```

```
tgagcctgaa gccaacctta                                                  20

<210> SEQ ID NO 8
<211> LENGTH: 20
<212> TYPE: DNA
<213> ORGANISM: Artificial Sequence
<220> FEATURE:
<223> OTHER INFORMATION: N-CADHERIN Reverse primer

<400> SEQUENCE: 8
aggtcccctg gagttttctg                                                  20

<210> SEQ ID NO 9
<211> LENGTH: 20
<212> TYPE: DNA
<213> ORGANISM: Artificial Sequence
<220> FEATURE:
<223> OTHER INFORMATION: VIMENTIN Forward primer

<400> SEQUENCE: 9
agctaaccaa cgacaaagcc                                                  20

<210> SEQ ID NO 10
<211> LENGTH: 20
<212> TYPE: DNA
<213> ORGANISM: Artificial Sequence
<220> FEATURE:
<223> OTHER INFORMATION: VIMENTIN Reverse primer

<400> SEQUENCE: 10
tccactttgc gttcaaggtc                                                  20

<210> SEQ ID NO 11
<211> LENGTH: 20
<212> TYPE: DNA
<213> ORGANISM: Artificial Sequence
<220> FEATURE:
<223> OTHER INFORMATION: OCT4 Forward primer

<400> SEQUENCE: 11
caccatctgt cgcttcgagg                                                  20

<210> SEQ ID NO 12
<211> LENGTH: 22
<212> TYPE: DNA
<213> ORGANISM: Artificial Sequence
<220> FEATURE:
<223> OTHER INFORMATION: OCT4 Reverse primer

<400> SEQUENCE: 12
agggtctccg atttgcatat ct                                               22

<210> SEQ ID NO 13
<211> LENGTH: 20
<212> TYPE: DNA
<213> ORGANISM: Artificial Sequence
<220> FEATURE:
<223> OTHER INFORMATION: KLF4 Forward primer

<400> SEQUENCE: 13
cgaacccaca caggtgagaa                                                  20

<210> SEQ ID NO 14
<211> LENGTH: 22
<212> TYPE: DNA
```

<213> ORGANISM: Artificial Sequence
<220> FEATURE:
<223> OTHER INFORMATION: KLF4 Reverse primer

<400> SEQUENCE: 14
tacggtagtg cctggtcagt tc                                            22

<210> SEQ ID NO 15
<211> LENGTH: 20
<212> TYPE: DNA
<213> ORGANISM: Artificial Sequence
<220> FEATURE:
<223> OTHER INFORMATION: SOX 2 Forward primer

<400> SEQUENCE: 15
caagatgcac aactcgcaga                                               20

<210> SEQ ID NO 16
<211> LENGTH: 20
<212> TYPE: DNA
<213> ORGANISM: Artificial Sequence
<220> FEATURE:
<223> OTHER INFORMATION: SOX2 Reverse primer

<400> SEQUENCE: 16
catgagcgtc ttggttttcc                                               20

<210> SEQ ID NO 17
<211> LENGTH: 21
<212> TYPE: DNA
<213> ORGANISM: Artificial Sequence
<220> FEATURE:
<223> OTHER INFORMATION: NANOG Forward primer

<400> SEQUENCE: 17
tcctgaacct cagctacaaa c                                             21

<210> SEQ ID NO 18
<211> LENGTH: 20
<212> TYPE: DNA
<213> ORGANISM: Artificial Sequence
<220> FEATURE:
<223> OTHER INFORMATION: NANOG Reverse primer

<400> SEQUENCE: 18
gcgtcacacc attgctattc                                               20

<210> SEQ ID NO 19
<211> LENGTH: 22
<212> TYPE: DNA
<213> ORGANISM: Artificial Sequence
<220> FEATURE:
<223> OTHER INFORMATION: C-MYC Forward primer

<400> SEQUENCE: 19
gagtctggat caccttctgc tg                                            22

<210> SEQ ID NO 20
<211> LENGTH: 22
<212> TYPE: DNA
<213> ORGANISM: Artificial Sequence
<220> FEATURE:
<223> OTHER INFORMATION: C-MYC Reverse primer

<400> SEQUENCE: 20
aggatagtcc ttccgagtgg ag                                            22

```
<210> SEQ ID NO 21
<211> LENGTH: 21
<212> TYPE: DNA
<213> ORGANISM: Artificial Sequence
<220> FEATURE:
<223> OTHER INFORMATION: CD133 Forward primer

<400> SEQUENCE: 21
cagaataata aacagcagcc c                                            21

<210> SEQ ID NO 22
<211> LENGTH: 21
<212> TYPE: DNA
<213> ORGANISM: Artificial Sequence
<220> FEATURE:
<223> OTHER INFORMATION: CD133 Reverse primer

<400> SEQUENCE: 22
gattatgaca agccagaaac t                                            21
```